US012751770B2

(12) United States Patent
Nakazato

(10) Patent No.: US 12,751,770 B2
(45) Date of Patent: Oct. 6, 2026

(54) INFORMATION PROCESSING APPARATUS, ULTRASOUND ENDOSCOPE, INFORMATION PROCESSING METHOD, AND PROGRAM

(71) Applicant: FUJIFILM CORPORATION, Tokyo (JP)

(72) Inventor: Takeharu Nakazato, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 436 days.

(21) Appl. No.: 18/304,368

(22) Filed: Apr. 21, 2023

(65) Prior Publication Data

US 2023/0380910 A1 Nov. 30, 2023

(30) Foreign Application Priority Data

May 31, 2022 (JP) ................................ 2022-088987

(51) Int. Cl.
*A61B 17/34* (2006.01)
*A61B 8/00* (2006.01)
(Continued)

(52) U.S. Cl.
CPC ................ *A61B 34/20* (2016.02); *A61B 8/06* (2013.01); *A61B 8/12* (2013.01); *A61B 8/4254* (2013.01);
(Continued)

(58) Field of Classification Search
CPC ............ A61B 34/20; A61B 2017/3413; A61B 17/3478; G06T 2207/10068; G06T 2207/10132; G06T 2207/30004
See application file for complete search history.

(56) References Cited

U.S. PATENT DOCUMENTS

2005/0054895 A1* 3/2005 Hoeg .................... A61B 90/36 600/117
2009/0287080 A1* 11/2009 Nishina ................. A61B 10/04 600/104

(Continued)

FOREIGN PATENT DOCUMENTS

JP 2011-000173 A 1/2011
JP 2012-040207 A 3/2012

(Continued)

OTHER PUBLICATIONS

English language translation of the following: Office action dated Dec. 2, 2025 from the JPO in a Japanese patent application No. 2022-088987 corresponding to the instant patent application. This office action translation is submitted now in order to supplement the understanding of the cited references which are being disclosed in the instant Information Disclosure Statement.

(Continued)

*Primary Examiner* — Amal Aly Farag
(74) *Attorney, Agent, or Firm* — SOLARIS Intellectual Property Group, PLLC

(57) ABSTRACT

An information processing apparatus includes a processor. The processor acquires an actual ultrasound image generated as an image showing an aspect of an observation target region including a specific part on the basis of reflected waves obtained by emitting ultrasonic waves from a medical module to the observation target region. In addition, the processor acquires a virtual ultrasound image generated as an ultrasound image virtually showing an aspect of the observation target region on the basis of volume data indicating the observation target region. Further, the processor specifies a positional relationship between a first position where the medical module is present and a second position (Continued)

where the specific part is present on the basis of the actual ultrasound image and the virtual ultrasound image.

17 Claims, 28 Drawing Sheets

(51) Int. Cl.

| | |
|---|---|
| ***A61B 8/06*** | (2006.01) |
| ***A61B 8/08*** | (2006.01) |
| ***A61B 8/12*** | (2006.01) |
| ***A61B 34/20*** | (2016.01) |
| ***G06T 7/73*** | (2017.01) |

(52) U.S. Cl.

CPC .............. *A61B 8/463* (2013.01); *A61B 8/488* (2013.01); *G06T 7/74* (2017.01); *A61B 2017/3413* (2013.01); *A61B 2034/2065* (2016.02); *G06T 2207/10068* (2013.01); *G06T 2207/10132* (2013.01); *G06T 2207/30004* (2013.01); *G06T 2207/30204* (2013.01)

(56) References Cited

U.S. PATENT DOCUMENTS

| | | | | |
|---|---|---|---|---|
| 2012/0083702 | A1* | 4/2012 | Ingold, Jr. ............ | A61B 5/0205 600/483 |
| 2012/0287238 | A1 | 11/2012 | Onishi et al. | |
| 2015/0257847 | A1* | 9/2015 | Higgins ................ | G06T 19/003 600/103 |
| 2017/0251988 | A1 | 9/2017 | Weber et al. | |
| 2019/0282211 | A1* | 9/2019 | Merritt ................. | A61B 8/4416 |
| 2019/0320878 | A1* | 10/2019 | Duindam .................. | G06T 7/30 |
| 2020/0170617 | A1 | 6/2020 | De Vaan et al. | |
| 2022/0156925 | A1 | 5/2022 | Bydlon et al. | |

FOREIGN PATENT DOCUMENTS

| | | |
|---|---|---|
| JP | 2017-527401 A | 9/2017 |
| JP | 2022-509316 A | 1/2022 |
| JP | 2022-523445 A | 4/2022 |
| WO | 2012/101888 A1 | 8/2012 |
| WO | 2019/088008 A1 | 5/2019 |

OTHER PUBLICATIONS

English language translation of the following: Decision of Refusal dated Mar. 24, 2026 from the JPO in a Japanese patent application No. 2022-088987 corresponding to the instant patent application.

* cited by examiner

INFORMATION PROCESSING APPARATUS, ULTRASOUND ENDOSCOPE, INFORMATION PROCESSING METHOD, AND PROGRAM

CROSS-REFERENCE TO RELATED APPLICATIONS

This application claims priority under 35 USC 119 from Japanese Patent Application No. 2022-088987 filed on May 31, 2022, the disclosure of which is incorporated by reference herein.

BACKGROUND

1. Technical Field

The technology of the present disclosure relates to an information processing apparatus, an ultrasound endoscope, an information processing method, and a program.

2. Related Art

JP2011-000173A discloses an endoscopy support system that includes a first storage unit, a second storage unit, a setting unit, a generation unit, a calculation unit, a display unit, and a display control unit.

In the endoscopy support system disclosed in JP2011-000173A, the first storage unit stores volume data related to a luminal structure having a lesion part. The second storage unit stores data of an endoscope image related to the lesion part, which has been generated on the basis of an output from an endoscope inserted into the luminal structure. The setting unit sets a plurality of viewpoint positions in a predetermined region of the volume data. The generation unit generates data of a plurality of virtual endoscope images from the volume data on the basis of the plurality of set viewpoint positions. The calculation unit calculates a plurality of similarities between each of the plurality of generated virtual endoscope images and the endoscope image. The display unit displays the endoscope image and a specific virtual endoscope image which has a specific similarity among the plurality of calculated similarities side by side. In a case in which a lesion part region is included on the specific virtual endoscope image, the display control unit controls the display unit such that a partial region, which corresponds to the lesion part region, on the endoscope image is highlighted.

WO2019/088008A discloses an image processing device that includes a first image input unit, a second image input unit, an association unit, a first feature region extraction unit, a second feature region extraction unit, and a storage unit.

In the image processing device disclosed in WO2019/088008A, the first image input unit inputs a virtual endoscope image generated from a three-dimensional examination image of a subject. The second image input unit inputs an actual endoscope image obtained by imaging an observation target of the subject using an endoscope. The association unit associates the virtual endoscope image with the actual endoscope image. The first feature region extraction unit extracts a first feature region matched with a first condition from the virtual endoscope image. The second feature region extraction unit extracts a second feature region matched with a second condition corresponding to the first condition from the actual endoscope image. The storage unit stores at least one of information of a non-extracted region, which is associated with the second feature region of the actual endoscope image and is not extracted as the first feature region from the virtual endoscope image, or information of the second feature region associated with the non-extracted region.

SUMMARY

An embodiment according to the technology of the present disclosure provides an information processing apparatus, an ultrasound endoscope, an information processing method, and a program that can easily performing positioning between a medical module and a specific part.

According to a first aspect of the technology of the present disclosure, there is provided an information processing apparatus comprising a processor. The processor acquires an actual ultrasound image generated as an image showing an aspect of an observation target region including a specific part on the basis of reflected waves obtained by emitting ultrasonic waves from a medical module to the observation target region, acquires a virtual ultrasound image generated as an ultrasound image virtually showing the aspect of the observation target region on the basis of volume data indicating the observation target region, and specifies a positional relationship between a first position where the medical module is present and a second position where the specific part is present on the basis of the actual ultrasound image and the virtual ultrasound image.

According to a second aspect of the technology of the present disclosure, in the information processing apparatus according to the first aspect, the processor may compare the actual ultrasound image with the virtual ultrasound image to calculate an amount of deviation between the first position and the second position, and the positional relationship may be defined on the basis of the amount of deviation.

According to a third aspect of the technology of the present disclosure, in the information processing apparatus according to the first aspect or the second aspect, in a case in which the first position and the second position are matched with each other, the processor may perform a notification process of notifying that the first position and the second position are matched with each other.

According to a fourth aspect of the technology of the present disclosure, in the information processing apparatus according to any one of the first to third aspects, the processor may perform a first presentation process of presenting guidance information for guiding the first position to the second position on the basis of the positional relationship.

According to a fifth aspect of the technology of the present disclosure, in the information processing apparatus according to any one of the first to fourth aspects, the actual ultrasound image may be an ultrasound image generated in a Doppler mode.

According to a sixth aspect of the technology of the present disclosure, in the information processing apparatus according to any one of the first to fourth aspects, the actual ultrasound image may be an image that is based on an ultrasound image including a blood flow and on an ultrasound image in which intensity of the reflected waves is represented by brightness.

According to a seventh aspect of the technology of the present disclosure, in the information processing apparatus according to any one of the first to fourth aspects, the processor may acquire a first ultrasound image, which is an ultrasound image generated in a Doppler mode, and a second ultrasound image, which is an ultrasound image generated in a B-mode, as the actual ultrasound image. After presenting first guidance information for guiding the first position to another position on the basis of the first ultrasound image and the virtual ultrasound image, the processor may perform a second presentation process of presenting second guidance information for guiding the first position to the second position according to the positional relationship specified on the basis of the second ultrasound image and the virtual ultrasound image.

According to an eighth aspect of the technology of the present disclosure, in the information processing apparatus according to any one of the first to seventh aspects, the processor may display the actual ultrasound image on a display device.

According to a ninth aspect of the technology of the present disclosure, in the information processing apparatus according to the eighth aspect, the processor may perform an image recognition process on the actual ultrasound image and/or the virtual ultrasound image and display a result of the image recognition process on the display device.

According to a tenth aspect of the technology of the present disclosure, in the information processing apparatus according to the eighth aspect or the ninth aspect, the processor may display the virtual ultrasound image and the actual ultrasound image on the display device to be comparable with each other.

According to an eleventh aspect of the technology of the present disclosure, in the information processing apparatus according to the tenth aspect, the processor may select the virtual ultrasound image whose rate of match with the actual ultrasound image is equal to or greater than a predetermined value from a plurality of the virtual ultrasound images for different positions in the observation target region and display the selected virtual ultrasound image and the actual ultrasound image on the display device to be comparable with each other.

According to a twelfth aspect of the technology of the present disclosure, in the information processing apparatus according to any one of the eighth to eleventh aspects, the observation target region may include a luminal organ, and the processor may display a surface image, which is generated on the basis of the volume data and includes an inner surface of the luminal organ, and the actual ultrasound image on the display device to be comparable with each other.

According to a thirteenth aspect of the technology of the present disclosure, in the information processing apparatus according to the twelfth aspect, the surface image may be a video image that guides movement of the medical module.

According to a fourteenth aspect of the technology of the present disclosure, in the information processing apparatus according to the twelfth aspect or the thirteenth aspect, the processor may display, on the display device, position specification information capable of specifying a position which corresponds to a position where the ultrasonic waves are emitted from the medical module in the surface image.

According to a fifteenth aspect of the technology of the present disclosure, in the information processing apparatus according to the fourteenth aspect, the virtual ultrasound image may be a virtual ultrasound image showing an aspect of the observation target region for the position specified from the position specification information.

According to a sixteenth aspect of the technology of the present disclosure, in the information processing apparatus according to any one of the first to fifteenth aspects, the medical module may be a distal end part of an ultrasound endoscope having a treatment tool, and the specific part may be a treatment target part that is treated by the treatment tool.

According to a seventeenth aspect of the technology of the present disclosure, in the information processing apparatus according to the sixteenth aspect, the treatment tool may be a puncture needle, and the treatment target part may be a part that is punctured by the puncture needle.

According to an eighteenth aspect of the technology of the present disclosure, there is provided an ultrasound endoscope apparatus comprising: the information processing apparatus according to any one of the first to seventeenth aspects; and an ultrasound endoscope having the medical module provided in a distal end part thereof.

According to a nineteenth aspect of the technology of the present disclosure, there is provided an information processing method comprising: acquiring an actual ultrasound image generated as an image showing an aspect of an observation target region including a specific part on the basis of reflected waves obtained by emitting ultrasonic waves from a medical module to the observation target region; acquiring a virtual ultrasound image generated as an ultrasound image virtually showing the aspect of the observation target region on the basis of volume data indicating the observation target region; and specifying a positional relationship between a first position where the medical module is present and a second position where the specific part is present on the basis of the actual ultrasound image and the virtual ultrasound image.

According to a twentieth aspect of the technology of the present disclosure, there is provided a program that causes a computer to execute a process comprising: acquiring an actual ultrasound image generated as an image showing an aspect of an observation target region including a specific part on the basis of reflected waves obtained by emitting ultrasonic waves from a medical module to the observation target region; acquiring a virtual ultrasound image generated as an ultrasound image virtually showing the aspect of the observation target region on the basis of volume data indicating the observation target region; and specifying a positional relationship between a first position where the medical module is present and a second position where the specific part is present on the basis of the actual ultrasound image and the virtual ultrasound image.

BRIEF DESCRIPTION OF THE DRAWINGS

Exemplary embodiments of the technology of the disclosure will be described in detail based on the following figures, wherein.

DETAILED DESCRIPTION

Hereinafter, examples of embodiments of an information processing apparatus, a bronchoscope apparatus, an information processing method, and a program according to the technology of the present disclosure will be described with reference to the accompanying drawings.

First, terms used in the following description will be described.

CPU is an abbreviation of "central processing unit". GPU is an abbreviation of "graphics processing unit". RAM is an abbreviation of "random access memory". NVM is an abbreviation of "non-volatile memory". EEPROM is an abbreviation of "electrically erasable programmable read-only memory". ASIC is an abbreviation of "application specific integrated circuit". PLD is an abbreviation of "programmable logic device". FPGA is an abbreviation of "field-programmable gate array". SoC is an abbreviation of "system-on-a-chip". SSD is an abbreviation of "solid state drive". USB is an abbreviation of "universal serial bus". HDD is an abbreviation of "hard disk drive". EL is an abbreviation of "electro-luminescence". CMOS is an abbreviation of "complementary metal oxide semiconductor". CCD is an abbreviation of "charge-coupled device". CT is an abbreviation of "computed tomography". MRI is an abbreviation of "magnetic resonance imaging". PC is an abbreviation of "personal computer". LAN is an abbreviation of "local area network". WAN is an abbreviation of "wide area network". AI is an abbreviation of "artificial intelligence". ADC is an abbreviation of "analog-to-digital converter". FPC is an abbreviation of "flexible printed circuit". BLI is an abbreviation of "blue laser imaging". LCI is an abbreviation of "linked color imaging". In this embodiment, the term "match" means match including an error that is generally allowed in the technical field to which the technology of the present disclosure belongs and that does not deviate from the gist of the technology of the present disclosure, in addition to perfect match.

Figure 1:
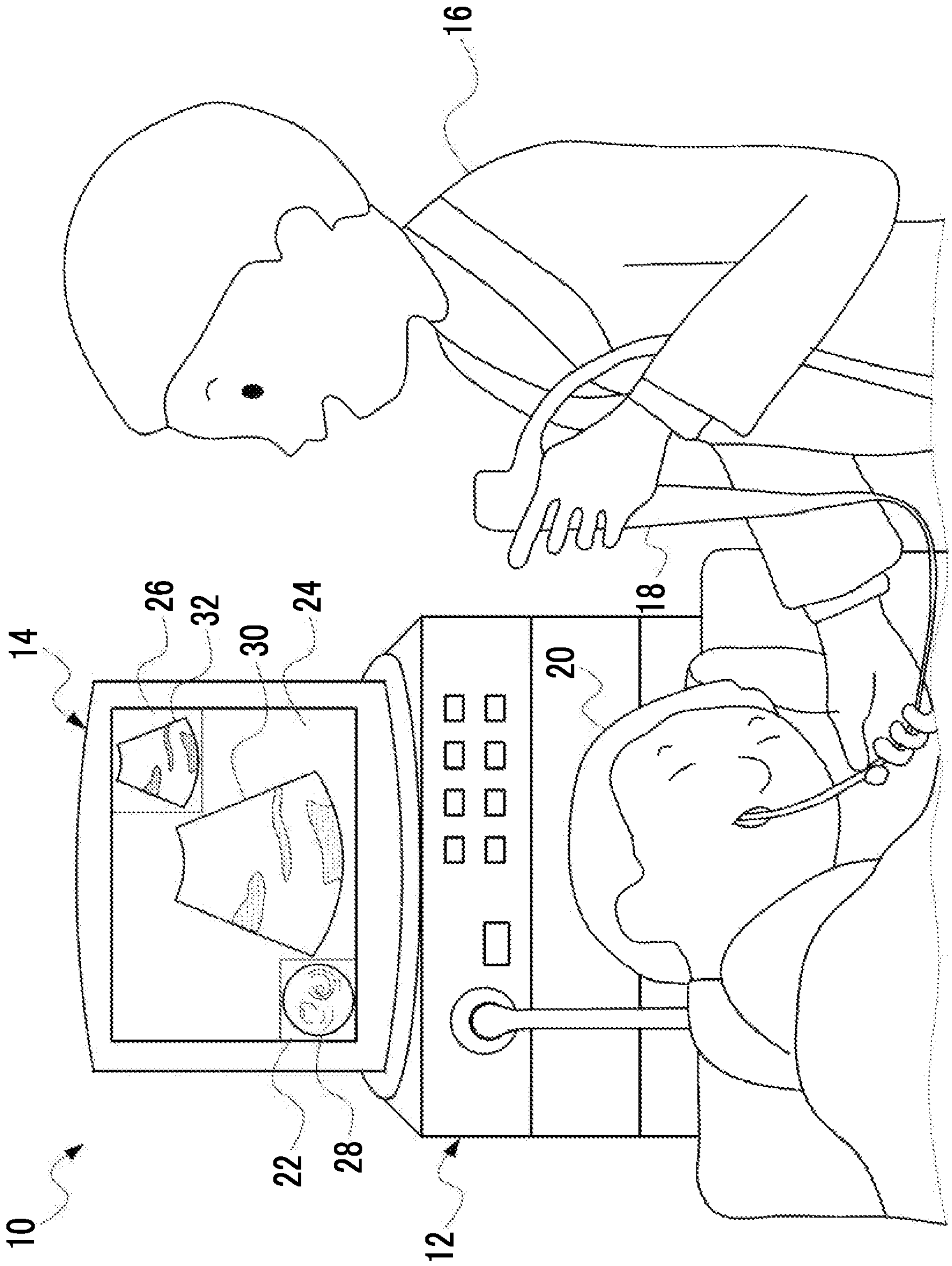
FIG. 1 is a conceptual diagram illustrating an example of an aspect in which an endoscope system is used.

For example, as illustrated in FIG. 1, an endoscope system 10 comprises an ultrasound endoscope apparatus 12. The ultrasound endoscope apparatus 12 is an example of an "ultrasound endoscope apparatus" according to the technology of the present disclosure. The ultrasound endoscope apparatus 12 has a display device 14. The ultrasound endoscope apparatus 12 is used by a medical worker (hereinafter, referred to as a "user") such as a doctor 16. The ultrasound endoscope apparatus 12 comprises a bronchoscope 18 (endoscope) and is used to perform a medical treatment on a respiratory system including bronchi of a subject 20 (for example, a patient) through the bronchoscope 18. The bronchoscope 18 is an example of an "ultrasound endoscope" according to the technology of the present disclosure. The display device 14 is an example of a "display device" according to the technology of the present disclosure.

The bronchoscope 18 is inserted into the bronchus of the subject 20 by the doctor 16, images the inside of the bronchus, acquires an image showing an aspect of the inside of the bronchus, and outputs the image. In the example illustrated in FIG. 1, an aspect in which the bronchoscope 18 is inserted into a luminal organ of the respiratory system through a mouth of the subject 20 is illustrated. In addition, in the example illustrated in FIG. 1, the bronchoscope 18 is inserted into the luminal organ of the respiratory system through the mouth of the subject 20. However, this is only an example, and the bronchoscope 18 may be inserted into the luminal organ of the respiratory system through a nose of the subject 20. Further, in this embodiment, the luminal organ of the respiratory system means an organ forming an air passage from an upper airway to a lower airway (for example, an organ including a trachea and the bronchus).

Hereinafter, the luminal organ of the respiratory system is simply referred to as a "luminal organ".

The display device 14 displays various types of information including an image. Examples of the display device 14 include a liquid crystal display and an EL display. A plurality of screens are displayed side by side on the display device 14. In the example illustrated in FIG. 1, screens 22, 24, and 26 are given as an example of the plurality of screens.

An endoscope image 28 captured by an optical method is displayed on the screen 22. The endoscope image 28 is an image obtained by emitting light (for example, visible light or infrared light) to an inner surface of the luminal organ (for example, the bronchus) (hereinafter, also referred to as a "luminal organ inner wall surface") of the subject 20 with the bronchoscope 18 and capturing reflected light from the luminal organ inner wall surface. An example of the endoscope image 28 is a video image (for example, a live view image). However, this is only an example, and the endoscope image 28 may be a still image.

An actual ultrasound image 30 showing an aspect of an observation target region on a back side of the luminal organ inner wall surface (hereinafter, also simply referred to as an "observation target region") is displayed on the screen 24. The actual ultrasound image 30 is an ultrasound image generated on the basis of reflected waves obtained by the reflection of ultrasonic waves, which have been emitted to the observation target region by the bronchoscope 18 through the luminal organ inner wall surface in the luminal organ, from the observation target region. The actual ultrasound image 30 is an ultrasound image that is actually obtained under a so-called brightness (B)-mode. In addition, here, the ultrasound image actually obtained in the B-mode is given as an example of the actual ultrasound image 30. However, the technology of the present disclosure is not limited thereto, and the actual ultrasound image 30 may be an ultrasound image that is actually obtained in a so-called motion (M)-mode or a Doppler mode. The actual ultrasound image 30 is an example of an "actual ultrasound image" according to the technology of the present disclosure.

A virtual ultrasound image 32 is displayed on the screen 26. That is, the actual ultrasound image 30 and the virtual ultrasound image 32 are displayed on the display device 14 to be comparable with each other. As described in detail below, the virtual ultrasound image 32 is a virtual ultrasound image showing the aspect of the observation target region and is referred to by the user. The virtual ultrasound image 32 is an example of a "virtual ultrasound image" according to the technology of the present disclosure.

Figure 2:
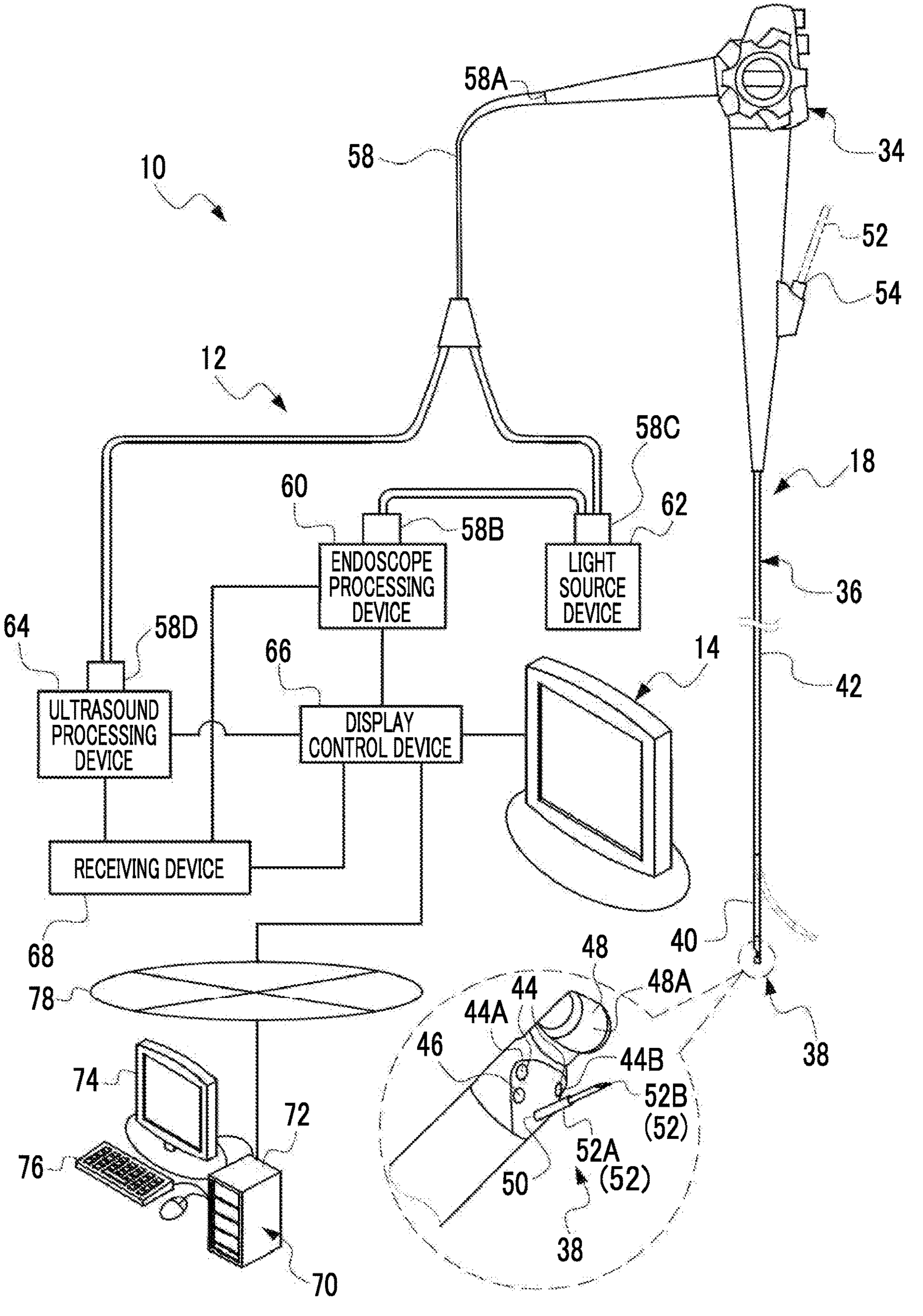
FIG. 2 is a conceptual diagram illustrating an example of an overall configuration of the endoscope system.

For example, as illustrated in FIG. 2, the bronchoscope 18 comprises an operation unit 34 and an insertion portion 36. The insertion portion 36 is formed in a tubular shape. The insertion portion 36 has a distal end part 38, a bendable part 40, and a soft part 42. The distal end part 38, the bendable part 40, and the soft part 42 are disposed in the order of the distal end part 38, the bendable part 40, and the soft part 42 from a distal end to a base end of the insertion portion 36. The soft part 42 is made of an elongated flexible material and connects the operation unit 34 and the bendable part 40. The bendable part 40 is partially bent or is rotated about an axis of the insertion portion 36 by the operation of the operation unit 34. As a result, the insertion portion 36 is moved to the back side of the luminal organ while being bent according to the shape of the luminal organ (for example, the shape of a bronchial tube) or while being rotated about the axis of the insertion portion 36.

The distal end part 38 is provided with an illumination device 44, a camera 46, an ultrasound probe 48, and a treatment tool opening 50. The illumination device 44 has an illumination window 44A and an illumination window 44B. The illumination device 44 emits light through the illumination window 44A and the illumination window 44B. Examples of the type of light emitted from the illumination device 44 include visible light (for example, white light), invisible light (for example, near-infrared light), and/or special light. Examples of the special light include light for BLI and/or light for LCI. The camera 46 images the inside of the luminal organ using the optical method. An example of the camera 46 is a CMOS camera. The CMOS camera is only an example, and the camera 46 may be other types of cameras such as CCD cameras.

The ultrasound probe 48 is provided on a distal end side of the distal end part 38. An outer surface 48A of the ultrasound probe 48 is bent outward in a convex shape from a base end to a distal end of the ultrasound probe 48. The ultrasound probe 48 transmits ultrasonic waves through the outer surface 48A and receives reflected waves obtained by the reflection of the transmitted ultrasonic waves from the observation target region through the outer surface 48A. In addition, here, the transmission of the ultrasonic waves is an example of "emission of ultrasonic waves" according to the technology of the present disclosure.

The treatment tool opening 50 is formed closer to a base end of the distal end part 38 than the ultrasound probe 48 is. The treatment tool opening 50 is an opening through which a treatment tool 52 protrudes from the distal end part 38. A treatment tool insertion opening 54 is formed in the operation unit 34, and the treatment tool 52 is inserted into the insertion portion 36 through the treatment tool insertion opening 54. The treatment tool 52 passes through the insertion portion 36 and protrudes from the treatment tool opening 50 to the inside of the body. In the example illustrated in FIG. 2, as the treatment tool 52, a sheath 52A protrudes from the treatment tool opening 50. The sheath 52A is inserted into the insertion portion 36 through the treatment tool insertion opening 54 and protrudes from the treatment tool opening 50 to the outside. Further, in the example illustrated in FIG. 2, a puncture needle 52B is also illustrated as the treatment tool 52. The puncture needle 52B is inserted into the sheath 52A and protrudes from a distal end of the sheath 52A to the outside. Here, the sheath 52A and the puncture needle 52B are given as an example of the treatment tool 52. However, this is only an example, and the treatment tool 52 may be, for example, grasping forceps and/or an ultrasound probe. These tools may be inserted into the sheath 52A and then used. In addition, the treatment tool opening 50 also functions as a suction opening for drawing, for example, blood and body waste.

The ultrasound endoscope apparatus 12 comprises a universal cord 58, an endoscope processing device 60, a light source device 62, an ultrasound processing device 64, and a display control device 66. The universal cord 58 has a base end part 58A and first to third distal end parts 58B to 58D. The base end part 58A is connected to the operation unit 34. The first distal end part 58B is connected to the endoscope processing device 60. The second distal end part 58C is connected to the light source device 62. The third distal end part 58D is connected to the ultrasound processing device 64.

The endoscope system 10 comprises a receiving device 68. The receiving device 68 receives an instruction from the user. Examples of the receiving device 68 include an operation panel having a plurality of hard keys and/or a touch panel, a keyboard, a mouse, a track ball, a foot switch, a smart device, and/or a microphone.

The receiving device 68 is connected to the endoscope processing device 60. The endoscope processing device 60 transmits and receives various signals to and from the camera 46 or controls the light source device 62 according to the instruction received by the receiving device 68. The endoscope processing device 60 directs the camera 46 to perform imaging, acquires the endoscope image 28 (see FIG. 1) from the camera 46, and outputs the endoscope image 28. The light source device 62 emits light under the control of the endoscope processing device 60 and supplies the light to the illumination device 44. A light guide is provided in the illumination device 44, and the light supplied from the light source device 62 is emitted from the illumination windows 44A and 44B via the light guide.

The receiving device 68 is connected to the ultrasound processing device 64. The ultrasound processing device 64 transmits and receives various signals to and from the ultrasound probe 48 according to the instruction received by the receiving device 68. The ultrasound processing device 64 directs the ultrasound probe 48 to transmit the ultrasonic waves, generates the actual ultrasound image 30 (see FIG. 1) on the basis of the reflected waves received by the ultrasound probe 48, and outputs the actual ultrasound image 30.

The display device 14, the endoscope processing device 60, the ultrasound processing device 64, and the receiving device 68 are connected to the display control device 66. The display control device 66 controls the display device 14 according to the instruction received by the receiving device 68. The display control device 66 acquires the endoscope image 28 from the endoscope processing device 60 and displays the acquired endoscope image 28 on the display device 14 (see FIG. 1). In addition, the display control device 66 acquires the actual ultrasound image 30 from the ultrasound processing device 64 and displays the acquired actual ultrasound image 30 on the display device 14 (see FIG. 1).

The endoscope system 10 comprises a server 70. An example of the server 70 is a server for a cloud service. The server 70 includes a computer 72 which is a main body of the server 70, a display device 74, and a receiving device 76. The computer 72 and the display control device 66 are connected through a network 78 such that they can communicate with each other. An example of the network 78 is a LAN. In addition, the LAN is only an example, and the network 78 may be configured by, for example, at least one of the LAN or a WAN.

The display control device 66 is positioned as a client terminal for the server 70. Therefore, the server 70 performs a process corresponding to a request given from the display control device 66 through the network 78 and provides a processing result to the display control device 66 through the network 78.

The display device 74 and the receiving device 76 are connected to the computer 72. The display device 74 displays various types of information under the control of the computer 72. Examples of the display device 74 include a liquid crystal display and an EL display. The receiving device 76 receives an instruction from, for example, the user of the server 70. Examples of the receiving device 76 include a keyboard and a mouse. The computer 72 performs a process corresponding to the instruction received by the receiving device 76.

Figure 3:
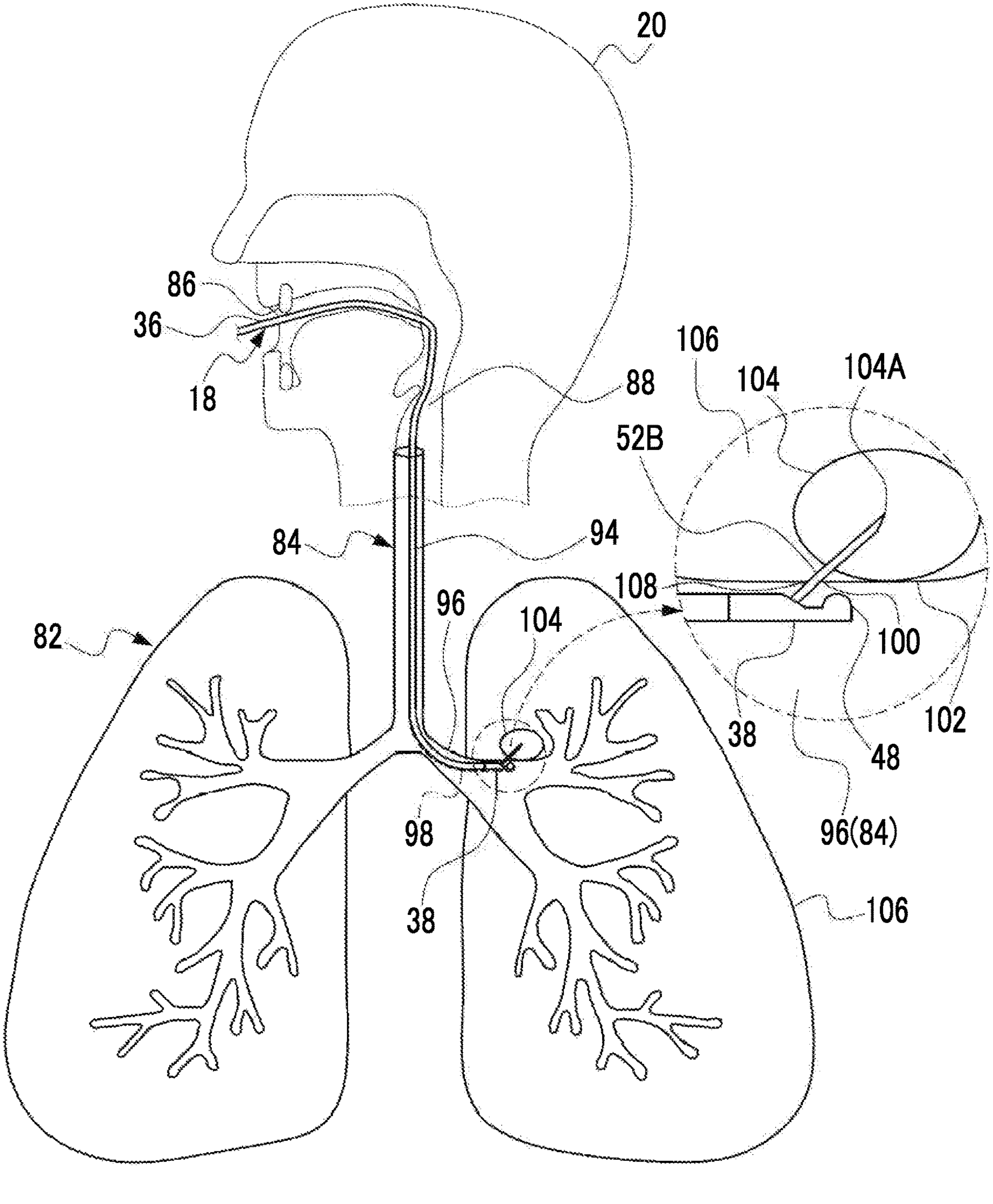
FIG. 3 is a conceptual diagram illustrating an example of an aspect in which an insertion portion of a bronchoscope is inserted into a luminal organ of a subject.

For example, as illustrated in FIG. 3, a respiratory organ 82 is included in the body of the subject 20. The respiratory organ 82 has a luminal organ 84 such as the upper airway and the lower airway. The insertion portion 36 of the bronchoscope 18 is inserted into the luminal organ 84 from an oral cavity 86 of the subject 20. That is, the insertion portion 36 is inserted into a bronchus 96 from the oral cavity 86 through a larynx 88. The distal end part 38 is moved to a back side of the bronchus 96 along a predetermined route 98 in the bronchus 96. The distal end part 38 moved to the back side of the bronchus 96 eventually reaches a predetermined position 100 in the bronchus 96.

The position 100 is the position of a portion of a luminal organ inner wall surface 102 which is an inner surface of the luminal organ 84. Specifically, the position 100 is a position where a lymph node 104 designated in advance as a treatment target part to be treated by the treatment tool 52 is present outside the luminal organ 84 (in the example illustrated in FIG. 3, the bronchus 96) in the luminal organ inner wall surface 102. In other words, the position 100 means a position where the lymph node 104 is immanent in the luminal organ inner wall surface 102. In this embodiment, the lymph node 104 is a part from which tissues are to be collected. That is, the lymph node 104 is a part to be punctured by the puncture needle 52B. In the example illustrated in FIG. 3, the position 100 is a position where the luminal organ inner wall surface 102 is punctured by the puncture needle 52B in a case in which a central portion 104A (for example, the center) of the lymph node 104 is pricked by the puncture needle 52B.

The ultrasound probe 48 in the distal end part 38 of the bronchoscope 18 emits the ultrasonic waves to an observation target region 106 including the luminal organ 84 and the lymph node 104 (for example, an organ such as a lung including the luminal organ 84 and the lymph node 104). Then, the actual ultrasound image 30 is generated on the basis of the reflected waves obtained by the reflection of the emitted ultrasonic waves from the observation target region 106. In addition, the aspect of the observation target region 106 punctured by the puncture needle 52B is shown by the actual ultrasound image 30. In the example illustrated in FIG. 3, a position 108 of the distal end part 38 of the bronchoscope 18 is matched with the position 100. The position 108 is a position facing the position where the puncture needle 52B in the treatment tool opening 50 (see FIG. 2) protrudes in the luminal organ inner wall surface 102. In other words, the position 108 is a position where a protruding direction of the puncture needle 52B and the luminal organ inner wall surface 102 intersect each other.

The lymph node 104 is an example of a "specific part" and a "treatment target part" according to the technology of the present disclosure. The treatment tool 52 is an example of a "treatment tool" according to the technology of the present disclosure. The puncture needle 52B is an example of a "puncture needle" according to the technology of the present disclosure. The distal end part 38 is an example of a "medical module" and a "distal end part of an ultrasound endoscope" according to the technology of the present disclosure. The observation target region 106 is an example of an "observation target region" according to the technology of the present disclosure. The position 108 is an example of a "first position" according to the technology of the present disclosure. The position 100 is an example of a "second position" according to the technology of the present disclosure.

Figure 4:
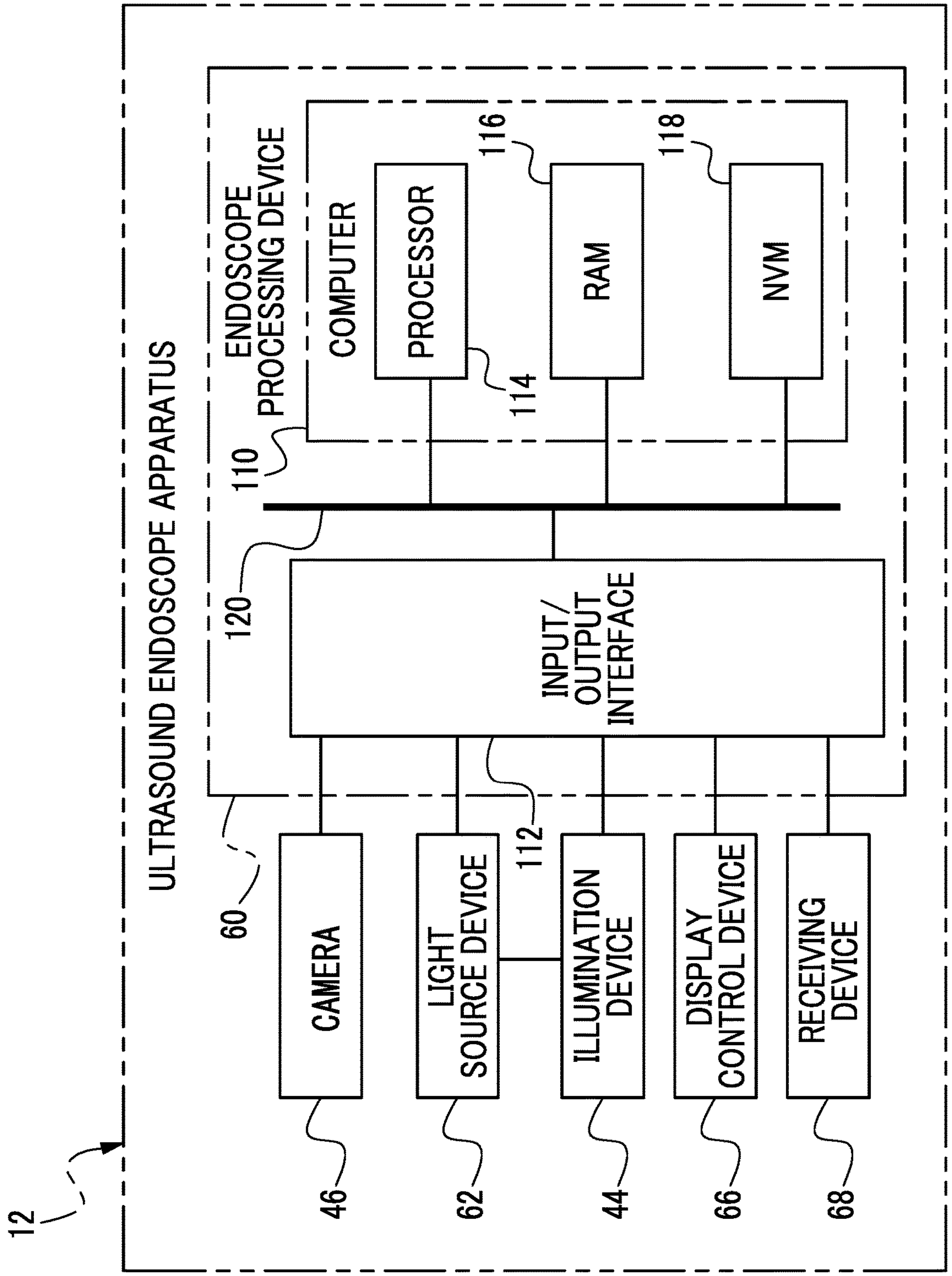
FIG. 4 is a block diagram illustrating an example of a hardware configuration of an endoscope processing device.

For example, as illustrated in FIG. 4, the endoscope processing device 60 comprises a computer 110 and an input/output interface 112. The computer 110 comprises a processor 114, a RAM 116, and an NVM 118. The input/output interface 112, the processor 114, the RAM 116, and the NVM 118 are connected to a bus 120.

For example, the processor 114 has a CPU and a GPU and controls the entire endoscope processing device 60. The GPU operates under the control of the CPU and mainly performs image processing. In addition, the processor 114 may be one or more CPUs with which the functions of the GPU have been integrated or may be one or more CPUs with which the functions of the GPU have not been integrated.

The RAM 116 is a memory that temporarily stores information and is used as a work memory by the processor 114. The NVM 118 is a non-volatile storage device that stores, for example, various programs and various parameters. An example of the NVM 118 is a flash memory (for example, an EEPROM) and/or an SSD. In addition, the flash memory and the SSD are only an example, and the NVM 118 may be other non-volatile storage devices, such as HDDs, or may be a combination of two or more types of non-volatile storage devices.

The receiving device 68 is connected to the input/output interface 112, and the processor 114 acquires the instruction received by the receiving device 68 through the input/output interface 112 and performs a process corresponding to the acquired instruction. In addition, the camera 46 is connected to the input/output interface 112. The processor 114 controls the camera 46 through the input/output interface 112 or acquires the endoscope image 28 obtained by imaging the inside of the body of the subject 20 with the camera 46 through the input/output interface 112. Further, the light source device 62 is connected to the input/output interface 112. The processor 114 controls the light source device 62 through the input/output interface 112 such that light is supplied to the illumination device 44 or the amount of light supplied to the illumination device 44 is adjusted. In addition, the display control device 66 is connected to the input/output interface 112. The processor 114 transmits and receives various signals to and from the display control device 66 through the input/output interface 112.

Figure 5:
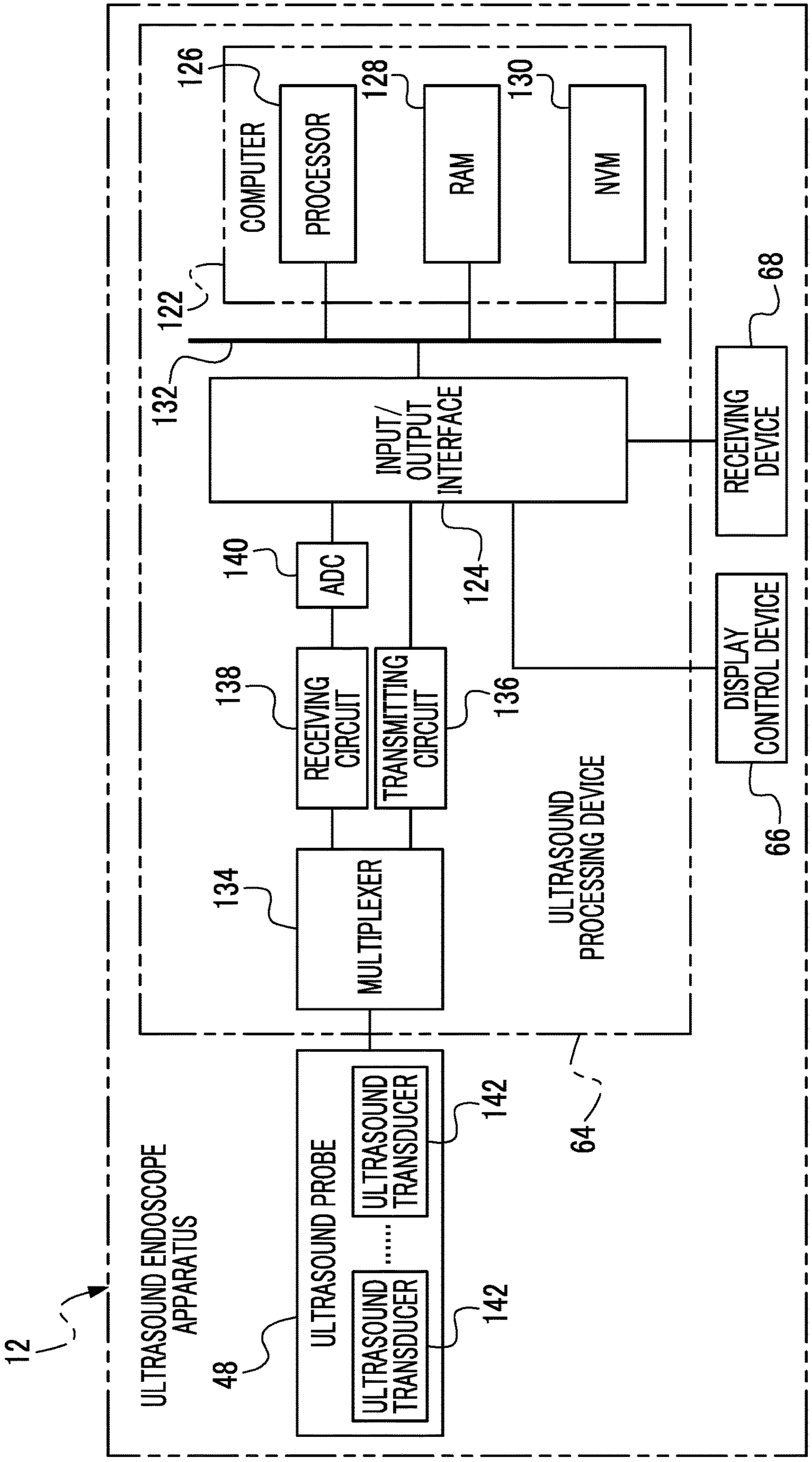
FIG. 5 is a block diagram illustrating an example of a hardware configuration of an ultrasound processing device.

For example, as illustrated in FIG. 5, the ultrasound processing device 64 comprises a computer 122 and an input/output interface 124. The computer 122 comprises a processor 126, a RAM 128, and an NVM 130. The input/output interface 124, the processor 126, the RAM 128, and the NVM 130 are connected to a bus 132. The processor 126 controls the entire ultrasound processing device 64. In addition, a plurality of hardware resources (that is, the processor 126, the RAM 128, and the NVM 130) included in the computer 122 illustrated in FIG. 5 are the same types as a plurality of hardware resources included in the computer 110 illustrated in FIG. 4. Therefore, the description thereof will not be repeated here.

The receiving device 68 is connected to the input/output interface 124, and the processor 126 acquires the instruction received by the receiving device 68 through the input/output interface 124 and performs a process corresponding to the acquired instruction. In addition, the display control device 66 is connected to the input/output interface 124. The processor 126 transmits and receives various signals to and from the display control device 66 through the input/output interface 124.

The ultrasound processing device 64 comprises a multiplexer 134, a transmitting circuit 136, a receiving circuit 138, and an analog-digital converter 140 (hereinafter, referred to as an "ADC 140"). The multiplexer 134 is connected to the ultrasound probe 48. An input end of the transmitting circuit 136 is connected to the input/output interface 124, and an output end of the transmitting circuit 136 is connected to the multiplexer 134. An input end of the ADC 140 is connected to an output end of the receiving circuit 138, and an output end of the ADC 140 is connected to the input/output interface 124. An input end of the receiving circuit 138 is connected to the multiplexer 134.

The ultrasound probe 48 comprises a plurality of ultrasound transducers 142. The plurality of ultrasound transducers 142 are arranged in a one-dimensional or two-dimensional array to be unitized. Each of the plurality of ultrasound transducers 142 is formed by disposing electrodes on both surfaces of a piezoelectric element. An example of the piezoelectric element is barium titanate, lead zirconate titanate, or potassium niobate. The electrodes consist of individual electrodes that are individually provided for the plurality of ultrasound transducers 142 and a transducer ground that is common to the plurality of ultrasound transducers 142. The electrodes are electrically connected to the ultrasound processing device 64 through an FPC and a coaxial cable.

The ultrasound probe 48 is a convex array probe in which the plurality of ultrasound transducers 142 are disposed in an arc shape. The plurality of ultrasound transducers 142 are arranged along the outer surface 48A (see FIG. 2). That is, the plurality of ultrasound transducers 142 are arranged at equal intervals in a convex curvature shape along an axial direction of the distal end part 38 (see FIG. 2) (that is, a longitudinal axis direction of the insertion portion 36). Therefore, the ultrasound probe 48 operates the plurality of ultrasound transducers 142 to radially transmit the ultrasonic waves. In addition, the convex array probe is given as an example here. However, this is only an example, and the ultrasound probe 48 may be, for example, a radial probe, a linear probe, or a sector probe. Further, a scanning method of the ultrasound probe 48 is not particularly limited.

The transmitting circuit 136 and the receiving circuit 138 are electrically connected to each of the plurality of ultrasound transducers 142 through the multiplexer 134. The multiplexer 134 selects at least one of the plurality of ultrasound transducers 142 and opens a channel of a selected ultrasound transducer which is the selected ultrasound transducer 142.

The transmitting circuit 136 is controlled by the processor 126 through the input/output interface 124. The transmitting circuit 136 supplies a driving signal for transmitting the ultrasonic waves (for example, a plurality of pulsed signals) to the selected ultrasound transducer under the control of the processor 126. The driving signal is generated according to transmission parameters set by the processor 126. The transmission parameters are, for example, the number of driving signals supplied to the selected ultrasound transducer, the supply time of the driving signals, and a driving vibration amplitude.

The transmitting circuit 136 supplies the driving signal to the selected ultrasound transducer such that the selected ultrasound transducer transmits the ultrasonic waves. That is, in a case in which the driving signal is supplied to the electrode included in the selected ultrasound transducer, the piezoelectric element included in the selected ultrasound transducer is expanded and contracted, and the selected ultrasound transducer vibrates. As a result, pulsed ultrasonic waves are output from the selected ultrasound transducer. The output intensity of the selected ultrasound transducer is defined by the amplitude of the ultrasonic waves output from the selected ultrasound transducer (that is, the magnitude of ultrasound pressure).

The ultrasound transducer 142 receives the reflected waves obtained by the reflection of the transmitted ultrasonic waves from the observation target region 106. The ultrasound transducer 142 outputs an electric signal indicating the received reflected waves to the receiving circuit 138 through the multiplexer 134. Specifically, the piezoelectric element included in the ultrasound transducer 142 outputs the electric signal. The receiving circuit 138 receives the electric signal from the ultrasound transducer 142, amplifies the received electric signal, and outputs the amplified electric signal to the ADC 140. The ADC 140 digitizes the electric signal input from the receiving circuit 138. The processor 126 acquires the electric signal digitized by the ADC 140 and generates the actual ultrasound image 30 (see FIG. 1) on the basis of the acquired electric signal.

Figure 6:
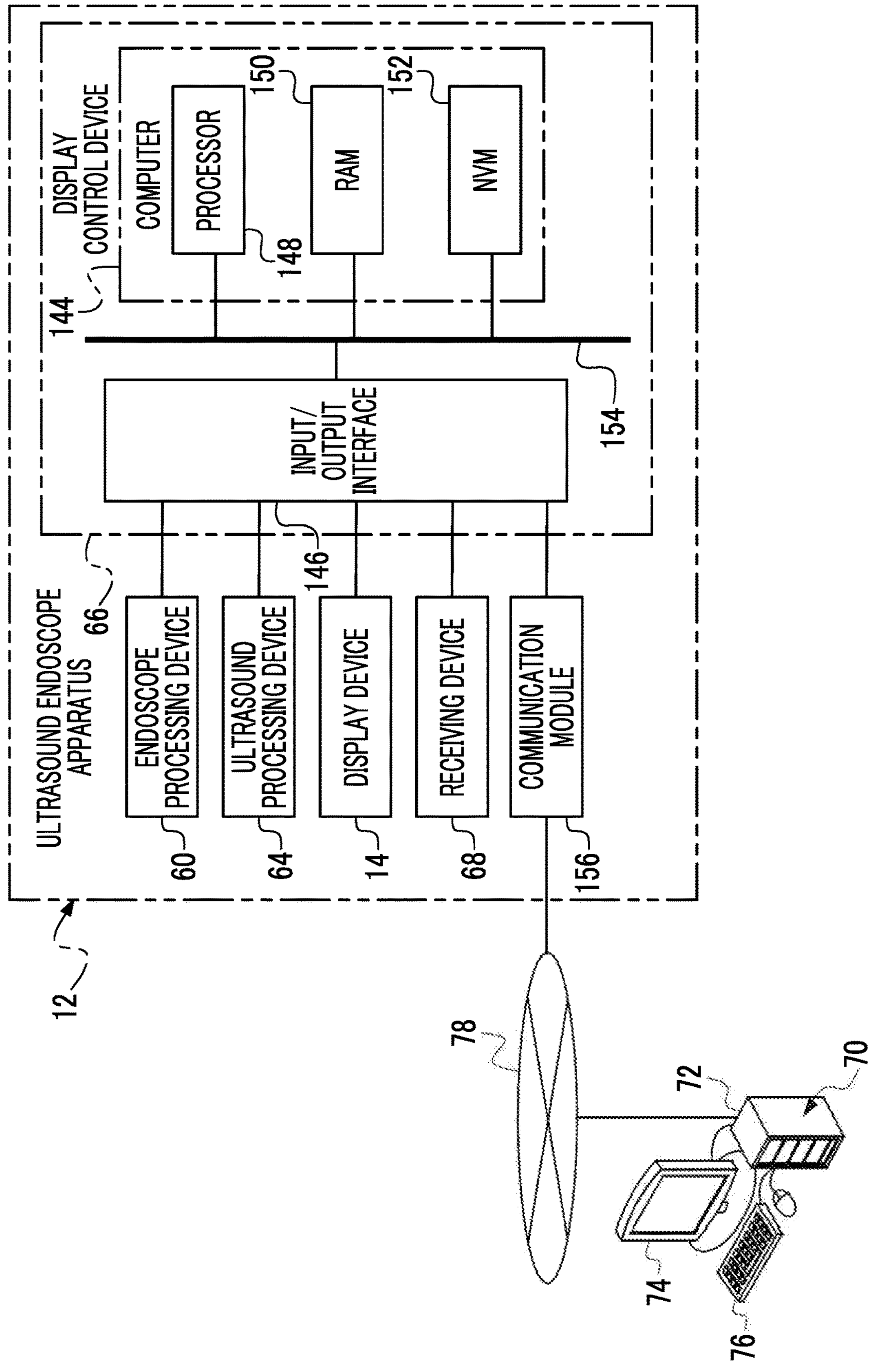
FIG. 6 is a block diagram illustrating an example of a hardware configuration of a display control device.

For example, as illustrated in FIG. 6, the display control device 66 comprises a computer 144 and an input/output interface 146. The computer 144 comprises a processor 148, a RAM 150, and an NVM 152. The input/output interface 146, the processor 148, the RAM 150, and the NVM 152 are connected to a bus 154.

The processor 148 controls the entire display control device 66. In addition, a plurality of hardware resources (that is, the processor 148, the RAM 150, and the NVM 152) included in the computer 144 illustrated in FIG. 6 are the same types as the plurality of hardware resources included in the computer 110 illustrated in FIG. 4. Therefore, the description thereof will not be repeated here.

The receiving device 68 is connected to the input/output interface 146, and the processor 148 acquires the instruction received by the receiving device 68 through the input/output interface 146 and performs a process corresponding to the acquired instruction. In addition, the endoscope processing device 60 is connected to the input/output interface 146, and the processor 148 transmits and receives various signals to and from the processor 114 (see FIG. 4) of the endoscope processing device 60 through the input/output interface 146. Further, the ultrasound processing device 64 is connected to the input/output interface 146, and the processor 148 transmits and receives various signals to and from the processor 126 (see FIG. 5) of the ultrasound processing device 64 through the input/output interface 146.

The display device 14 is connected to the input/output interface 146, and the processor 148 controls the display device 14 through the input/output interface 146 such that various types of information are displayed on the display device 14. For example, the processor 148 acquires the endoscope image 28 (see FIG. 1) from the endoscope processing device 60, acquires the actual ultrasound image 30 (see FIG. 1) from the ultrasound processing device 64, and displays the endoscope image 28 and the actual ultrasound image 30 on the display device 14.

The ultrasound endoscope apparatus 12 comprises a communication module 156. The communication module 156 is connected to the input/output interface 146. The communication module 156 is an interface including a communication processor, an antenna, and the like. The communication module 156 is connected to the network 78 and controls communication between the processor 148 and the computer 72 of the server 70.

Figure 7:
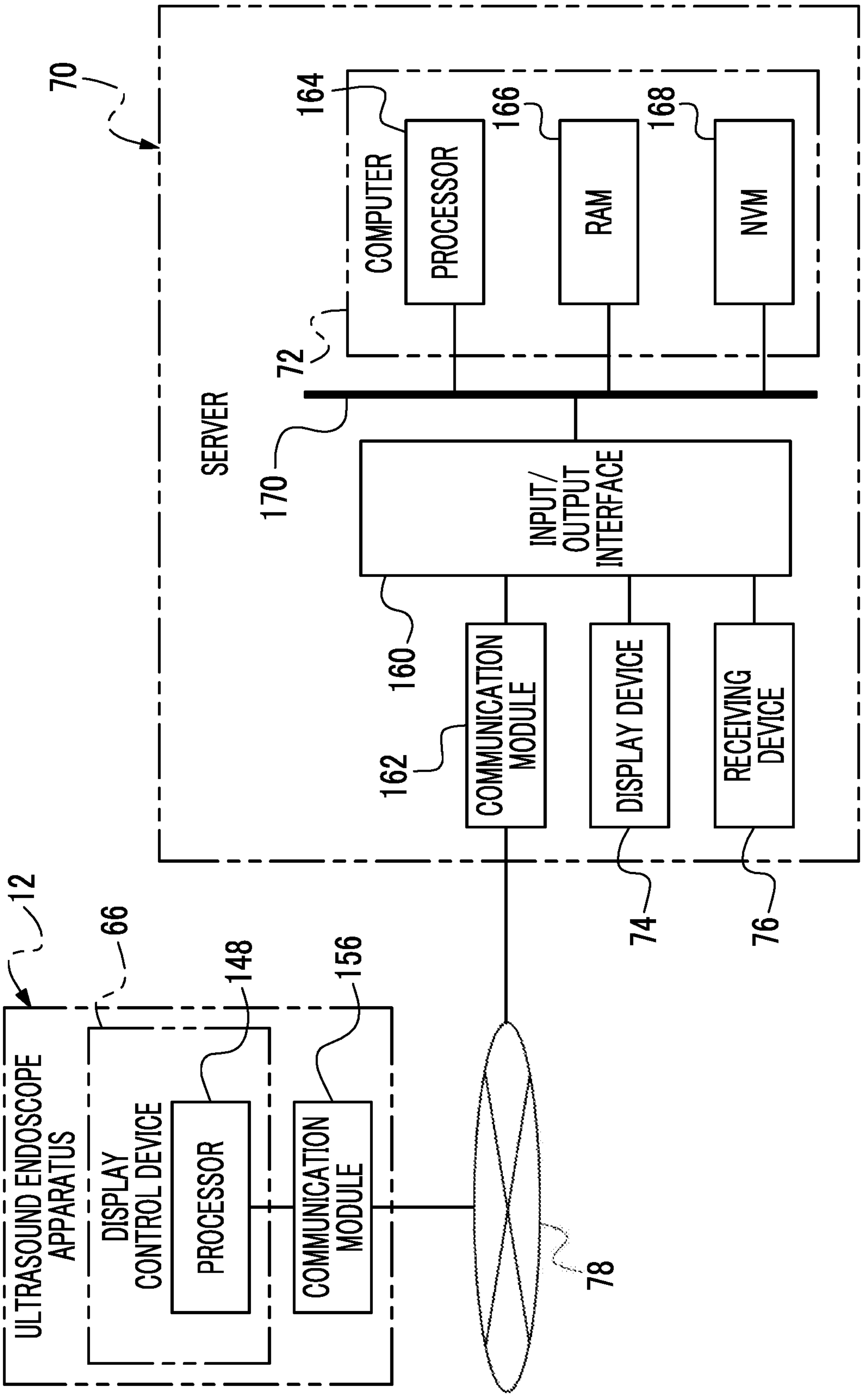
FIG. 7 is a block diagram illustrating an example of a hardware configuration of a server.

For example, as illustrated in FIG. 7, the server 70 comprises an input/output interface 160 that is the same as the input/output interface 112 (see FIG. 4) and a communication module 162 that is the same as the communication module 156 in addition to the computer 72, the display device 74, and the receiving device 76. The computer 72 comprises a processor 164 that is the same as the processor 148 (see FIG. 6), a RAM 166 that is the same as the RAM 150 (see FIG. 6), and an NVM 168 that is the same as the NVM 152 (see FIG. 6). The input/output interface 160, the processor 164, the RAM 166, and the NVM 168 are connected to a bus 170.

The display device 74 is connected to the input/output interface 160, and the processor 164 controls the display device 74 through the input/output interface 160 such that various types of information are displayed on the display device 74.

The receiving device 76 is connected to the input/output interface 160, and the processor 164 acquires the instruction received by the receiving device 76 through the input/output interface 160 and performs a process corresponding to the acquired instruction.

The communication module 162 is connected to the input/output interface 160. The communication module 162 is connected to the network 78 and performs communication between the processor 164 of the server 70 and the processor 148 of the display control device 66 in cooperation with the communication module 156.

In addition, the display control device 66 and the server 70 are an example of an "information processing apparatus" according to the technology of the present disclosure. In addition, the processors 148 and 164 are an example of a "processor" according to the technology of the present disclosure. The computer 144 (see FIG. 6) and the computer 72 are an example of a "computer" according to the technology of the present disclosure.

However, in a case in which a treatment (for example, tissue collection) is performed on the lymph node 104 using the treatment tool 52, the doctor 16 refers to the endoscope image 28 and/or the actual ultrasound image 30 displayed on the display device 14. Then, the doctor 16 operates the bronchoscope 18 to align the position 100 (see FIG. 3) with the position 108 (see FIG. 3) while referring to the endoscope image 28 and/or the actual ultrasound image 30 displayed on the display device 14. In a case in which the position alignment is successful, the doctor 16 performs the treatment on the lymph node 104 using the treatment tool 52. However, even in a case in which the doctor 16 refers to the endoscope image 28 and/or the actual ultrasound image 30 displayed on the display device 14, it is difficult for the doctor 16 to ascertain the positional relationship between the position 100 and the position 108. It is important for the doctor 16 to ascertain the positional relationship between the position 100 and the position 108 in order to accurately perform the treatment on the lymph node 104. In addition, it is important for the doctor 16 to ascertain the positional relationship between the position 100 and the position 108 in order to shorten the time until the start of the treatment on the lymph node 104. The more the time until the start of the treatment on the lymph node 104 is shortened, the more the time required for the insertion portion 36 to be inserted into the luminal organ 84 can be shortened. As a result, the burden on the body of the subject 20 is also reduced.

Therefore, in view of these circumstances, in this embodiment, the processor 148 of the display control device 66 performs display-control-device-side processes, and the processor 164 of the server 70 performs server-side processes. The display-control-device-side processes include an endoscope image display process, a navigation video image display process, an actual ultrasound image display process, a virtual ultrasound image display process, and a support information display process (see FIG. 8 and FIGS. 21 to 25). The server-side processes include a navigation video image generation process, a virtual ultrasound image generation process, and a support information generation process (see FIG. 9 and FIGS. 26 to 28).

Figure 8:
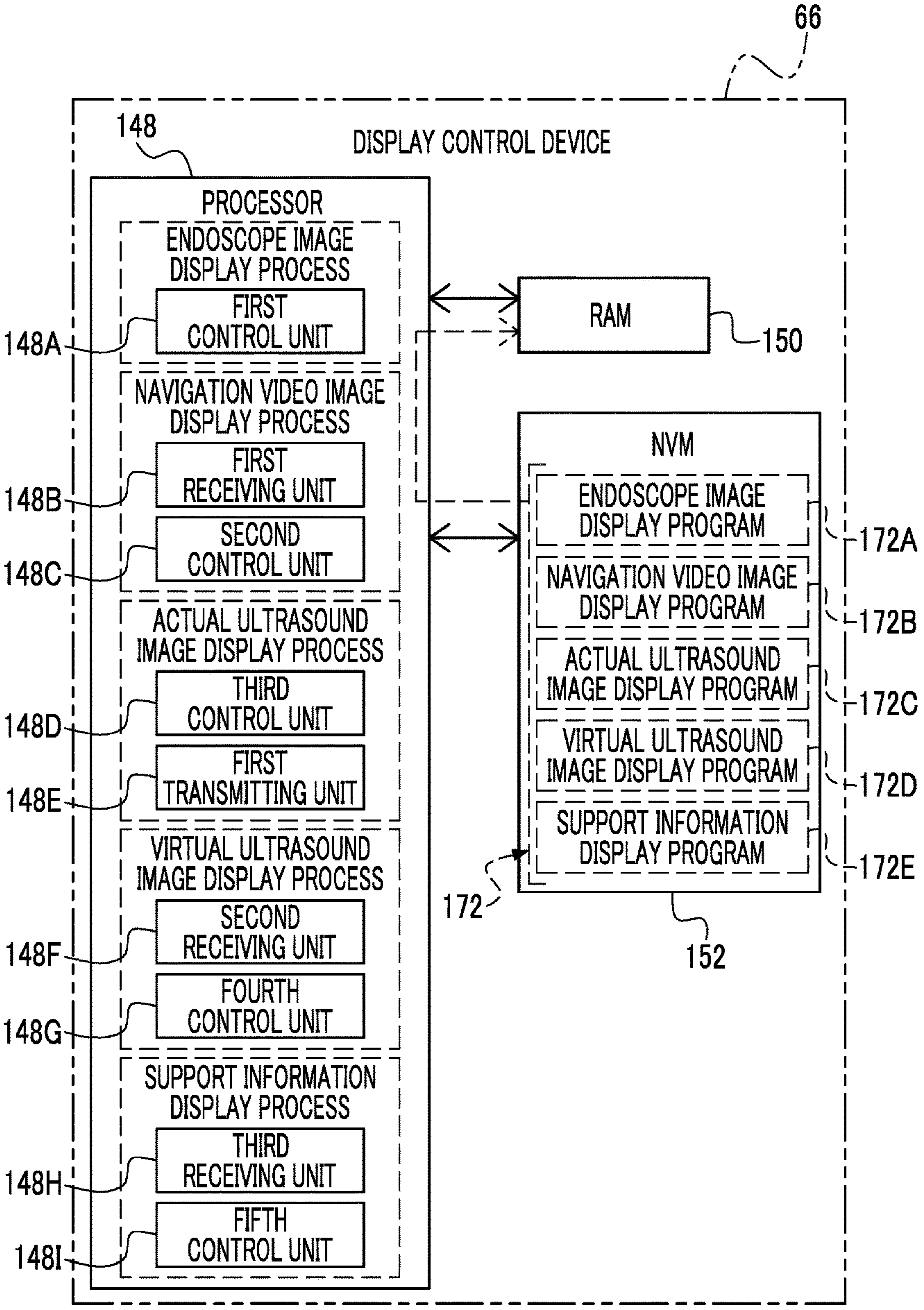
FIG. 8 is a block diagram illustrating an example of functions of main units of a processor of the display control device.

For example, as illustrated in FIG. 8, display-control-device-side programs 172 are stored in the NVM 152. The display-control-device-side programs 172 include an endoscope image display program 172A, a navigation video image display program 172B, an actual ultrasound image display program 172C, a virtual ultrasound image display program 172D, and a support information display program 172E.

The processor 148 reads the display-control-device-side programs 172 from the NVM 152 and executes the read display-control-device-side programs 172 on the RAM 150 to perform the display-control-device-side processes. The processor 148 operates as a first control unit 148A according to the endoscope image display program 172A executed on the RAM 150 to implement the endoscope image display process included in the display-control-device-side processes. The processor 148 operates as a first receiving unit 148B and a second control unit 148C according to the navigation video image display program 172B executed on the RAM 150 to implement the navigation video image display process included in the display-control-device-side processes. The processor 148 operates as a third control unit 148D and a first transmitting unit 148E according to the actual ultrasound image display program 172C executed on the RAM 150 to implement the actual ultrasound image display process included in the display-control-device-side processes. The processor 148 operates as a second receiving unit 148F and a fourth control unit 148G according to the virtual ultrasound image display program 172D executed on the RAM 150 to implement the virtual ultrasound image display process included in the display-control-device-side processes. The processor 148 operates as a third receiving unit 148H and a fifth control unit 148I according to the support information display program 172E executed on the RAM 150 to implement the support information display process included in the display-control-device-side processes.

Figure 9:
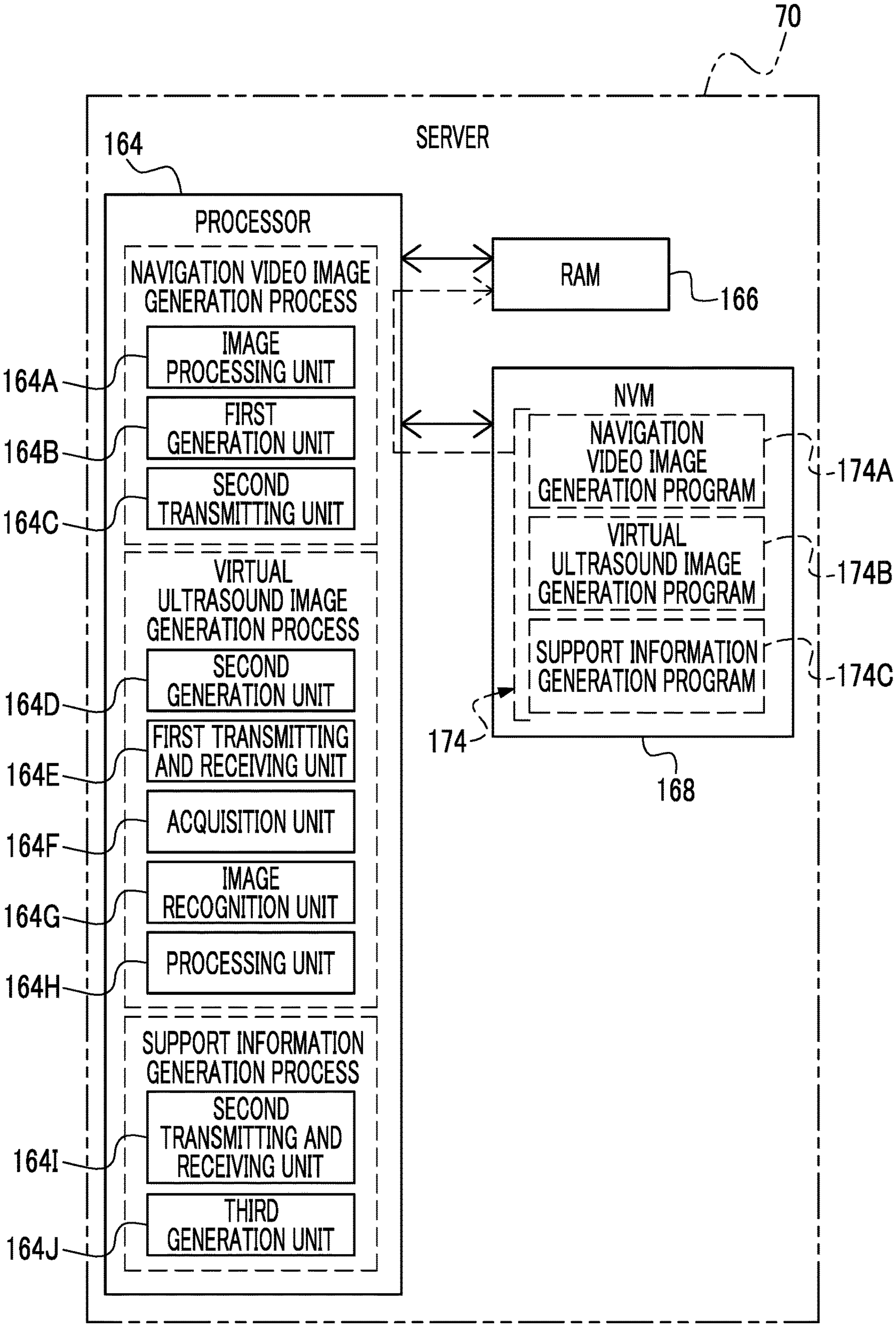
FIG. 9 is a block diagram illustrating an example of functions of main units of a processor of the server.

For example, as illustrated in FIG. 9, server-side programs 174 are stored in the NVM 168. The server-side programs 174 include a navigation video image generation program 174A, a virtual ultrasound image generation program 174B, and a support information generation program 174C.

The processor 164 reads the server-side programs 174 from the NVM 168 and executes the read server-side programs 174 on the RAM 166 to perform the server-side processes. The processor 164 operates as an image processing unit 164A, a first generation unit 164B, and a second transmitting unit 164C according to the navigation video image generation program 174A executed by the RAM 166 to implement the navigation video image generation process included in the server-side processes. The processor 164 operates as a second generation unit 164D, a first transmitting and receiving unit 164E, an acquisition unit 164F, an image recognition unit 164G, and a processing unit 164H according to the virtual ultrasound image generation program 174B executed on the RAM 166 to implement the virtual ultrasound image generation process included in the server-side processes. The processor 164 operates as a second transmitting and receiving unit 164I and a third generation unit 164J according to the support information generation program 174C executed on the RAM 166 to implement the support information generation process included in the server-side processes.

The display-control-device-side programs 172 and the server-side programs 174 are an example of a "program" according to the technology of the present disclosure.

Figure 10:
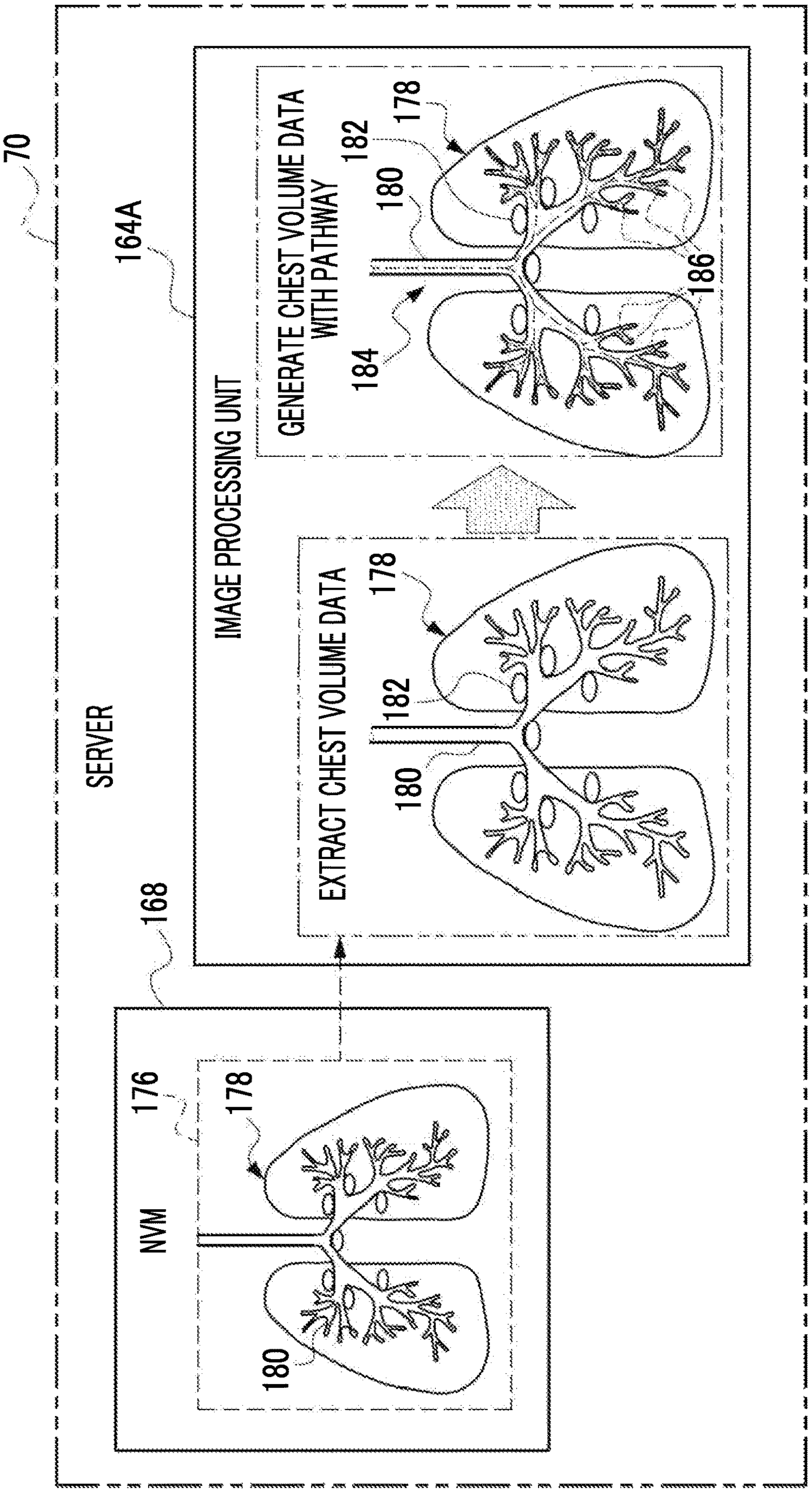
FIG. 10 is a conceptual diagram illustrating an example of content of a first process of an image processing unit of the server.

For example, as illustrated in FIG. 10, in the server 70, volume data 176 is stored in the NVM 168. The volume data 176 is an example of "volume data" according to the technology of the present disclosure. The volume data 176 is a three-dimensional image in which a plurality of two-dimensional slice images obtained by imaging the whole body or a part (for example, a part including a chest) of the body of the subject 20 with a modality are stacked and defined by voxels. The position of each voxel is specified by three-dimensional coordinates. An example of the modality is a CT apparatus. The CT apparatus is only an example, and other examples of the modality are an MRI apparatus and an ultrasound diagnostic apparatus.

The volume data 176 includes chest volume data 178 which is a three-dimensional image including the chest including the observation target region 106. In addition, the chest volume data 178 includes luminal organ volume data 180 which is a three-dimensional image including the luminal organ 84. Further, the chest volume data 178 includes lymph node volume data 182. The lymph node volume data 182 is a three-dimensional image including the lymph node. The chest volume data 178 includes the lymph node volume data 182 for each of a plurality of lymph nodes including the lymph node 104.

The image processing unit 164A extracts the chest volume data 178 from the volume data 176. Then, the image processing unit 164A generates chest volume data 184 with a pathway on the basis of the chest volume data 178. The chest volume data 184 with a pathway is volume data including the chest volume data 178 and a plurality of luminal organ pathways 186.

The plurality of luminal organ pathways 186 are generated by performing a thinning process on the luminal organ volume data 180 included in the chest volume data 178. The luminal organ pathway 186 is a three-dimensional line passing through the center of the luminal organ 84 indicated by the luminal organ volume data 180 in a cross-sectional view. The three-dimensional line passing through the center of the luminal organ 84 indicated by the luminal organ volume data 180 in a cross-sectional view is obtained by thinning the luminal organ volume data 180. The number of luminal organ pathways 186 corresponds to the number of peripheries of the bronchi 96 (see FIG. 3) indicated by the luminal organ volume data 180. In addition, each luminal organ pathway 186 is the shortest pathway to the periphery of the corresponding bronchus 96.

Figure 11:
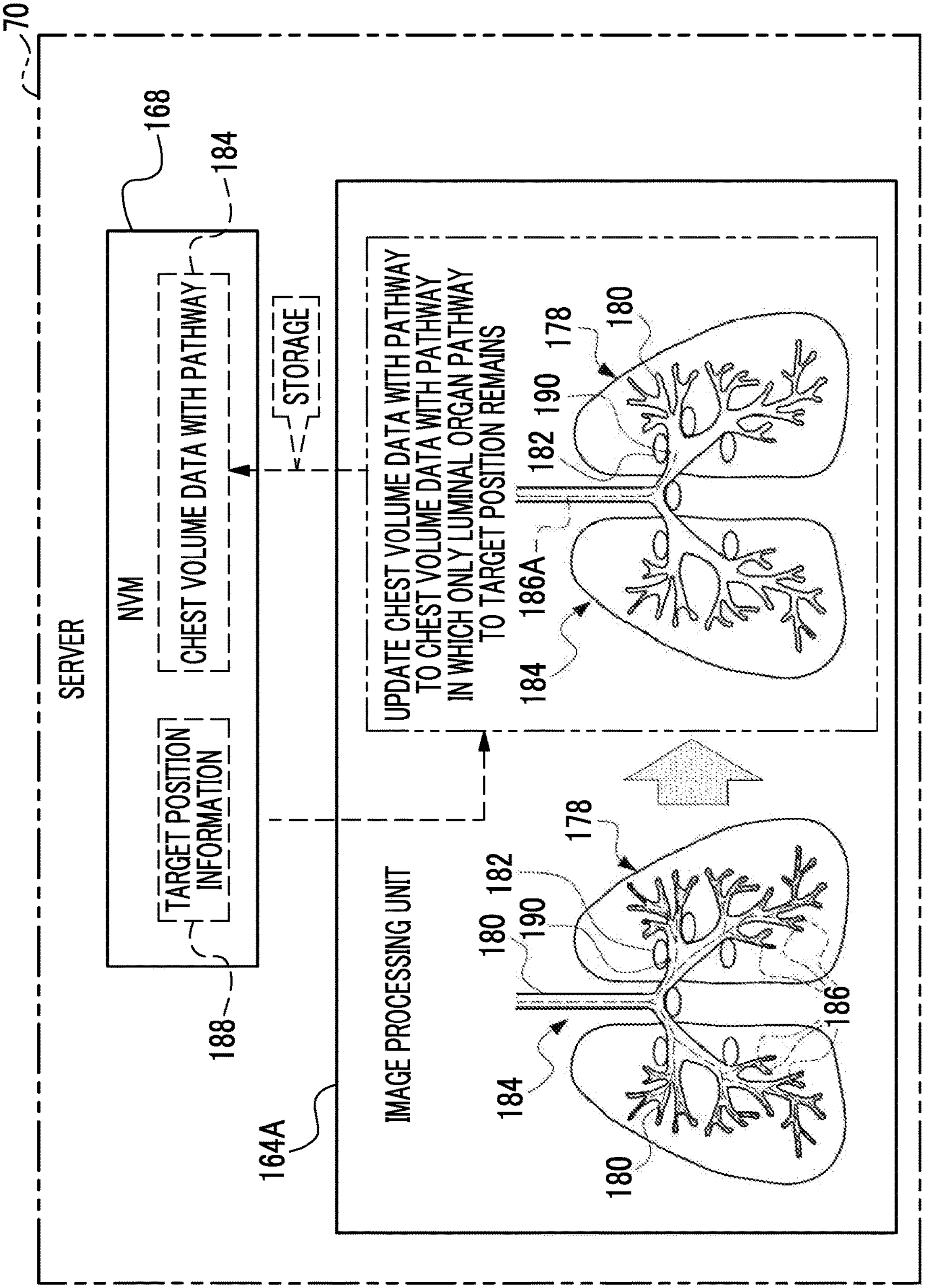
FIG. 11 is a conceptual diagram illustrating an example of content of a second process of the image processing unit of the server.

For example, as illustrated in FIG. 11, target position information 188 is stored in the NVM 168. The target position information 188 is information (for example, three-dimensional coordinates) that can specify a target position 190 in the luminal organ volume data 180. The target position 190 is a position corresponding to the position 100 (see FIG. 3) in the body of the subject 20. The image processing unit 164A updates the chest volume data 184 with a pathway to the chest volume data 184 with a pathway in which only a luminal organ pathway 186A remains, with reference to the target position information 188. The luminal organ pathway 186A is a pathway from a starting point of one luminal organ pathway 186, which passes through the target position 190 among the plurality of luminal organ pathways 186, to a point corresponding to the target position 190. The image processing unit 164A stores the updated chest volume data 184 with a pathway in the NVM 168.

Figure 12:
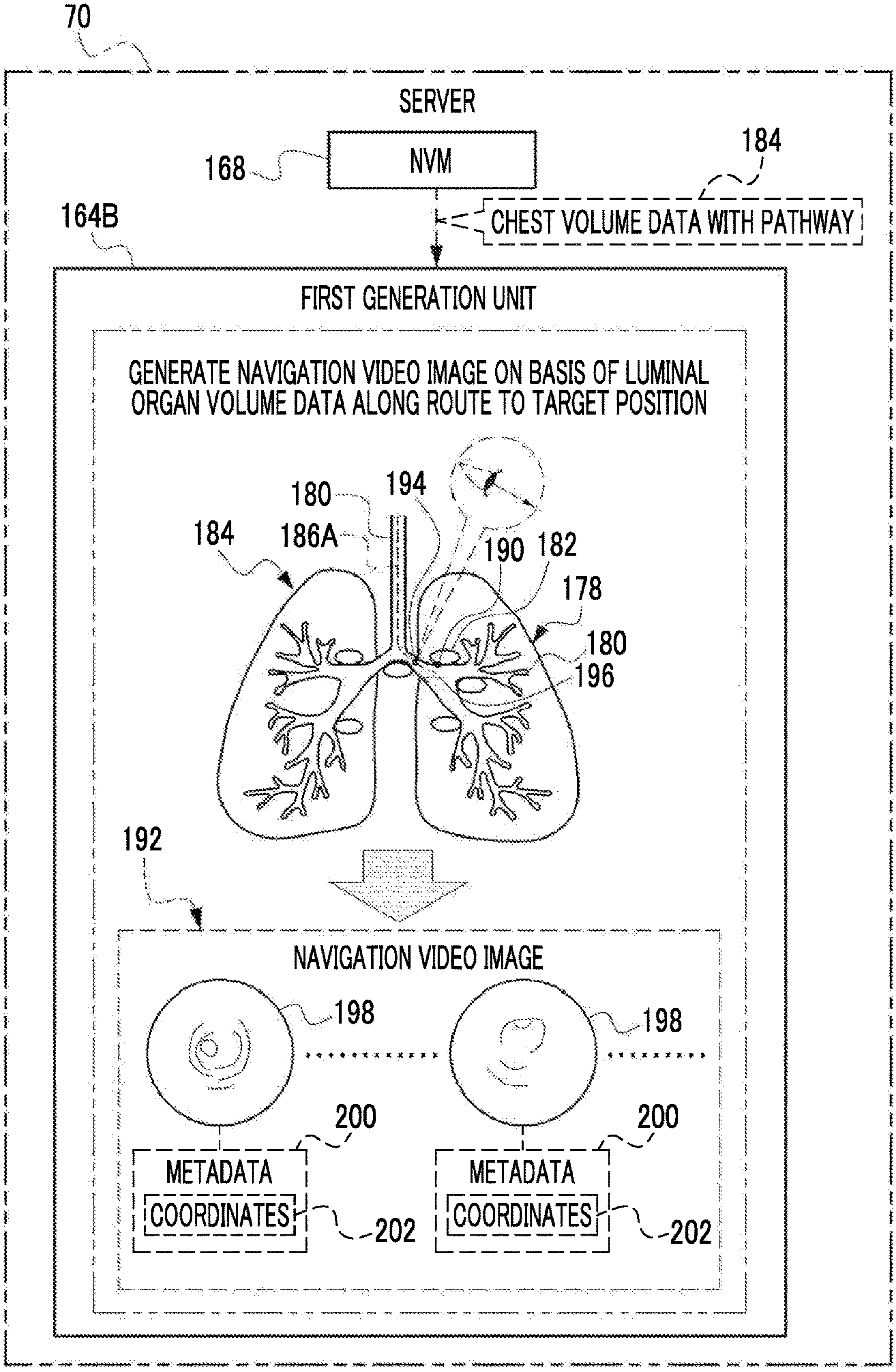
FIG. 12 is a conceptual diagram illustrating an example of content of a process of a first generation unit of the server.

For example, as illustrated in FIG. 12, in the server 70, the first generation unit 164B acquires the chest volume data 184 with a pathway from the NVM 168. The first generation unit 164B extracts the luminal organ volume data 180 along the luminal organ pathway 186A from the chest volume data 184 with a pathway. Then, the first generation unit 164B generates a navigation video image 192 for guiding the movement of the distal end part 38 (see FIGS. 2 and 3) of the bronchoscope 18 on the basis of the luminal organ volume data 180 along the luminal organ pathway 186A. The navigation video image is an example of a "surface image" and a "video image" according to the technology of the present disclosure.

The navigation video image 192 is a video image including the luminal organ inner wall surface 102 illustrated in FIG. 3. A virtual viewpoint 194 is provided in the luminal organ pathway 186A. The viewpoint 194 advances along the luminal organ pathway 186A. In other words, the viewpoint 194 is a virtual endoscope corresponding to the camera 46 in the distal end part 38 of the bronchoscope 18. While the camera 46 is a physical camera, the virtual endoscope is a virtual camera. The navigation video image 192 is a video image showing an aspect in which a luminal organ inner wall surface 196 (that is, the luminal organ inner wall surface 102 illustrated in FIG. 3) indicated by the luminal organ volume data 180 is observed from the viewpoint 194 advancing from the starting point to the end point of the luminal organ pathway 186A.

The navigation video image 192 includes a plurality of frames 198 obtained at a predetermined frame rate from the starting point to the end point of the luminal organ pathway 186A. The frame 198 is a single image. The plurality of frames 198 are arranged in time series along a direction in which the viewpoint 194 advances (that is, a termination direction of the luminal organ pathway 186A). Further, metadata 200 is given to each frame 198. The metadata 200 includes, for example, coordinates 202 (that is, three-dimensional coordinates) capable of specifying which position of the luminal organ pathway 186A each frame 198 corresponds to. In addition, the metadata 200 includes information related to the frame 198 in addition to the coordinates 202. A frame identifier and/or a branch identifier is given as an example of the information included in the metadata 200 other than the coordinates 202. The frame identifier is an identifier that can specify the frame 198. The branch identifier is an identifier that can specify a branch of the bronchus 96 included in the frame 198.

Figure 13:
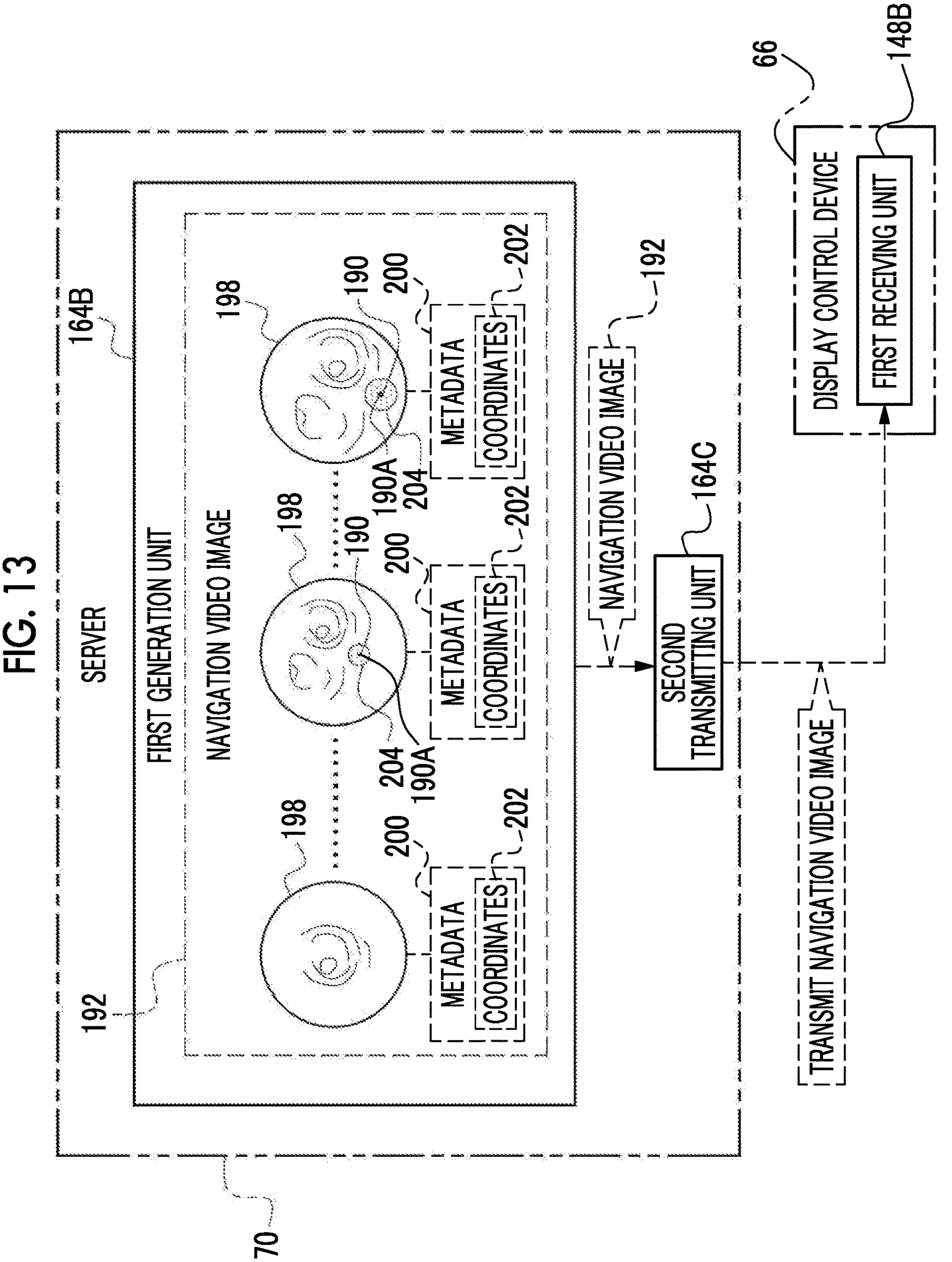
FIG. 13 is a conceptual diagram illustrating an example of content of processes of the first generation unit and a second transmitting unit of the server.

For example, as illustrated in FIG. 13, the first generation unit 164B superimposes an aiming mark 204, which is a mark capable of specifying a recommended region irradiated with the ultrasonic waves by the ultrasound probe 48, on a plurality of corresponding frames 198 included in the navigation video image 192. The plurality of corresponding frames 198 mean a plurality of frames 198 including the target position 190. The aiming mark 204 is a circular mark having the target position 190 as its center and is colored. The position to which the aiming mark 204 is given in the frame 198 is a position which corresponds to the position where the ultrasonic waves are emitted from the ultrasound probe 48 in a real space in the frame 198.

An example of the color given to the aiming mark 204 is a translucent chromatic color (for example, yellow). The color intensity and/or brightness of the aiming mark 204 may be changed depending on the distance between the viewpoint 194 (see FIG. 12) and the target position 190. For example, the closer the viewpoint 194 is to the target position 190, the higher the color intensity or the brightness is. The distance between the viewpoint 194 and the target position 190 is calculated on the basis of, for example, the coordinates included in the metadata 200. The size (that is, the diameter) of the aiming mark 204 corresponds to the size of the lymph node 104 and is calculated by the first generation unit 164B on the basis of the lymph node volume data 182. In addition, a mark 190A that can specify the target position 190 is given to the center of the aiming mark 204. Here, the aspect in which the mark 190A is given to the aiming mark 204 has been described. However, this is only an example, and the technology of the present disclosure is established even in a case in which the mark 190A is not given to the aiming mark 204. Further, the aiming mark 204 does not need to be a circular mark and may be a mark having another shape. Furthermore, the color of the aiming mark 204 does not need to be a translucent chromatic color and may be another color. The aiming mark 204 may be any mark as long as it can specify the position where the lymph node 104 is present.

In the server 70, the second transmitting unit 164C transmits the navigation video image 192 generated by the first generation unit 164B to the display control device 66. In the display control device 66, the first receiving unit 148B receives the navigation video image 192 transmitted from the second transmitting unit 164C.

Figure 14:
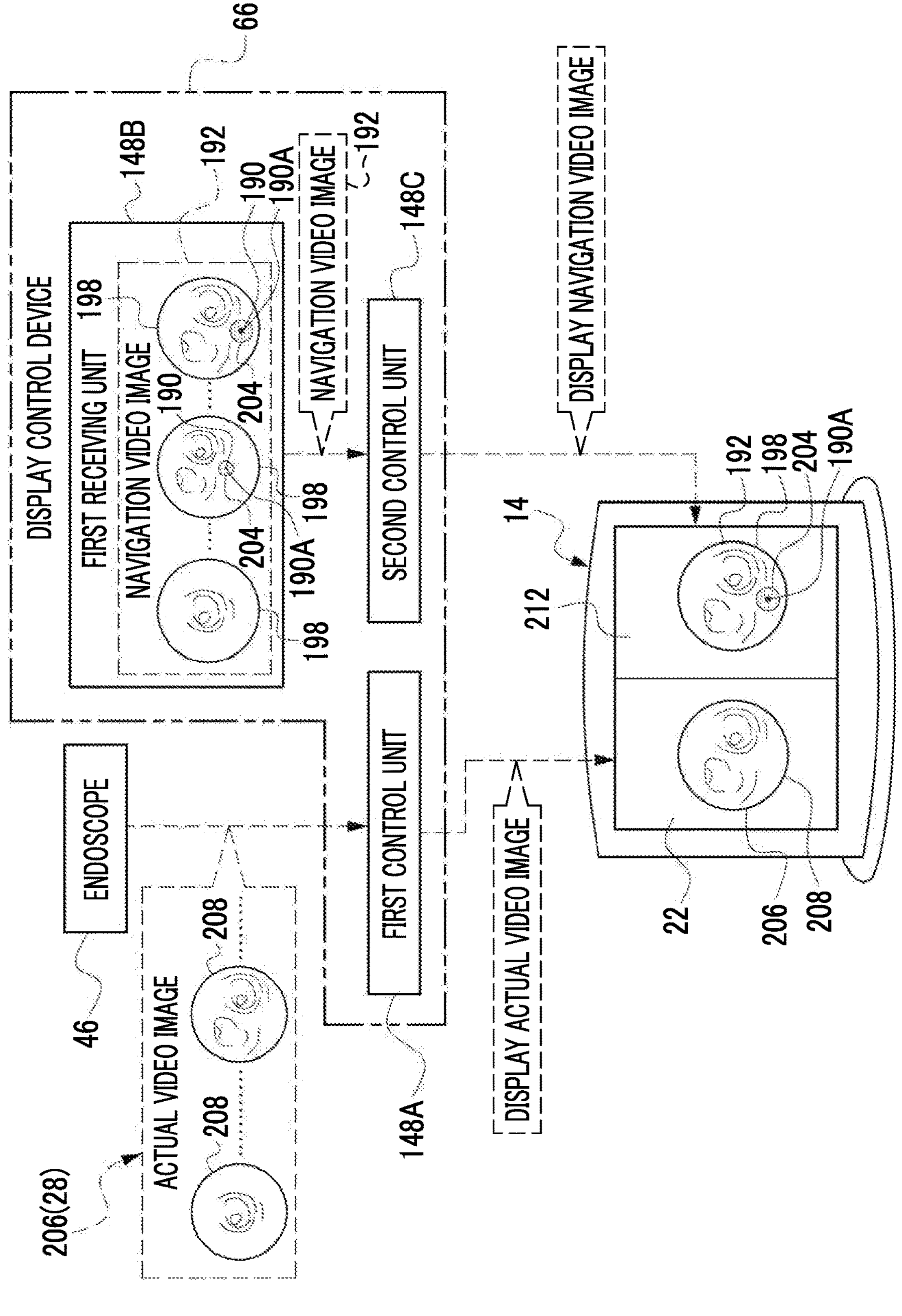
FIG. 14 is a conceptual diagram illustrating an example of content of processes of a first control unit and a second control unit of the display control device.

For example, as illustrated in FIG. 14, in the display control device 66, the first control unit 148A acquires an actual video image 206, which is an image of the inside of the body actually observed, from the camera 46. The actual video image 206 is an example of the endoscope image 28 illustrated in FIG. 1. The actual video image 206 is a video image (here, for example, a live view image) obtained by imaging the inside of the luminal organ 84 (see FIG. 3) along the route 98 (see FIG. 3) with the camera 46. The actual video image 206 includes a plurality of frames 208 obtained by performing imaging according to a predetermined frame rate from a starting point to an end point of the route 98. The frame 208 is a single image. The first control unit 148A generates the screen 22 and outputs the screen 22 to the display device 14 such that the screen 22 is displayed on the display device 14. The plurality of frames 208 are sequentially displayed on the screen 22 in time series according to a predetermined frame rate under the control of the first control unit 148A. Therefore, the actual video image 206 is displayed on the screen 22.

The second control unit 148C generates a screen 212 and outputs the screen 212 to the display device 14 such that the screen 212 is displayed on the display device 14. A plurality of frames 198 are displayed on the screen 212 under the control of the second control unit 148C. Therefore, the navigation video image 192 is displayed on the screen 212. Further, in the example illustrated in FIG. 14, the frame 198 on which the aiming mark 204 has been superimposed is displayed on the screen 212.

Furthermore, in the example illustrated in FIG. 14, the screen of the display device 14 is divided into two screens of the screen 22 and the screen 212. However, this is only an example, and the screens 22 and 212 may be selectively displayed according to conditions given to the display control device 66 (for example, the instruction received by the receiving device 68). In addition, the actual video image 206 and the navigation video image 192 may be selectively displayed on the full screen according to the conditions given to the display control device 66.

Further, the speed at which the display of the navigation video image 192 is advanced is generally constant unless an instruction from the user (for example, a voice instruction by the doctor 16) is received by the receiving device 68. An example of the constant speed is a speed that is calculated from the distance from the starting point to the end point of the luminal organ pathway 186A and from a default time required for the viewpoint 194 to move from the starting point to the end point of the luminal organ pathway 186A.

In addition, the display aspect including the speed at which the display of the navigation video image 192 is advanced is changed on condition that the instruction from the user (for example, the voice instruction by the doctor 16) is received by the receiving device 68. For example, the speed at which the display of the navigation video image 192 is advanced is changed according to the instruction received by the receiving device 68. The change in the speed at which the display of the navigation video image 192 is advanced is implemented by, for example, so-called fast forward, frame-by-frame playback, and slow playback.

Figure 15:
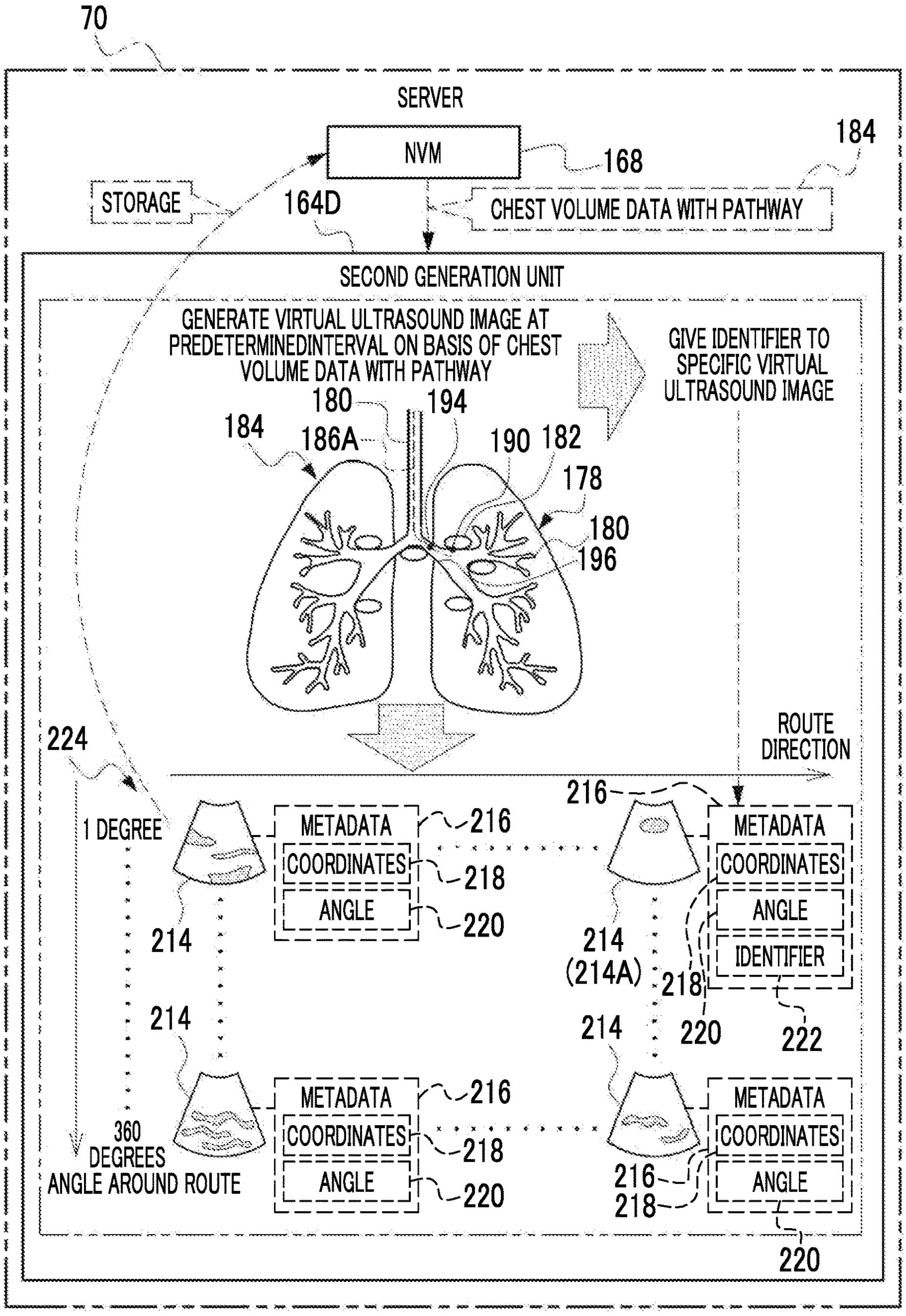
FIG. 15 is a conceptual diagram illustrating an example of content of a process of a second generation unit of the server.

For example, as illustrated in FIG. 15, the second generation unit 164D acquires the chest volume data 184 with a pathway from the NVM 168. The second generation unit 164D generates a virtual ultrasound image 214 at a predetermined interval (for example, in units of one to several voxels) along the luminal organ pathway 186A on the basis of the chest volume data 184 with a pathway. The virtual ultrasound image 214 is a virtual ultrasound image showing the aspect of the observation target region 106. The virtual ultrasound image means a virtual image obtained as an image that imitates the actual ultrasound image 30 by processing the chest volume data 178 included in the chest volume data 184 with a pathway. The image that imitates the actual ultrasound image 30 means an image that imitates the actual ultrasound image 30 generated in the B-mode.

The second generation unit 164D generates the virtual ultrasound image 214 at a predetermined interval along the luminal organ pathway 186A and at a predetermined angle (for example, 1 degree) around the luminal organ pathway 186A. The term "predetermined interval" and/or "predetermined angle" may be a default value or may be determined according to the instruction and/or various conditions (for example, the type of the bronchoscope 18) received by the receiving device 68 or 76.

Metadata 216 is given to each virtual ultrasound image 214. The metadata 216 includes coordinates 218 (that is, three-dimensional coordinates) that can specify the position of the luminal organ pathway 186A at a predetermined interval and an angle 220 around the luminal organ pathway 186A.

In addition, the plurality of virtual ultrasound images 214 include a specific virtual ultrasound image 214A which is a virtual ultrasound image 214 corresponding to the target position 190. The virtual ultrasound image 214 corresponding to the target position 190 means a virtual ultrasound image 214 which corresponds to the actual ultrasound image 30 obtained in a case in which the position 108 and the position 100 illustrated in FIG. 3 are matched with each other, among the plurality of virtual ultrasound images 214. An example of the actual ultrasound image 30 obtained in a case in which the position 108 and the position 100 illustrated in FIG. 3 are matched with each other is the actual ultrasound image 30 obtained in a case in which the distal end part 38 is located at the position 108 where the central portion 104A of the lymph node 104 is punctured by the puncture needle 52B.

The second generation unit 164D includes an identifier 222 which can identify the specific virtual ultrasound image 214A in the metadata 216 of the specific virtual ultrasound image 214A, and gives the identifier 222 to the specific virtual ultrasound image 214A.

The second generation unit 164D stores a virtual ultrasound image group 224 in the NVM 168. The virtual ultrasound image group 224 includes a plurality of virtual ultrasound images 214 which have been generated at a predetermined interval along the luminal organ pathway 186A and at a predetermined angular interval around the luminal organ pathway 186A and which each have been given the metadata 216.

Figure 16:
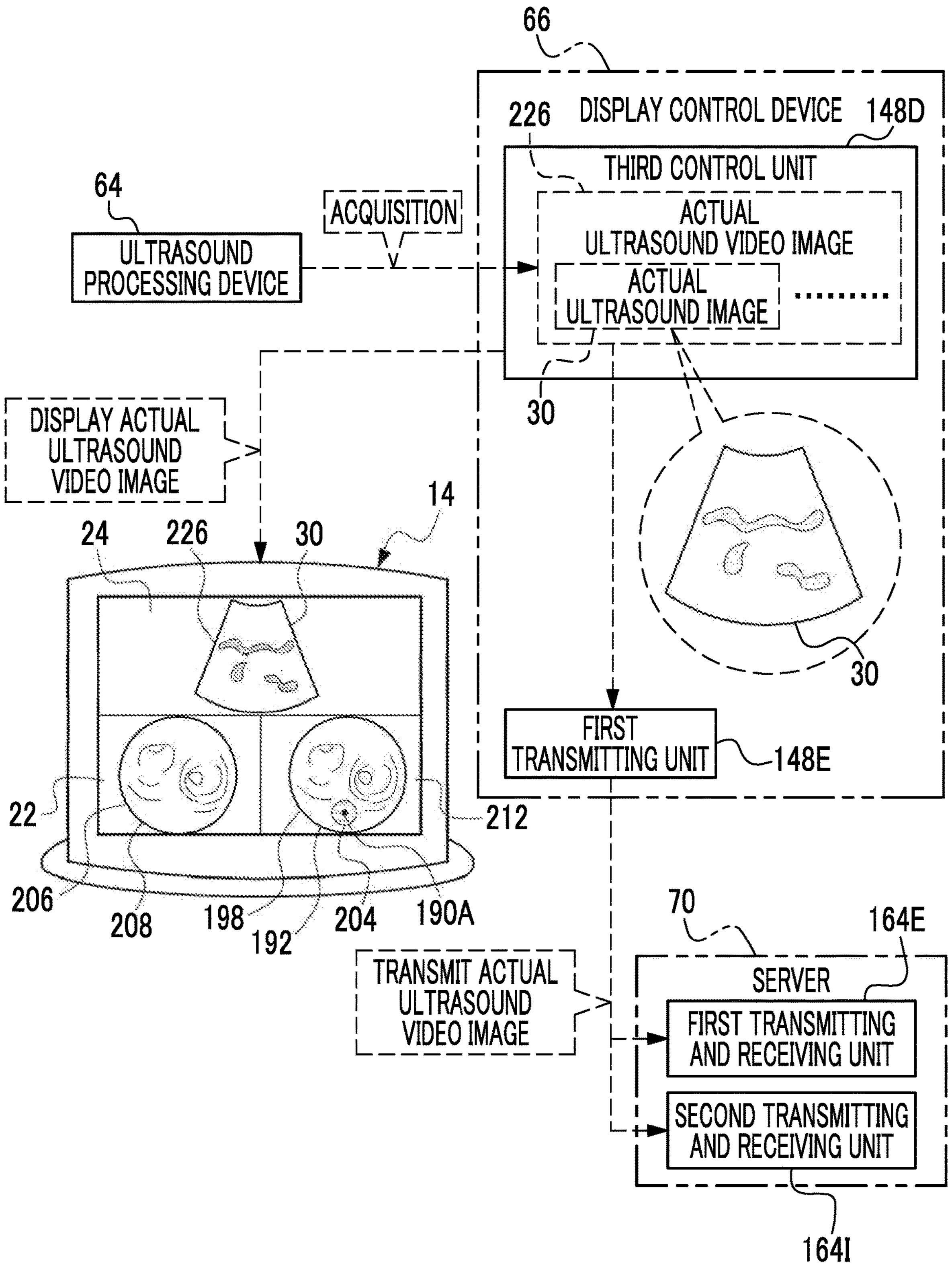
FIG. 16 is a conceptual diagram illustrating an example of content of processes of a third control unit and a first transmitting unit of the display control device and an example of content of processes of a first transmitting and receiving unit and a second transmitting and receiving unit of the server.

For example, as illustrated in FIG. 16, the third control unit 148D acquires an actual ultrasound video image 226 from the ultrasound processing device 64. The actual ultrasound video image 226 is a plurality of actual ultrasound images 30 arranged in time series (that is, a plurality of actual ultrasound images 30 sequentially generated at a predetermined frame rate by the ultrasound processing device 64). The third control unit 148D generates the screen 24 and outputs the screen 24 to the display device 14 such that the screen 24 is displayed on the display device 14. The plurality of actual ultrasound images 30 are sequentially displayed on the screen 24 in time series at a predetermined frame rate under the control of the third control unit 148D. Therefore, the actual ultrasound video image 226 is displayed on the screen 24. In addition, the screen 24 is displayed side by side with the screens 22 and 212. That is, the actual ultrasound video image 226, the actual video image 206, and the navigation video image 192 are displayed on the display device 14 in a state in which they can be compared.

In the example illustrated in FIG. 16, the screen of the display device 14 is divided into three screens 22, 212, and 24. However, this is only an example, and the screens 22, 212, and 24 may be selectively displayed according to the conditions given to the display control device 66 (for example, the instruction received by the receiving device 68). In addition, the actual ultrasound video image 226, the actual video image 206, and the navigation video image 192 may be selectively displayed on the full screen according to the conditions given to the display control device 66. Further, at least one of the screen 22, the screen 212, or the screen 24 may be displayed on at least one display device other than the display device 14.

The first transmitting unit 148E transmits the actual ultrasound video image 226 acquired from the ultrasound processing device 64 by the third control unit 148D to the server 70. In the server 70, the first transmitting and receiving unit 164E and the second transmitting and receiving unit 164I receive the actual ultrasound video image 226 transmitted from the first transmitting unit 148E.

Figure 17:
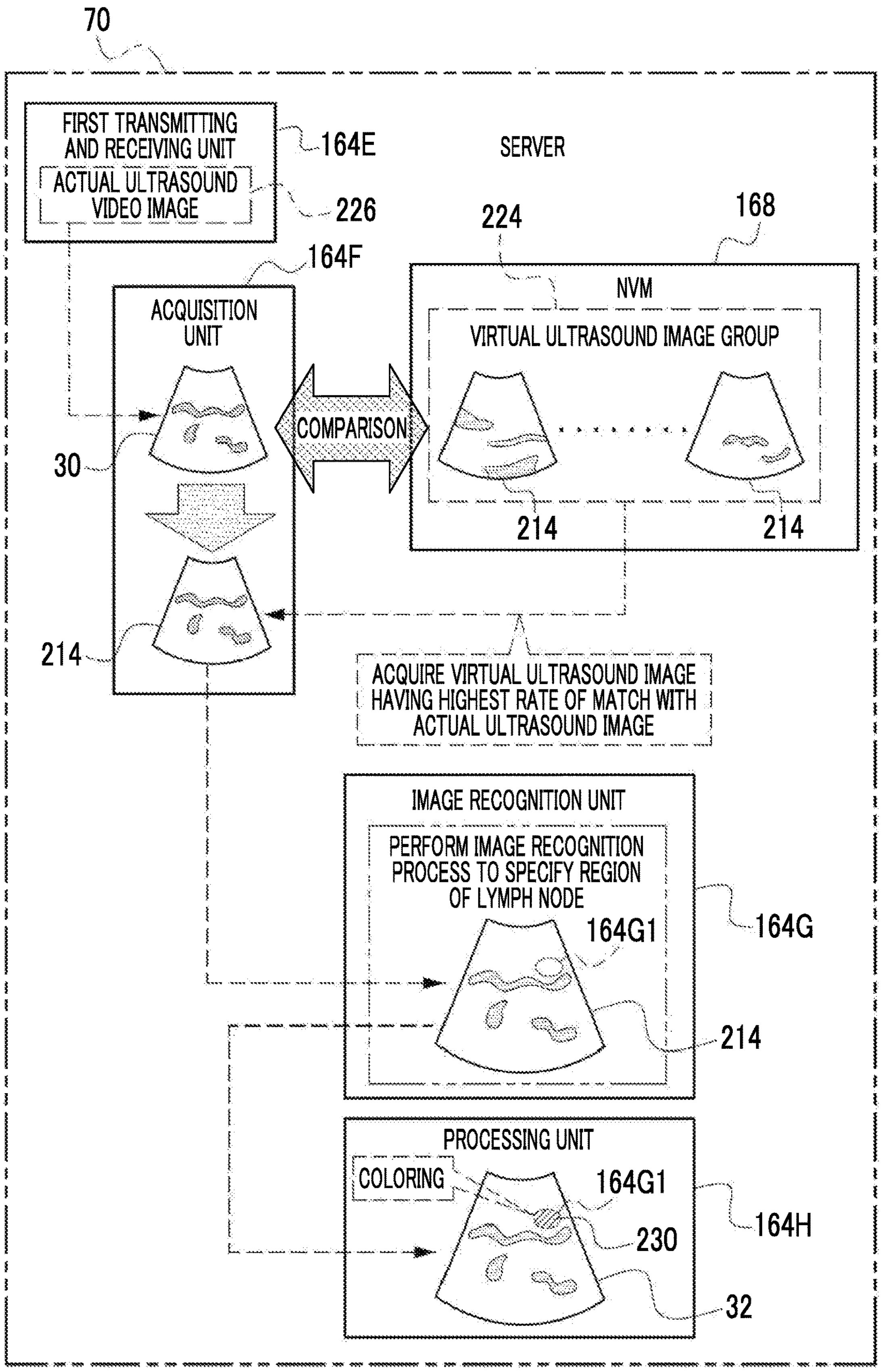
FIG. 17 is a conceptual diagram illustrating an example of content of processes of the first transmitting and receiving unit, an acquisition unit, an image recognition unit, and a processing unit of the server.

For example, as illustrated in FIG. 17, in the server 70, the acquisition unit 164F acquires the actual ultrasound image 30 frame by frame in time series from the actual ultrasound video image 226 received by the first transmitting and receiving unit 164E. The acquisition unit 164F compares the actual ultrasound image 30 acquired from the actual ultrasound video image 226 with the virtual ultrasound image group 224 stored in the NVM 168 and selects and acquires the virtual ultrasound image 214 having the highest rate of match with the actual ultrasound image 30 from the virtual ultrasound image group 224. In this embodiment, the comparison between the actual ultrasound image 30 and the virtual ultrasound image group 224 means, for example, pattern matching. In addition, the aspect in which the virtual ultrasound image 214 having the highest rate of match with the actual ultrasound image 30 is selected from the virtual ultrasound image group 224 has been described here. However, the technology of the present disclosure is not limited to this aspect. For example, the virtual ultrasound image 214 whose rate of match with the actual ultrasound image 30 is equal to or greater than a predetermined value (for example, in a case in which the rate of match with the actual ultrasound image 30 is equal to or greater than 99%, the virtual ultrasound image 214 having the second highest rate of match with the actual ultrasound image 30) may be selected.

The image recognition unit 164G performs an AI-type image recognition process on the virtual ultrasound image 214 acquired by the acquisition unit 164F to specify a region 164G1 in which the lymph node included in the virtual ultrasound image 214 is present. The region 164G1 is represented by two-dimensional coordinates that can specify a position in the virtual ultrasound image 214. In addition, the AI-type image recognition process is applied here. However, this is only an example, and a template-matching-type image recognition process may be applied.

The processing unit 164H superimposes an image recognition result mark 230 on the virtual ultrasound image 214 to generate the virtual ultrasound image 32. The image recognition result mark 230 is a mark obtained by coloring the region 164G1 in the virtual ultrasound image 214. An example of the color given to the region 164G1 is a translucent chromatic color (for example, blue). The color given to the region 164G1 may be any color as long as it distinctively expresses the difference from other regions in the virtual ultrasound image 214. In addition, the color and/or the brightness of the contour of the region 164G1 may be adjusted to distinctively express the difference between the region 164G1 and other regions in the virtual ultrasound image 214.

Figure 18:
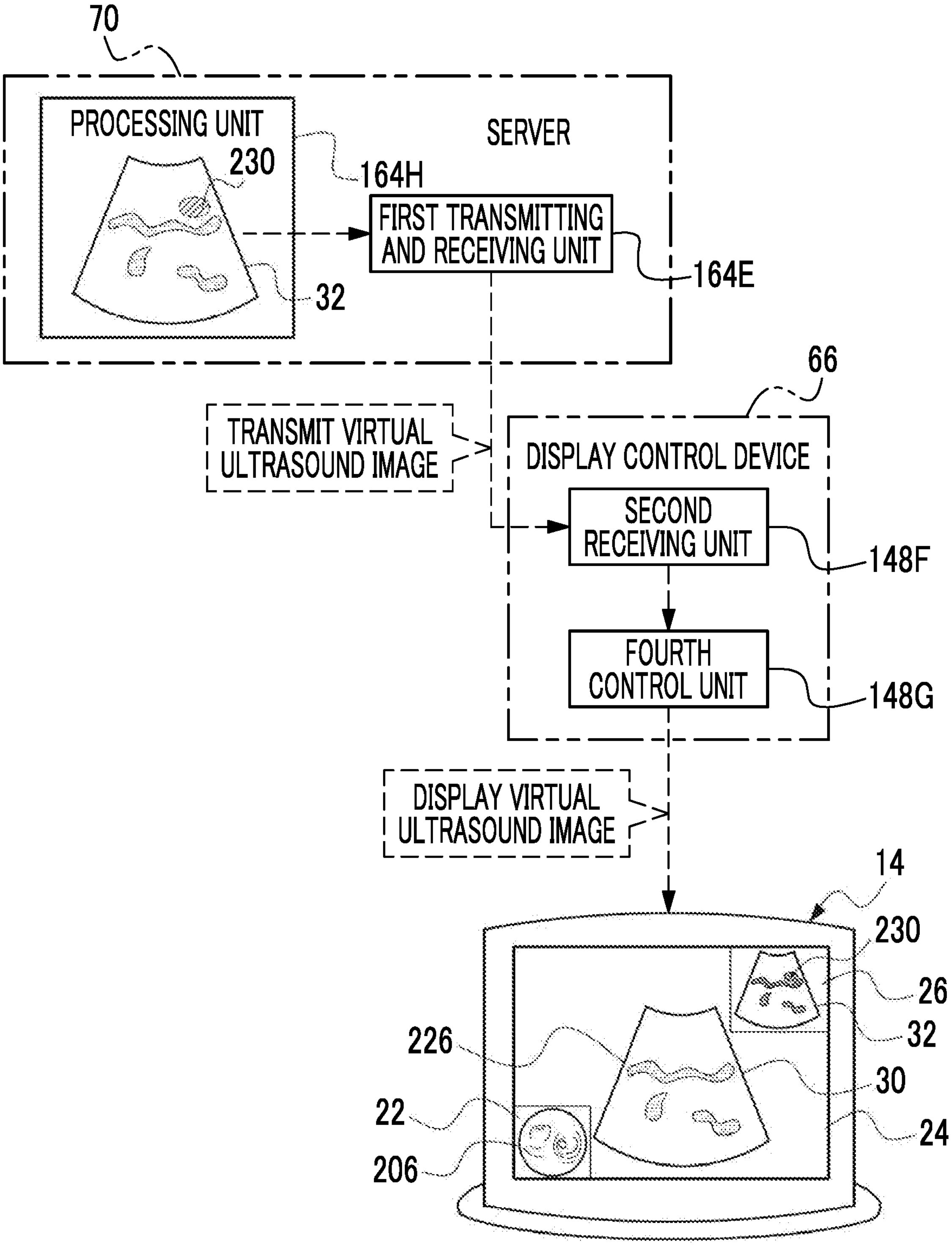
FIG. 18 is a conceptual diagram illustrating an example of content of processes of the processing unit and the first transmitting and receiving unit of the server and an example of content of processes of a second receiving unit and a fourth control unit of the display control device.

For example, as illustrated in FIG. 18, in the server 70, the first transmitting and receiving unit 164E transmits the virtual ultrasound image 32 generated by the processing unit 164H to the display control device 66. In the display control device 66, the second receiving unit 148F receives the virtual ultrasound image 32 transmitted from the first transmitting and receiving unit 164E. The fourth control unit 148G generates the screen 26 and outputs the screen 26 to the display device 14 such that the screen 26 is displayed on the display device 14. The virtual ultrasound image 32 is displayed on the screen 26 under the control of the fourth control unit 148G. Therefore, the image recognition result mark 230 is also displayed. This means that the result of the AI-type image recognition process by the image recognition unit 164G is displayed as the image recognition result mark 230.

In addition, the screen 26 is displayed side by side with the screens 22 and 24. That is, the virtual ultrasound image 32, the actual video image 206, and the actual ultrasound video image 226 are displayed on the display device 14 in a state in which they can be compared.

In the example illustrated in FIG. 18, the screen of the display device 14 is divided into three screens 22, 24, and 26. However, this is only an example, and the screens 22, 24, and 26 may be selectively displayed according to the conditions given to the display control device 66 (for example, the instruction received by the receiving device 68). In addition, the virtual ultrasound image 32, the actual video image 206, and the actual ultrasound video image 226 may be selectively displayed on the full screen according to the conditions given to the display control device 66. In addition, at least one of the screen 22, the screen 24, or the screen 26 may be displayed on at least one display device other than the display device 14.

Further, in the example illustrated in FIG. 18, the screen 212 is not displayed on the display device 14. However, the screen 212 may also be displayed side by side with the screens 22, 24, and 26. In this case, the display of the screens 22, 24, and 26 and the screen 212 may be selectively switched according to the conditions given to the display control device 66.

In addition, in some cases, the frame 198 on which the aiming mark 204 has been superimposed is displayed on the screen 212 (see FIG. 14). In this case, the actual ultrasound image 30 is obtained by emitting the ultrasonic waves to the position specified from the aiming mark 204 (see FIG. 16). Then, the virtual ultrasound image 32 is generated on the basis of the obtained actual ultrasound image 30, and the generated virtual ultrasound image 32 is displayed on the screen 26 (see FIGS. 17 and 18). That is, this means that the virtual ultrasound image showing the aspect of the observation target region 106 with respect to the position specified from the aiming mark 204 is displayed as the virtual ultrasound image 32 on the screen 26.

Figure 19:
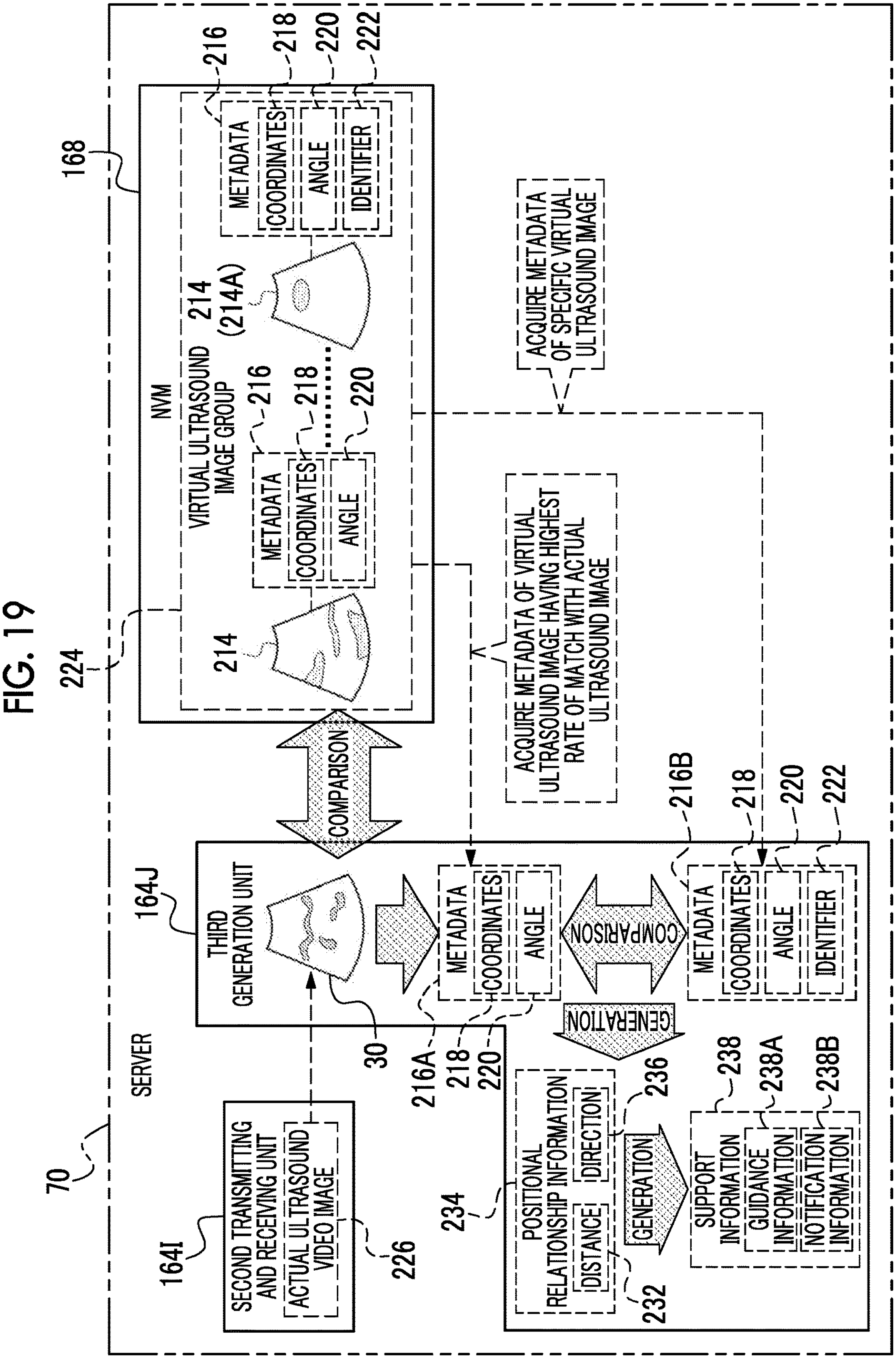
FIG. 19 is a conceptual diagram illustrating an example of content of processes of the second transmitting and receiving unit and a third generation unit of the server.

For example, as illustrated in FIG. 19, in the server 70, the third generation unit 164J acquires the actual ultrasound image 30 frame by frame in time series from the actual ultrasound video image 226 received by the second transmitting and receiving unit 164I. The third generation unit 164J specifies the positional relationship between the position 100 (see FIG. 3) and the position 108 (see FIG. 3) on the basis of the actual ultrasound image 30 acquired from the actual ultrasound video image 226 and the specific virtual ultrasound image 214A. The positional relationship between the position 100 and the position 108 is defined on the basis of the amount of deviation between the position 100 and the position 108.

The third generation unit 164J compares the actual ultrasound image 30 with the specific virtual ultrasound image 214A to calculate the amount of deviation between the position 100 and the position 108. The amount of deviation between the position 100 and the position 108 is an example of an "amount of deviation" according to the technology of the present disclosure. In the example illustrated in FIG. 19, a distance 232 is given as an example of the amount of deviation.

The third generation unit 164J compares the actual ultrasound image 30 with the specific virtual ultrasound image 214A using metadata 216A, which is the metadata 216 of the virtual ultrasound image 214 corresponding to the actual ultrasound image 30, and metadata 216B, which is the metadata 216 of the specific virtual ultrasound image 214A. That is, the comparison between the actual ultrasound image 30 and the specific virtual ultrasound image 214A is implemented by the comparison between the metadata 216A and the metadata 216B. The metadata 216A and the metadata 216B are acquired by the third generation unit 164J. Specifically, the third generation unit 164J compares the actual ultrasound image 30 acquired from the actual ultrasound video image 226 with the virtual ultrasound image group 224 stored in the NVM 168 to acquire the metadata 216A from the virtual ultrasound image group 224. The metadata 216A is the metadata 216 given to the virtual ultrasound image 214 having the highest rate of match with the actual ultrasound image 30. In addition, the third generation unit 164J acquires the metadata 216B from the virtual ultrasound image group 224. The metadata 216B is the metadata 216 including the identifier 222, that is, the metadata 216 given to the specific virtual ultrasound image 214A.

The third generation unit 164J compares the metadata 216A with the metadata 216B to generate positional relationship information 234. The positional relationship information 234 is information for specifying the positional relationship between the position 100 and the position 108 and is defined on the basis of the distance 232 and a direction 236. In the example illustrated in FIG. 19, the positional relationship information 234 includes the distance 232 and the direction 236. The distance 232 is a distance between the coordinates 218 included in the metadata 216A and the coordinates 218 included in the metadata 216B. The direction 236 is a direction in which the position 108 is moved to be matched with the position 100. The direction 236 is defined by, for example, a vector that can specify the direction along the route 98 and the angle around the route 98. The vector that can specify the direction along the route 98 is calculated, for example, on the basis of the coordinates 218 included in the metadata 216A and the coordinates 218 included in the metadata 216B. The angle around the route 98 is calculated, for example, on the basis of the difference between the angle 220 included in the metadata 216A and the angle 220 included in the metadata 216B.

In addition, here, the aspect in which the positional relationship between the position 100 and the position 108 is specified on the basis of the result of the comparison between the metadata 216A and the metadata 216B has been described. However, the technology of the present disclosure is not limited to this aspect. For example, the third generation unit 164J may perform direct comparison (for example, pattern matching) between the actual ultrasound image 30 and the specific virtual ultrasound image 214A to calculate the amount of deviation between the position 100 and the position 108 and specify the positional relationship between the position 100 and the position 108 on the basis of the calculated amount of deviation. In this case, the positional relationship between the position 100 and the position 108 may be defined on the basis of the amount of deviation (for example, the distance) between the position 100 and the position 108.

The third generation unit 164J generates support information 238 on the basis of the positional relationship information 234. The support information 238 is information for supporting the operation of the bronchoscope 18. Examples of the support information 238 include a text message, a voice message, a mark, a numerical value, and/or a symbol for supporting the operation of the bronchoscope 18 (for example, an operation for matching the position 108 with the position 100). The support information 238 selectively includes guidance information 238A and notification information 238B. For example, the support information 238 includes the guidance information 238A in a case in which the position 108 and the position 100 are not matched with each other (for example, in a case in which the distance 232 is not "0"). In addition, the support information 238 includes the notification information 238B in a case in which the position 108 and the position 100 are matched with each other (for example, in a case in which the distance 232 is "0"). The guidance information 238A is information for guiding the position 108 to the position 100. The notification information 238B is information for notifying that the position 108 and the position 100 are matched with each other.

Figure 20:
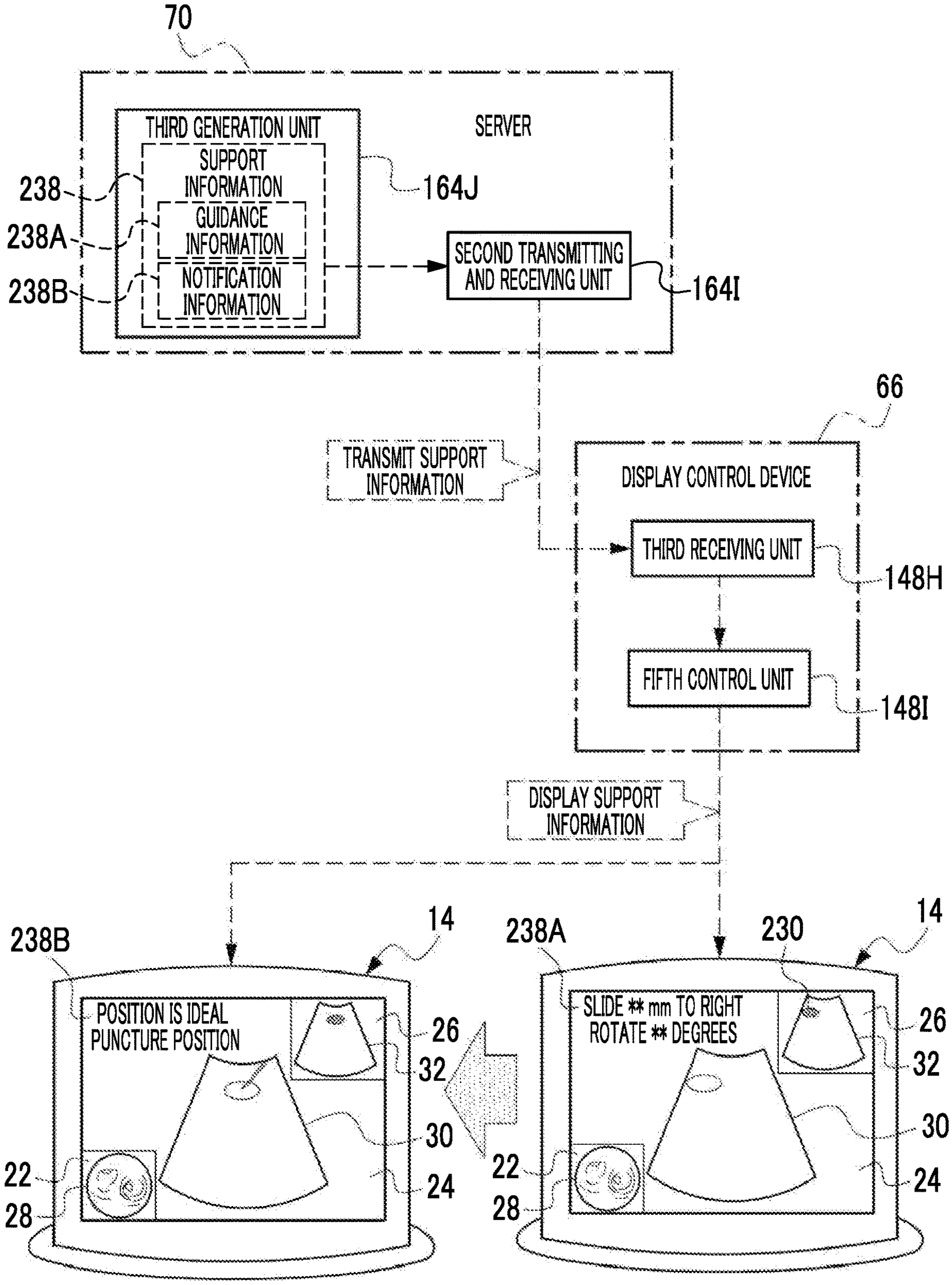
FIG. 20 is a conceptual diagram illustrating an example of the content of the processes of the third generation unit and the second transmitting and receiving unit of the server and an example of content of processes of a third receiving unit and a fifth control unit of the display control device.

For example, as illustrated in FIG. 20, in the server 70, the second transmitting and receiving unit 164I transmits the support information 238 generated by the third generation unit 164J to the display control device 66. In the display control device 66, the third receiving unit 148H receives the support information 238 transmitted from the second transmitting and receiving unit 164I. The fifth control unit 148I performs a first presentation process and a notification process on the basis of the support information 238. The first presentation process is a process of presenting the guidance information 238A. The first presentation process is implemented by displaying the guidance information 238A on the display device 14. The notification process is a process of notifying that the position 108 and the position 100 are matched with each other in a case in which the position 108 and the position 100 are matched with each other. The notification process is implemented by displaying the notification information 238B on the display device 14.

The first presentation process performed by the fifth control unit 148I is an example of a "first presentation process" according to the technology of the present disclosure, and the notification process performed by the fifth control unit 148I is an example of a "notification process" according to the technology of the present disclosure.

In the example illustrated in FIG. 20, in a case in which the position 108 and the position 100 are not matched with each other, the direction in which the position 108 is moved ("to the right" in the example illustrated in FIG. 20), the distance from the position 108 to the position 100 (" mm" in the example illustrated in FIG. 20), the angle between the position 108 and the position 100 (" degrees" in the example illustrated in FIG. 20), and the movement of the distal end part 38 of the bronchoscope 18 ("slide" and "rotation" in the example illustrated in FIG. 20) are displayed as the guidance information 238A on the screen 24 in a message format. In addition, the direction in which the position 108 is moved and/or the angle between the position 108 and the position 100 may be represented by, for example, an arrow, a symbol similar to the arrow, or an image. For example, the direction in which the position 108 is moved may be represented by a straight arrow, and the angle between the position 108 and the position 100 may be represented by an arc arrow.

In the example illustrated in FIG. 20, in a case in which the position 108 and the position 100 are matched with each other, information which notifies that the position 108 is an ideal position (for example, a position where the central portion 104A of the lymph node 104 can be punctured) as the position punctured by the puncture needle 52B ("The position is an ideal puncture position" in the example illustrated in FIG. 20) is displayed as the notification information 238B on the screen 24 in a message format.

Next, the operation of the endoscope system 10 will be described with reference to FIGS. 21 to 28.

First, an example of a flow of the endoscope image display process performed by the processor 148 of the display control device 66 in a case in which the camera 46 is inserted into the luminal organ 84 of the subject 20 will be described with reference to FIG. 21. In addition, here, the description will be made on the premise that the camera 46 performs imaging at a predetermined frame rate along the route 98 (see FIG. 3) to acquire the actual video image 206 (see FIG. 14) as the live view image.

Figure 21:
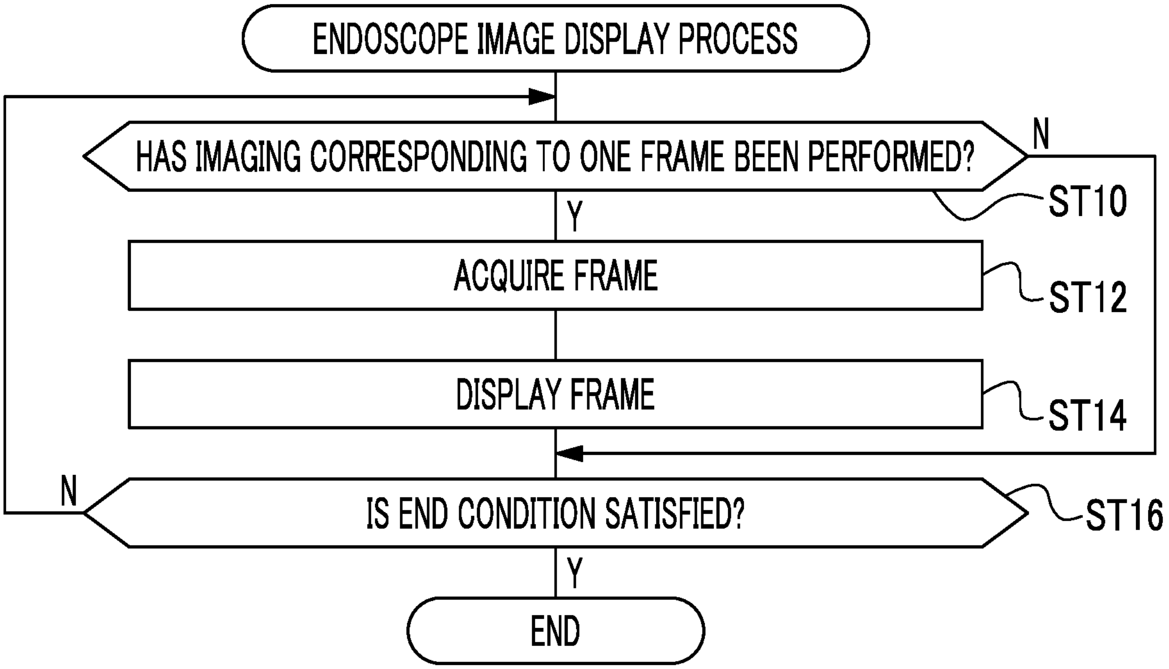
FIG. 21 is a flowchart illustrating an example of a flow of an endoscope image display process.

In the endoscope image display process illustrated in FIG. 21, first, in Step ST10, the first control unit 148A determines whether or not imaging corresponding to one frame has been performed by the camera 46. In a case in which the imaging corresponding to one frame has not been performed by the camera 46 in Step ST10, the determination result is "No", and the endoscope image display process proceeds to Step ST16. In a case in which the imaging corresponding to one frame has been performed by the camera 46 in Step ST10, the determination result is "Yes", and the endoscope image display process proceeds to Step ST12.

In Step ST12, the first control unit 148A acquires the frame 208 obtained by performing the imaging corresponding to one frame with the camera 46 (see FIG. 14). After the process in Step ST12 is performed, the endoscope image display process proceeds to Step ST14.

In Step ST14, the first control unit 148A displays the frame 208 acquired in Step ST12 on the screen 22 (see FIG. 14). After the process in Step ST14 is performed, the endoscope image display process proceeds to Step ST16.

In Step ST16, the first control unit 148A determines whether or not a condition for ending the endoscope image display process (hereinafter, referred to as an "endoscope image display process end condition") has been satisfied. An example of the endoscope image display process end condition is a condition in which the receiving device 68 has received an instruction to end the endoscope image display process. In a case in which the endoscope image display process end condition has not been satisfied in Step ST16, the determination result is "No", and the endoscope image display process proceeds to Step ST10. In a case in which the endoscope image display process end condition has been satisfied in Step ST16, the determination result is "Yes", and the endoscope image display process ends.

Next, an example of a flow of the navigation video image display process performed by the processor 148 of the display control device 66 in a case in which an instruction to start the execution of the navigation video image display process is received by the receiving device 68 will be described with reference to FIG. 22.

Figure 22:
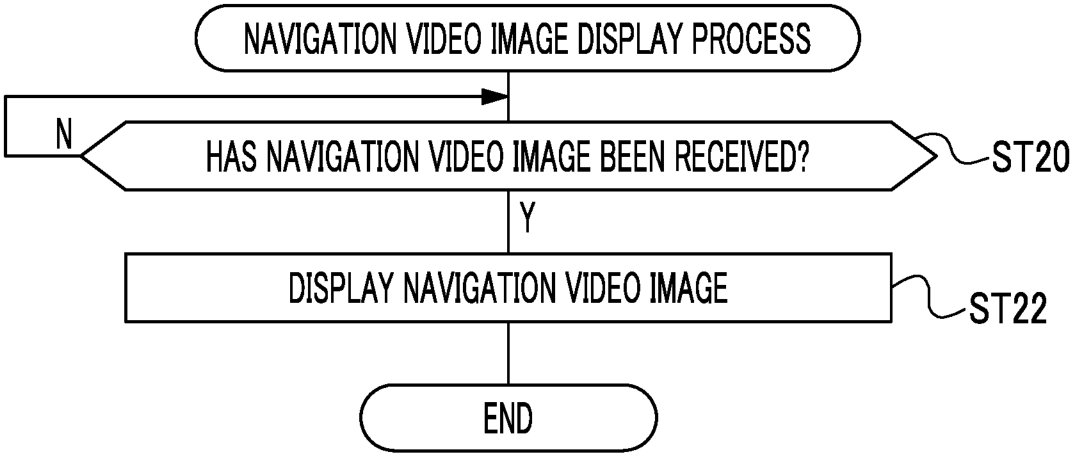
FIG. 22 is a flowchart illustrating an example of a flow of a navigation video image display process.
Figure 26:
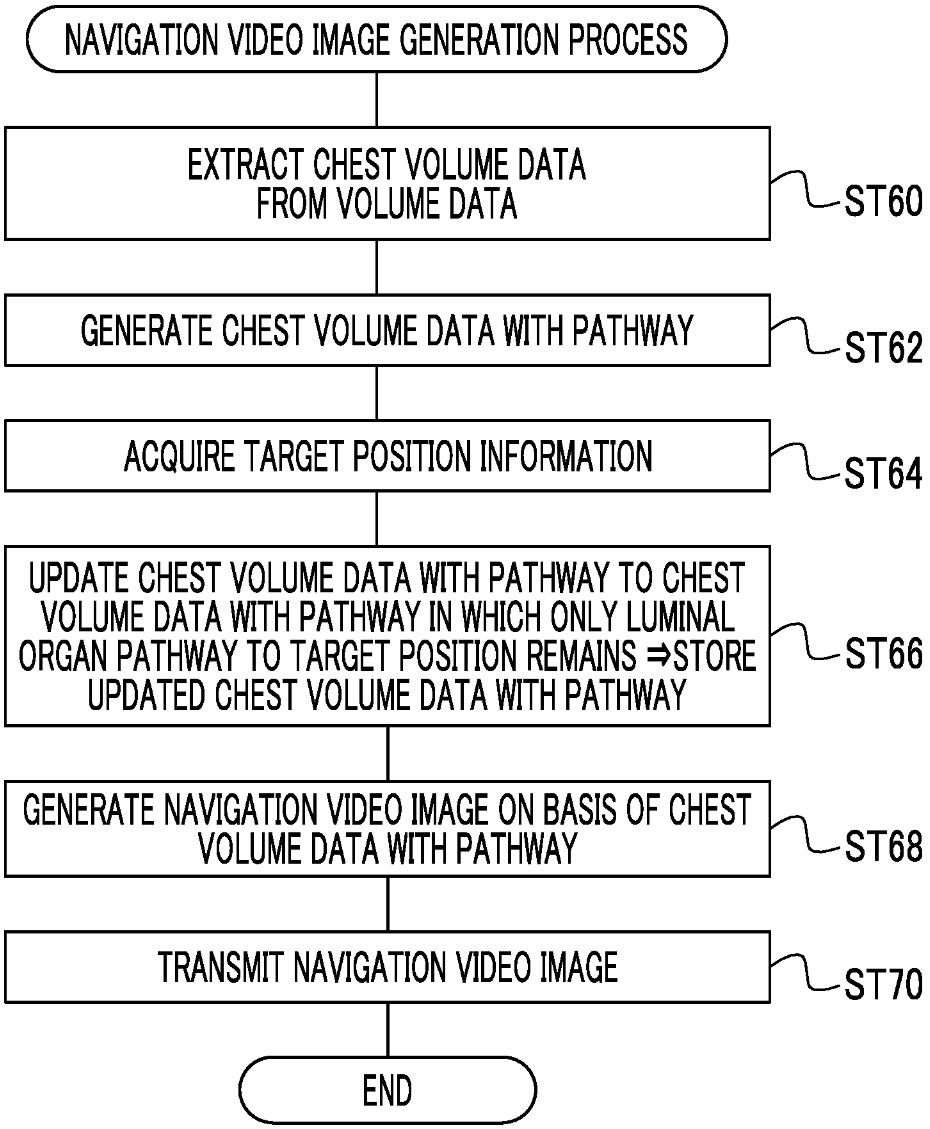
FIG. 26 is a flowchart illustrating an example of a flow of a navigation video image generation process.

In the navigation video image display process illustrated in FIG. 22, first, in Step ST20, the first receiving unit 148B determines whether or not the communication module 156 (see FIGS. 6 and 7) has received the navigation video image 192 transmitted from the second transmitting unit 164C of the server 70 by performing a process in Step ST70 included in the navigation video image generation process illustrated in FIG. 26. In a case in which the communication module 156 has not received the navigation video image 192 transmitted from the second transmitting unit 164C of the server 70 in Step ST20, the determination result is "No", and the determination in Step ST20 is performed again. In a case in which the communication module 156 has received the navigation video image 192 transmitted from the second transmitting unit 164C of the server 70 in Step ST20, the determination result is "Yes", and the navigation video image display process proceeds to Step ST22.

In Step ST22, the second control unit 148C displays the navigation video image 192 received by the communication module 156 on the screen 212 (see FIG. 14). After the process in Step ST22 is performed, the navigation video image display process ends.

Next, an example of a flow of the actual ultrasound image display process performed by the processor 148 of the display control device 66 in a case in which the receiving device 68 receives an instruction to start the execution of the actual ultrasound image display process will be described with reference to FIG. 23.

Figure 23:
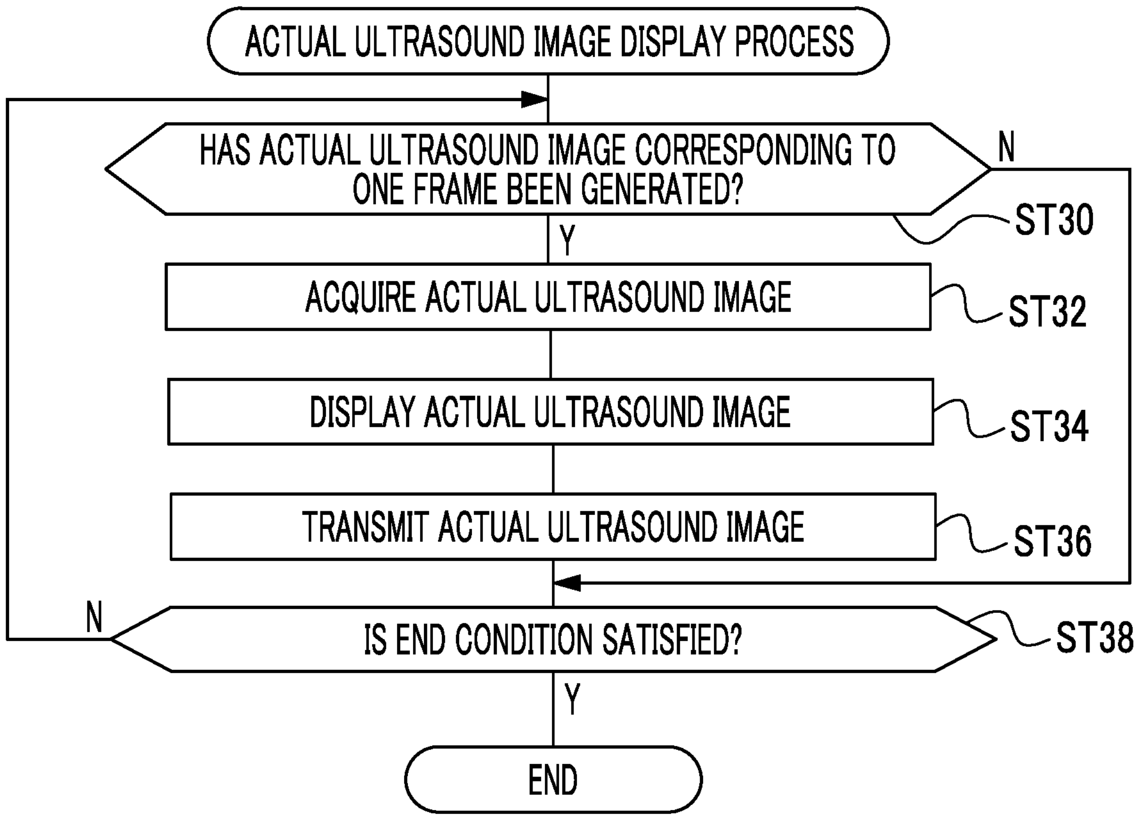
FIG. 23 is a flowchart illustrating an example of a flow of an actual ultrasound image display process.

In the actual ultrasound image display process illustrated in FIG. 23, first, in Step ST30, the third control unit 148D determines whether or not the actual ultrasound image 30 corresponding to one frame has been generated by the ultrasound processing device 64. In a case in which the actual ultrasound image 30 corresponding to one frame has not been generated by the ultrasound processing device 64 in Step ST30, the determination result is "No", and the actual ultrasound image display process proceeds to Step ST38. In a case in which the actual ultrasound image 30 corresponding to one frame has been generated by the ultrasound processing device 64 in Step ST30, the determination result is "Yes", and the actual ultrasound image display process proceeds to Step ST32.

In Step ST32, the third control unit 148D acquires the actual ultrasound image 30 corresponding to one frame from the ultrasound processing device 64. After the process in Step ST32 is performed, the actual ultrasound image display process proceeds to Step ST34.

In Step ST34, the third control unit 148D displays the actual ultrasound image 30 acquired in Step ST32 on the screen 24 (see FIG. 16). After the process in Step ST34 is performed, the actual ultrasound display process proceeds to Step ST36.

In Step ST36, the first transmitting unit 148E transmits the actual ultrasound image 30 acquired in Step ST32 to the server 70 (see FIG. 16). After the process in Step ST36 is performed, the actual ultrasound display process proceeds to Step ST38.

In Step ST38, the third control unit 148D determines whether or not a condition for ending the actual ultrasound image display process (hereinafter, referred to as an "actual ultrasound image display process end condition") has been satisfied. An example of the actual ultrasound image display process end condition is a condition in which the receiving device 68 has received an instruction to end the actual ultrasound image display process. In a case in which the actual ultrasound image display process end condition has not been satisfied in Step ST38, the determination result is "No", and the actual ultrasound image display process proceeds to Step ST30. In a case in which the actual ultrasound image display process end condition has been satisfied in Step ST38, the determination result is "Yes", and the actual ultrasound image display process ends.

Next, an example of a flow of the virtual ultrasound image display process performed by the processor 148 of the display control device 66 in a case in which the receiving device 68 receives an instruction to start the execution of the virtual ultrasound image display process will be described with reference to FIG. 24.

Figure 24:
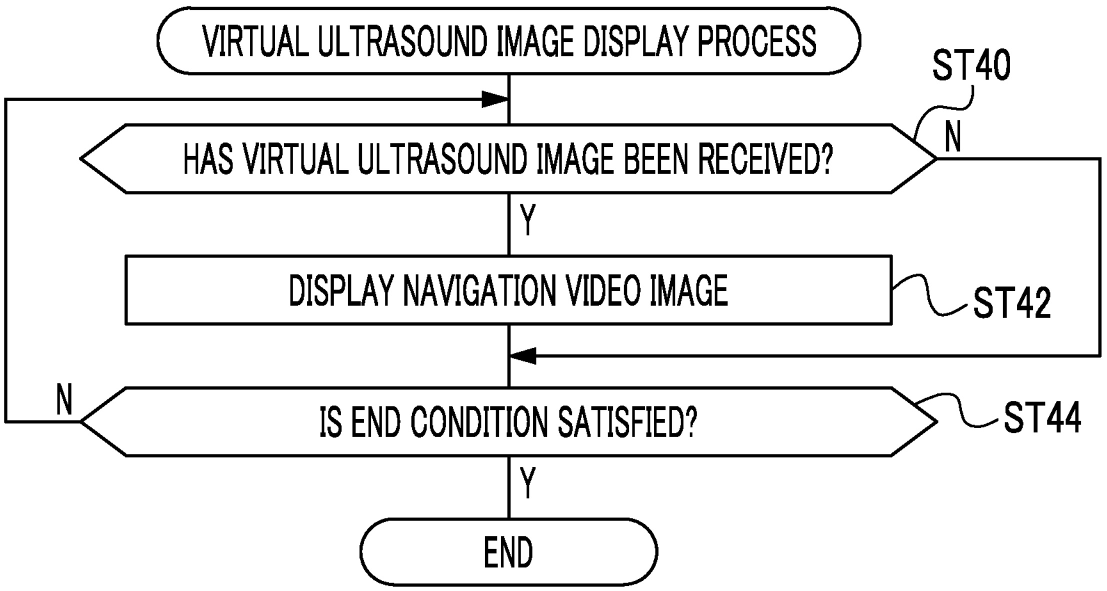
FIG. 24 is a flowchart illustrating an example of a flow of a virtual ultrasound image display process.
Figure 27:
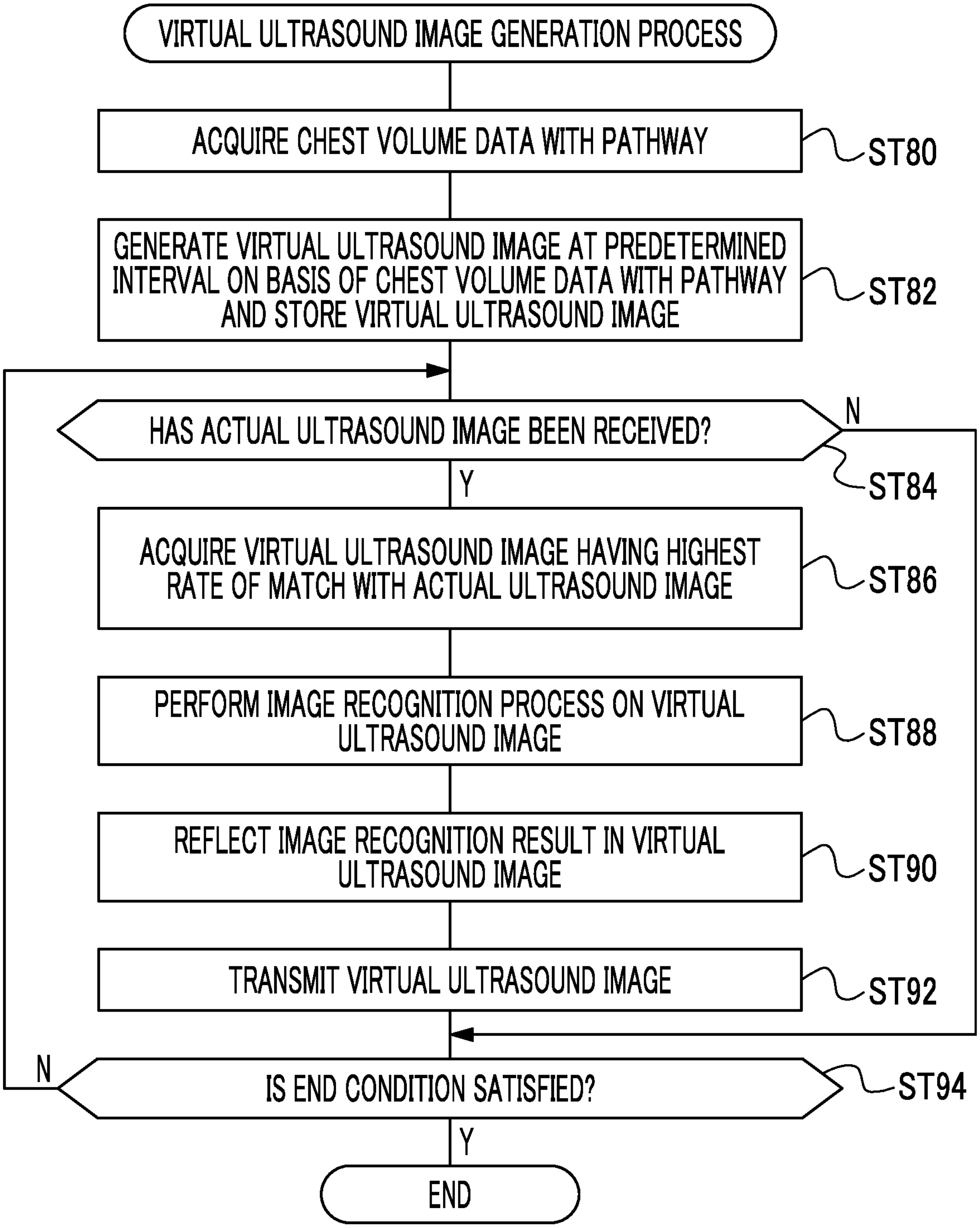
FIG. 27 is a flowchart illustrating an example of a flow of a virtual ultrasound image generation process.

In the virtual ultrasound image display process illustrated in FIG. 24, first, in Step ST40, the second receiving unit 148F determines whether or not the communication module 156 (see FIGS. 6 and 7) has received the virtual ultrasound image 32 transmitted from the first transmitting and receiving unit 164E of the server 70 by performing a process in Step ST92 included in the virtual ultrasound image generation process illustrated in FIG. 27. In a case in which the communication module 156 has not received the virtual ultrasound image 32 transmitted from the first transmitting and receiving unit 164E of the server 70 in Step ST40, the determination result is "No", and the virtual ultrasound image display process proceeds to Step ST44. In a case in which the communication module 156 has received the virtual ultrasound image 32 transmitted from the first transmitting and receiving unit 164E of the server 70 in Step ST40, the determination result is "Yes", and the virtual ultrasound image display process proceeds to Step ST42.

In Step ST42, the fourth control unit 148G displays the virtual ultrasound image 32 received by the communication module 156 on the screen 26 (see FIG. 18). After the process in Step ST42 is performed, the virtual ultrasound image display process proceeds to Step ST44.

In Step ST44, the fourth control unit 148G determines whether or not a condition for ending the virtual ultrasound image display process (hereinafter, referred to as a "virtual ultrasound image display process end condition") has been satisfied. An example of the virtual ultrasound image display process end condition is a condition in which the receiving device 68 has received an instruction to end the virtual ultrasound image display process. In a case in which the virtual ultrasound image display process end condition has not been satisfied in Step ST44, the determination result is "No", and the virtual ultrasound image display process proceeds to Step ST40. In a case in which the virtual ultrasound image display process end condition has been satisfied in Step ST44, the determination result is "Yes", and the virtual ultrasound image display process ends.

Next, an example of a flow of the support information display process performed by the processor 148 of the display control device 66 in a case in which the receiving device 68 receives an instruction to start the execution of the support information display process will be described with reference to FIG. 25.

Figure 25:
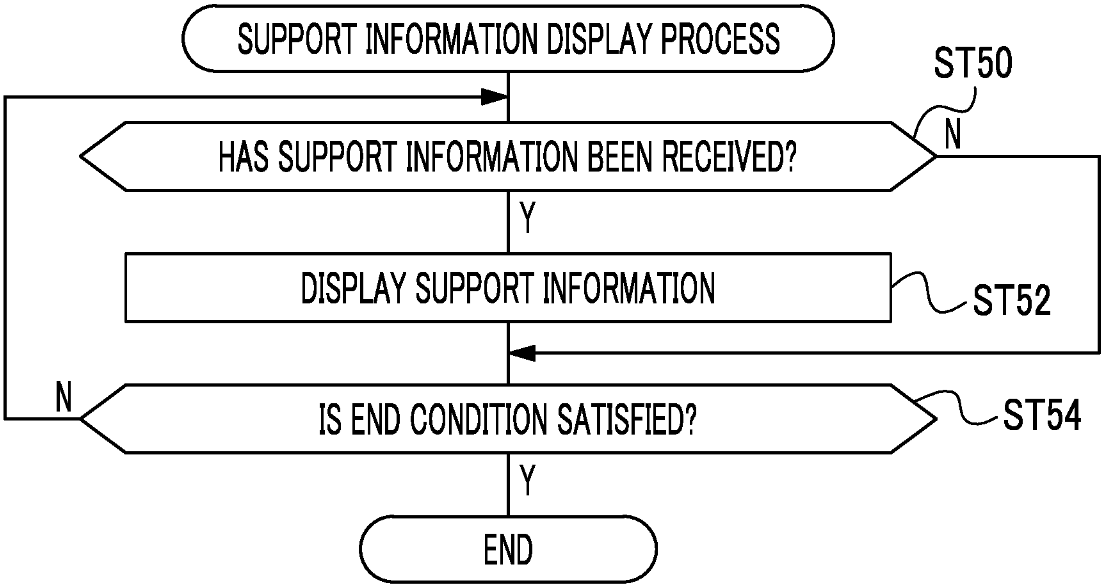
FIG. 25 is a flowchart illustrating an example of a flow of a support information display process.
Figure 28:
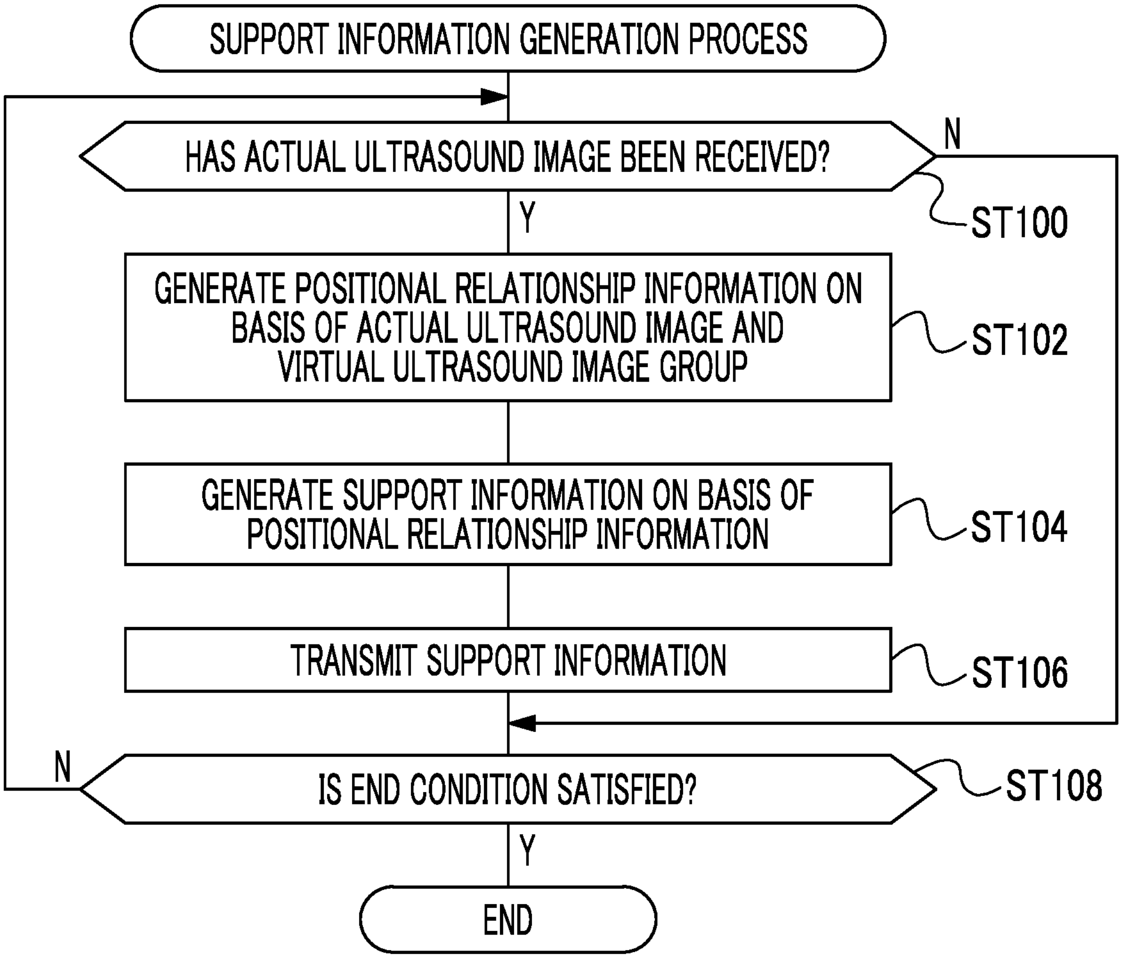
FIG. 28 is a flowchart illustrating an example of a flow of a support information generation process.

In the support information display process illustrated in FIG. 25, first, in Step ST50, the third receiving unit 148H determines whether or not the communication module 156 (see FIGS. 6 and 7) has received the support information 238 transmitted from the second transmitting and receiving unit 164I of the server 70 by performing a process in Step ST106 included in the support information generation process illustrated in FIG. 28. In a case in which the communication module 156 has not received the support information 238 transmitted from the second transmitting and receiving unit 164I of the server 70 in Step ST50, the determination result is "No", and the support information display process proceeds to Step ST54. In a case in which the communication module 156 has received the support information 238 transmitted from the second transmitting and receiving unit 164I of the server 70 in Step ST50, the determination result is "Yes", and the support information display process proceeds to Step ST52.

In Step ST52, the fifth control unit 148I displays the support information 238 received by the communication module 156 on the display device 14 (see FIG. 20). After the process in Step ST52 is performed, the support information display process proceeds to Step ST54.

In Step ST54, the fifth control unit 148I determines whether or not a condition for ending the support information display process (hereinafter, referred to as a "support information display process end condition") has been satisfied. An example of the support information display process end condition is a condition in which the receiving device 68 has received an instruction to end the support information display process. In a case in which the support information display process end condition has not been satisfied in Step ST54, the determination result is "No", and the support information display process proceeds to Step ST50. In a case in which the support information display process end condition has been satisfied in Step ST54, the determination result is "Yes", and the support information display process ends.

Next, an example of a flow of the navigation video image generation process performed by the processor 164 of the server 70 in a case in which the receiving device 68 or 76 receives an instruction to start the execution of the navigation video image generation process will be described with reference to FIG. 26.

In the navigation video image generation process illustrated in FIG. 26, first, in Step ST60, the image processing unit 164A extracts the chest volume data 178 from the volume data 176 stored in the NVM 168 (see FIG. 10). After the process in Step ST60 is performed, the navigation video image generation process proceeds to Step ST62.

In Step ST62, the image processing unit 164A generates the chest volume data 184 with a pathway on the basis of the chest volume data 178 extracted from the volume data 176 in Step ST60 (see FIG. 10). After the process in Step ST62 is performed, the navigation video image generation process proceeds to Step ST64.

In Step ST64, the image processing unit 164A acquires the target position information 188 from the NVM 168 (see FIG. 11). After the process in Step ST64 is performed, the navigation video image generation process proceeds to Step ST66.

In Step ST66, the image processing unit 164A updates the chest volume data 184 with a pathway to the chest volume data 184 with a pathway in which only the luminal organ pathway 186A remains with reference to the target position information 188 acquired in Step ST64 and stores the updated chest volume data 184 with a pathway in the NVM 168 (see FIG. 11). After the process in Step ST66 is performed, the navigation video image generation process proceeds to Step ST68.

In Step ST68, the first generation unit 164B acquires the chest volume data 184 with a pathway stored in the NVM 168 in Step ST66 and generates the navigation video image 192 on the basis of the acquired chest volume data 184 with a pathway (see FIG. 12). After the process in Step ST68 is performed, the navigation video image generation process proceeds to Step ST70.

In Step ST70, the second transmitting unit 164C transmits the navigation video image 192 generated in Step ST68 to the display control device 66 (see FIG. 13). After the process in Step ST70 is performed, the navigation video image generation process ends.

Next, an example of a flow of the virtual ultrasound image generation process performed by the processor 164 of the server 70 in a case in which the receiving device 68 or 76 receives an instruction to start the execution of the virtual ultrasound image generation process will be described with reference to FIG. 27.

In the virtual ultrasound image generation process illustrated in FIG. 27, first, in Step ST80, the second generation unit 164D acquires the chest volume data 184 with a pathway (that is, the chest volume data 184 with a pathway stored in the NVM 168 by performing the process in Step ST66 included in the navigation video image generation process illustrated in FIG. 26) from the NVM 168 (see FIG. 15). After the process in Step ST80 is performed, the virtual ultrasound image generation process proceeds to Step ST82.

In Step ST82, the second generation unit 164D generates the virtual ultrasound image 214 at a predetermined interval on the basis of the chest volume data 184 with a pathway acquired in Step ST80 and stores the generated virtual ultrasound image 214 in the NVM 168 (see FIG. 15). After the process in Step ST82 is performed, the virtual ultrasound image generation process proceeds to Step ST84.

In Step ST84, the first transmitting and receiving unit 164E determines whether or not the communication module 162 (see FIG. 7) has received the actual ultrasound image 30 transmitted from the first transmitting unit 148E by performing the process in Step ST36 included in the actual ultrasound image display process illustrated in FIG. 23. In a case in which the communication module 162 has not received the actual ultrasound image 30 in Step ST84, the determination result is "No", and the virtual ultrasound image generation process proceeds to Step ST94. In a case in which the communication module 162 has received the actual ultrasound image 30 in Step ST84, the determination result is "Yes", and the virtual ultrasound image generation process proceeds to Step ST86.

In Step ST86, the acquisition unit 164F acquires the virtual ultrasound image 214 having the highest rate of match with the actual ultrasound image 30 received by the communication module 162 from the virtual ultrasound image group 224 (see FIG. 17). After the process in Step ST86 is performed, the virtual ultrasound image generation process proceeds to Step ST88.

In Step ST88, the image recognition unit 164G performs the AI-type image recognition process on the virtual ultrasound image 214 acquired in Step ST86 to specify the region 164G1 (see FIG. 17). After the process in Step ST88 is performed, the virtual ultrasound image generation process proceeds to Step ST90.

In Step ST90, the processing unit 164H reflects the image recognition result (that is, the result of the image recognition process performed in Step ST88) in the virtual ultrasound image 214 acquired in Step ST86 to generate the virtual ultrasound image 32 (see FIG. 17). Here, the reflection of the image recognition result in the virtual ultrasound image 214 means, for example, a process of superimposing the image recognition result mark 230 on the virtual ultrasound image 214 (see FIG. 17). After the process in Step ST90 is performed, the virtual ultrasound image generation process proceeds to Step ST92.

In Step ST92, the first transmitting and receiving unit 164E transmits the virtual ultrasound image 32 generated in Step ST90 to the display control device 66 (see FIG. 18). After the process in Step ST92 is performed, the virtual ultrasound image generation process proceeds to Step ST94.

In Step ST94, the first transmitting and receiving unit 164E determines whether or not a condition for ending the virtual ultrasound image generation process (hereinafter, referred to as a "virtual ultrasound image generation process end condition") has been satisfied. An example of the virtual ultrasound image generation process end condition is a condition in which the receiving device 68 or 76 has received an instruction to end the virtual ultrasound image generation process. In a case in which the virtual ultrasound image generation process end condition has not been satisfied in Step ST94, the determination result is "No", and the virtual ultrasound image generation process proceeds to Step ST84. In a case in which the virtual ultrasound image generation process end condition has been satisfied in Step ST94, the determination result is "Yes", and the virtual ultrasound image generation process ends.

Next, an example of a flow of the support information generation process performed by the processor 164 of the server 70 in a case in which the receiving device 68 or 76 receives an instruction to start the execution of the support information generation process will be described with reference to FIG. 28. In addition, the flow of the support information generation process illustrated in FIG. 28 is an example of an "information processing method" according to the technology of the present disclosure.

In the support information generation process illustrated in FIG. 28, first, in Step ST100, the second transmitting and receiving unit 164I determines whether or not the communication module 162 (see FIG. 7) has received the actual ultrasound image 30 transmitted from the first transmitting unit 148E by performing the process in Step ST36 included in the actual ultrasound image display process illustrated in FIG. 23. In a case in which the communication module 162 has not received the actual ultrasound image 30 in Step ST100, the determination result is "No", and the support information generation process proceeds to Step ST108. In a case in which the communication module 162 has received the actual ultrasound image 30 in Step ST100, the determination result is "Yes", and the support information generation process proceeds to Step ST102.

In Step ST102, the third generation unit 164J generates the positional relationship information 234 on the basis of the actual ultrasound image 30 received by the communication module 162 and the virtual ultrasound image group 224 (see FIG. 19). After the process in Step ST102 is performed, the support information generation process proceeds to Step ST104.

In Step ST104, the third generation unit 164J generates the support information 238 on the basis of the positional relationship information 234 generated in Step ST102 (see FIG. 19). After the process in Step ST104 is performed, the support information generation process proceeds to Step ST106.

In Step ST106, the second transmitting and receiving unit 164I transmits the support information 238 generated in Step ST104 to the display control device 66 (see FIG. 20). After the process in Step ST106 is performed, the support information generation process proceeds to Step ST108.

In Step ST108, the second transmitting and receiving unit 164I determines whether or not a condition for ending the support information generation process (hereinafter, referred to as a "support information generation process end condition") has been satisfied. An example of the support information generation process end condition is a condition in which the receiving device 68 or 76 has received an instruction to end the support information generation process. In a case in which the support information generation process end condition has not been satisfied in Step ST108, the determination result is "No", and the support information generation process proceeds to Step ST100. In a case in which the support information generation process end condition has been satisfied in Step ST108, the determination result is "Yes", and the support information generation process ends.

As described above, in the endoscope system 10, the positional relationship between the position 108 and the position 100 is specified on the basis of the actual ultrasound image 30 and the specific virtual ultrasound image 214A. The specific virtual ultrasound image 214A is the virtual ultrasound image 214 corresponding to the target position 190. The virtual ultrasound image 214 corresponding to the target position 190 means a virtual ultrasound image 214 which corresponds to the actual ultrasound image 30 obtained in a case in which the position 108 and the position 100 illustrated in FIG. 3 are matched with each other, among a plurality of virtual ultrasound images 214. Further, the position 108 is the position of the distal end part 38 of the bronchoscope 18. For example, the position 108 is a position facing the position where the puncture needle 52B in the treatment tool opening 50 (see FIG. 2) protrudes in the luminal organ inner wall surface 102. In other words, the position 108 is a position where the protruding direction of the puncture needle 52B and the luminal organ inner wall surface 102 intersect each other. On the other hand, the position 100 is the position where the lymph node 104 is present outside the luminal organ 84 (outside the bronchus 96 in the example illustrated in FIG. 3) in the luminal organ inner wall surface 102. In other words, the position 100 is a position punctured by the puncture needle 52B in the luminal organ inner wall surface 102 in a case in which the central portion 104A of the tube of the lymph node 104 is pricked by the puncture needle 52B.

Therefore, the specification of the positional relationship between the position 108 and the position 100 on the basis of the actual ultrasound image 30 and the specific virtual ultrasound image 214A makes it possible to easily perform positioning between the distal end part 38 of the bronchoscope 18 and the lymph node 104 (that is, an operation of aligning the position 108 with the position 100). For example, it is possible to easily perform the operation of aligning the position 108 with the position 100 as compared to a case in which the doctor 16 performs the operation of aligning the position 108 with the position 100 with reference to only the actual ultrasound image 30. As a result, it is possible to easily puncture the lymph node 104 with the puncture needle 52B. For example, it is possible to easily puncture the lymph node 104 with the puncture needle 52B as compared to the case in which the doctor 16 performs the operation of aligning the position 108 with the position 100 with reference to only the actual ultrasound image 30.

In addition, in the endoscope system 10, the actual ultrasound image 30 is compared with the specific virtual ultrasound image 214A to calculate the distance 232 (see FIG. 19) as the amount of deviation between the position 108 and the position 100. Further, the positional relationship between the position 108 and the position 100 is defined on the basis of the distance 232. Therefore, the doctor 16 can operate the bronchoscope 18 to position the distal end part 38 of the bronchoscope 18 and the lymph node 104 such that the distance 232 is reduced.

In addition, in the endoscope system 10, in a case in which the position 108 and the position 100 are matched with each other, notification is made that the position 108 and the position 100 are matched with each other. For example, the notification information 238B is displayed on the screen 24 to notify that the position 108 and the position 100 are matched with each other. This makes it possible for the user to perceive that the position 108 and the position 100 are matched with each other.

In addition, in the endoscope system 10, in a case in which the position 108 and the position 100 are not matched with each other, the guidance information 238A is presented to the user as information for guiding the position 108 to the position 100. For example, the guidance information 238A is displayed on the screen 24 to present the guidance information 238A to the user. Therefore, it is possible to efficiently perform the positioning between the distal end part 38 of the bronchoscope 18 and the lymph node 104 (that is, the operation of aligning the position 108 with the position 100). For example, it is possible to efficiently perform the positioning between the distal end part 38 of the bronchoscope 18 and the lymph node 104 as compared to the case in which the doctor 16 performs the operation of aligning the position 108 with the position 100 with reference to only the actual ultrasound image 30.

Further, in the endoscope system 10, the actual ultrasound image 30 is displayed on the screen 24 (see FIGS. 1, 16, 18, and 20). This makes it possible for the user to ascertain the positional relationship between the distal end part 38 of the bronchoscope 18 and the lymph node 104.

In addition, in the endoscope system 10, the image recognition process is performed on the virtual ultrasound image 214, and the result of the image recognition process is superimposed as the image recognition result mark 230 on the virtual ultrasound image 214 to generate the virtual ultrasound image 32 (see FIG. 17). The image recognition result mark 230 is given to the region 164G1 in which the lymph node included in the virtual ultrasound image 214 is present. Then, the virtual ultrasound image 32 is displayed on the screen 26 (see FIGS. 18 and 20). This makes it possible for the user to ascertain the region in which the lymph node is present through the virtual ultrasound image 32.

Further, in the endoscope system 10, the virtual ultrasound image 32 and the actual ultrasound image 30 are displayed on the display device 14 to be comparable with each other. This makes it possible for the doctor 16 perform the operation of aligning the position 108 with the position 100 while referring to the virtual ultrasound image 32 and the actual ultrasound image 30.

In addition, in the endoscope system 10, the virtual ultrasound image 214 having the highest rate of match with the actual ultrasound image 30 is selected from the virtual ultrasound image group 224, and the virtual ultrasound image 32 obtained by processing the selected virtual ultrasound image 214 and the actual ultrasound image 30 are displayed on the display device 14 to be comparable with each other. This makes it possible for the doctor 16 to perform the operation of aligning the position 108 with the position 100 while referring to the actual ultrasound image 30 and the virtual ultrasound image 32 similar to the actual ultrasound image 30.

Further, in the endoscope system 10, the navigation video image 192 and the actual ultrasound image 30 are displayed on the display device 14 to be comparable with each other (see FIG. 16). This makes it possible for the doctor 16 to perform the operation of aligning the position 108 with the position 100 while referring to the navigation video image 192 and the actual ultrasound image 30.

In addition, in the endoscope system 10, the navigation video image 192 is generated as a video image for guiding the movement of the distal end part 38 (see FIGS. 2 and 3) of the bronchoscope 18, and the navigation video image 192 and the actual ultrasound image 30 are displayed on the display device 14 to be comparable with each other (see FIG. 16). This makes it possible to increase convenience for the doctor 16 who is not confident in how to move the distal end part 38 of the bronchoscope 18. For example, it is possible to increase convenience for the doctor 16 who is not confident in how to move the distal end part 38 of the bronchoscope 18, as compared to a case in which the navigation video image 192 is not displayed on the display device 14, but only the actual ultrasound image 30 is displayed on the display device 14.

Further, in the endoscope system 10, the frame 198 on which the aiming mark 204 has been superimposed is displayed on the display device 14. The position having the aiming mark 204 given thereto in the frame 198 is a position which corresponds to the position where the ultrasonic waves are emitted from the ultrasound probe 48 in a real space in the frame 198. Therefore, this makes it possible for the doctor 16 to perceive the position where the ultrasonic waves are emitted.

In addition, in the endoscope system 10, in a case in which the frame 198 on which the aiming mark 204 has been superimposed is displayed on the screen 212, the virtual ultrasound image 32 generated on the basis of the actual ultrasound image 30 by emitting the ultrasonic waves to the position specified from the aiming mark 204 is displayed on the screen 26 (see FIGS. 17 and 18). This means that a virtual ultrasound image showing the aspect of the observation target region 106 with respect to the position specified from the aiming mark 204 is displayed as the virtual ultrasound image 32 on the screen 26. Therefore, this makes it possible for the user to ascertain which position of the frame 198 the virtual ultrasound image 32 is related to and then to observe the virtual ultrasound image 32 and the frame 198.

In addition, in the above-described embodiment, the actual ultrasound image 30 generated in the B-mode is given as an example. However, the technology of the present disclosure is not limited thereto, and an actual ultrasound image generated in the Doppler mode may be applied instead of the actual ultrasound image 30. In this case, the user can specify the positional relationship between the position 108 and the position 100 with reference to a blood vessel (for example, the display of a blood flow) included in the actual ultrasound image.

Further, an image, which is based on the actual ultrasound image generated in the Doppler mode (that is, an ultrasound image including a blood flow) and the actual ultrasound image 30 generated in the B-mode (that is, an ultrasound image in which the intensity of the reflected waves obtained by the reflection of the ultrasonic waves from the observation target region 106 is represented by brightness), may be applied instead of the actual ultrasound image 30. An example of the image based on the actual ultrasound image generated in the Doppler mode and the actual ultrasound image 30 generated in the B-mode is a superimposed image obtained by superimposing one of the actual ultrasound image generated in the Doppler mode and the actual ultrasound image 30 generated in the B-mode on the other actual ultrasound image. The superimposed image obtained in this way is displayed on the display device 14 in the same manner as in the above-described embodiment. This makes it possible for the user to specify the positional relationship between the position 108 and the position 100 with reference to the blood vessel included in the ultrasound image generated in the Doppler mode and the lymph node included in the actual ultrasound image 30 generated in the B-mode.

First Modification Example

Figure 29:
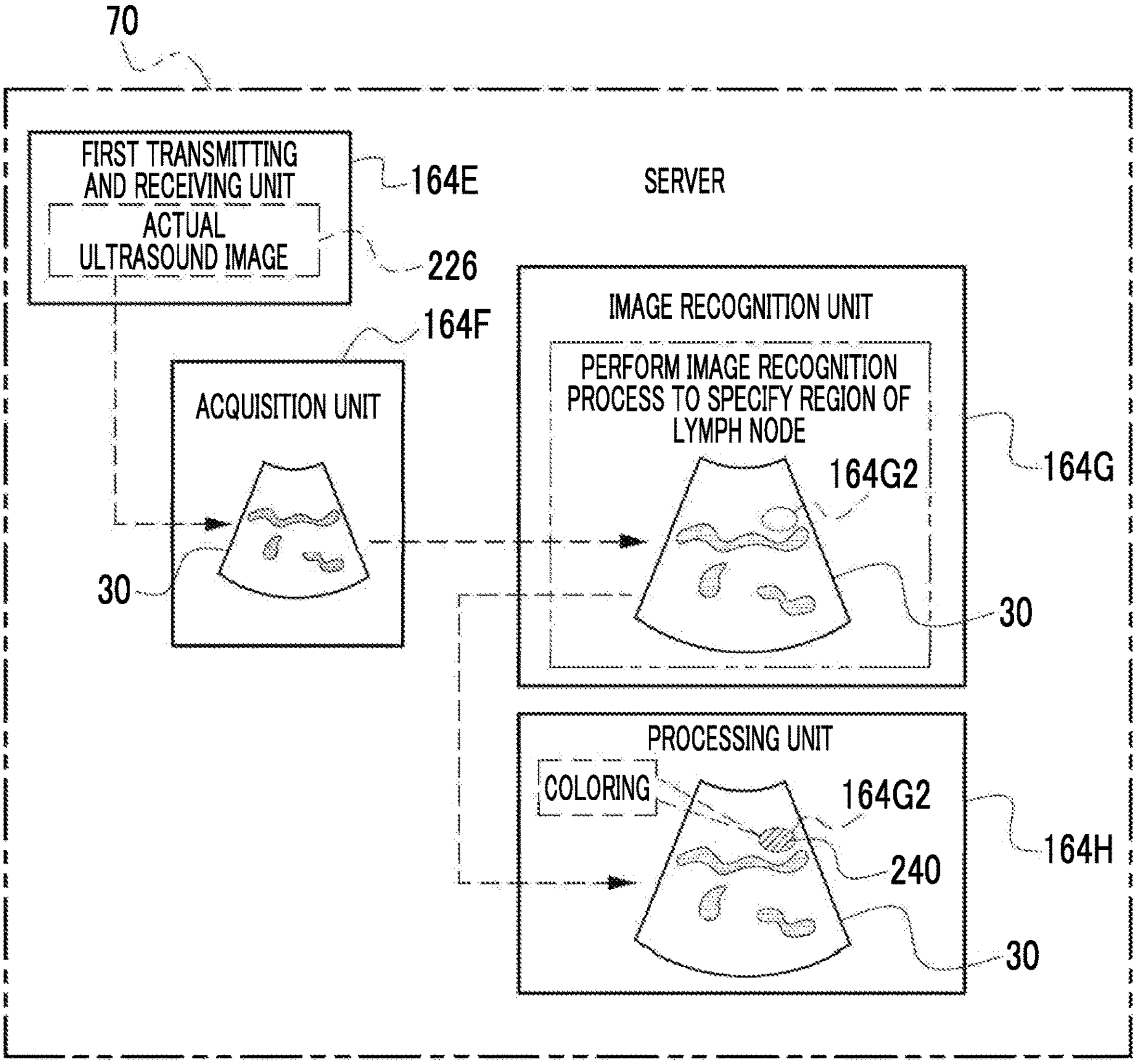
FIG. 29 is a conceptual diagram illustrating an example of content of processes of a first transmitting and receiving unit, an image recognition unit, and a processing unit of a server according to a first modification example.

In the above-described embodiment, the aspect in which the image recognition process is performed on the virtual ultrasound image 214 has been described. However, the technology of the present disclosure is not limited to this aspect. For example, as illustrated in FIG. 29, the image recognition unit 164G may perform the image recognition process on the actual ultrasound image 30 acquired by the acquisition unit 164F in the same manner as in the above-described embodiment. The image recognition process is performed on the actual ultrasound image 30 to specify a region 164G2 in which the lymph node included in the actual ultrasound image 30 is present.

The processing unit 164H superimposes an image recognition result mark 240 on the actual ultrasound image 30 to process the actual ultrasound image 30. The image recognition result mark 240 is a mark obtained by coloring the region 164G2 in the actual ultrasound image 30 in the same manner as in the above-described embodiment. The actual ultrasound image 30 obtained in this way is displayed on the screen 24. Therefore, the user can ascertain the region in which the lymph node is present through the actual ultrasound image 30.

Second Modification Example

In the above-described embodiment, the aspect which the support information 238 is generated on the basis of the actual ultrasound image 30 generated in the B-mode has been described. However, the technology of the present disclosure is not limited to this aspect. For example, as illustrated in FIG. 30, support information 244 may be generated on the basis of an actual ultrasound image 242 (that is, an ultrasound image obtained by superimposing an ultrasound image including a blood flow on an ultrasound image corresponding to the actual ultrasound image 30) generated in the Doppler mode.

Figure 30:
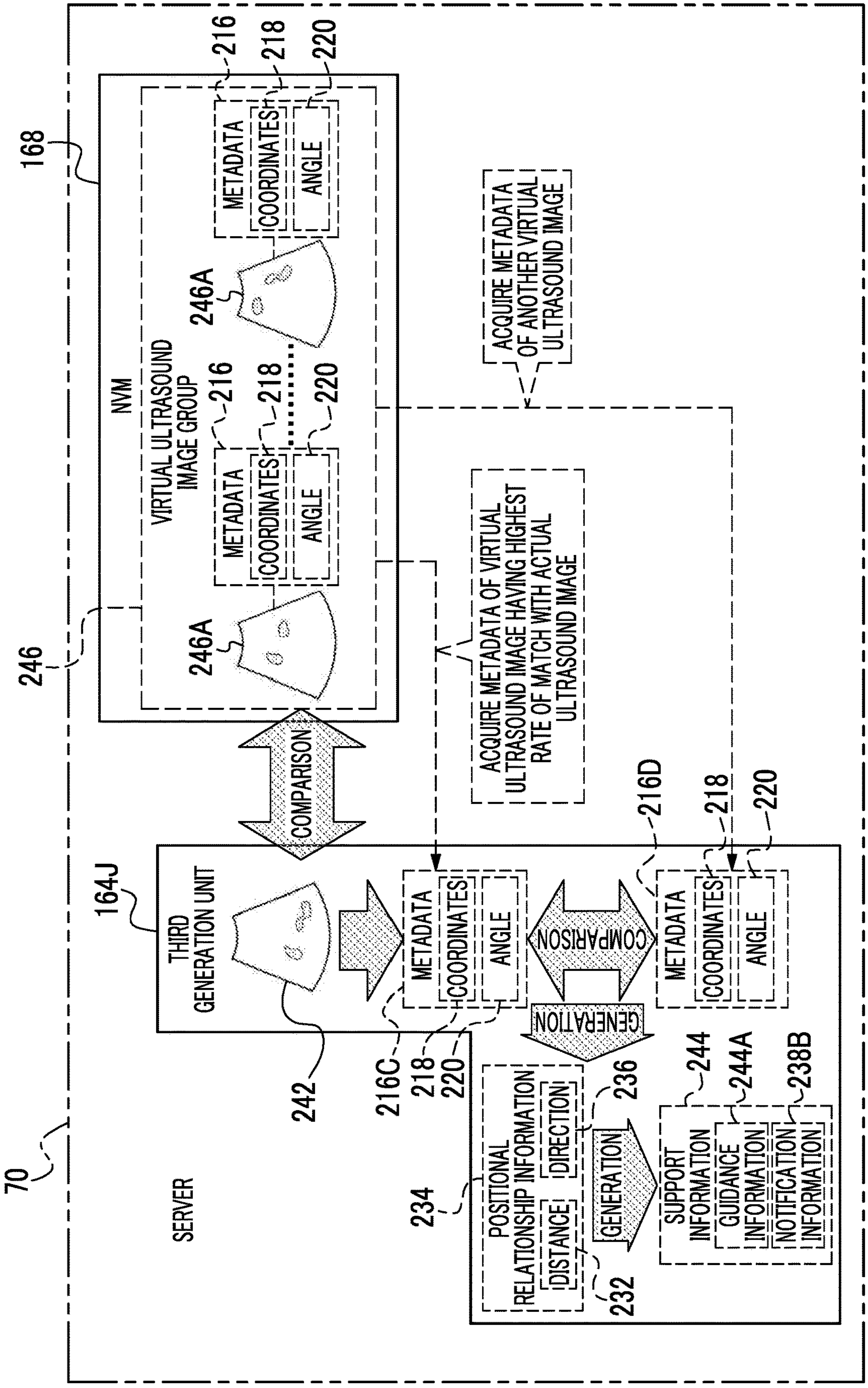
FIG. 30 is a conceptual diagram illustrating an example of content of a process of a third generation unit of a server according to a second modification example.

The example illustrated in FIG. 30 differs from the above-described embodiment in that the third generation unit 164J uses the actual ultrasound image 242 instead of the actual ultrasound image 30, a virtual ultrasound image group 246 is applied instead of the virtual ultrasound image group 224, and the third generation unit 164J generates the support information 244 instead of the support information 238.

The virtual ultrasound image group 246 differs from the virtual ultrasound image group 224 in that a virtual ultrasound image 246A is applied instead of the virtual ultrasound image 214. The virtual ultrasound image 246A differs from the virtual ultrasound image 214 in that it is a virtual image obtained as an image imitating the actual ultrasound image 242. The image imitating the actual ultrasound image 242 means an image imitating the actual ultrasound image 242 generated in the Doppler mode.

The third generation unit 164J acquires metadata 216C and metadata 216D from the virtual ultrasound image group 246. The metadata 216C is the metadata 216 given to the virtual ultrasound image 246A having the highest rate of match with the actual ultrasound image 242. The metadata 216D is the metadata 216 given to a virtual ultrasound image 246A (for example, a virtual ultrasound image 246A including any one of a plurality of lymph nodes including the lymph node 104) that is different from the virtual ultrasound image 246A to which the metadata 216C has been given.

The third generation unit 164J compares the metadata 216C with the metadata 216D to generate positional relationship information 234 in the same manner as in the above-described embodiment. Then, the third generation unit 164J generates the support information 244 on the basis of the positional relationship information 234. The support information 244 differs from the support information 238 in that it has guidance information 244A instead of the guidance information 238A. The guidance information 244A is information for guiding the position 108 to another position (that is, a position different from the position 108 in the luminal organ inner wall surface 102 (see FIG. 3)).

The fifth control unit 148I (see FIG. 20) performs a second presentation process. The second presentation process is a process of presenting the guidance information 244A to the user and then presenting the guidance information 238A to the user. The presentation of the guidance information 244A and the guidance information 238A is implemented, for example, by displaying the guidance information 244A and the guidance information 238A on the display device 14 (for example, the screen 24). In addition, the guidance information 238A may be displayed in a case in which a predetermined condition is satisfied after the guidance information 244A is displayed.

A first example of the predetermined condition is a condition in which the position 108 has been moved to a predetermined position. The predetermined position means, for example, a position where the actual ultrasound image 242 matched with the virtual ultrasound image 246A to which the metadata 216D has been given is obtained. Whether or not the position 108 has been moved to the predetermined position is specified by, for example, performing pattern matching using a plurality of actual ultrasound images 242 and/or by performing the AI-type image recognition process on the plurality of actual ultrasound images 242. A second example of the predetermined condition is a condition in which the receiving device 68 has received an instruction to start the display of the guidance information 238A. A third example of the predetermined condition is a condition in which the lymph node 104 has been included in the actual ultrasound image 242. Whether or not the lymph node 104 has been included in the actual ultrasound image 242 is specified by performing the image recognition process on the actual ultrasound image 242.

As described above, in the endoscope system 10 according to the second modification example, the guidance information 244A generated on the basis of the actual ultrasound image 242 generated in the Doppler mode and of the virtual ultrasound image 246A imitating the actual ultrasound image 242 is displayed on the display device 14. Then, the guidance information 238A generated on the basis of the actual ultrasound image 30 generated in the B-mode and of the virtual ultrasound image 214 imitating the actual ultrasound image 30 is displayed on the display device 14. Since the actual ultrasound image 242 generated in the Doppler mode is a higher-definition image than the actual ultrasound image 30 generated in the B-mode, the actual ultrasound image 242 includes a larger amount of mark information than the actual ultrasound image 30 generated in the B-mode. Therefore, the doctor 16 can accurately approach the position 100 from the position 108 with reference to the guidance information 244A generated on the basis of the actual ultrasound image 242 rather than the guidance information 238A generated based on the actual ultrasound image 30.

Meanwhile, in the Doppler mode, the processing load applied to the processor 164 is larger than that in the B-mode. In addition, the frame rate of the actual ultrasound image 242 generated in the Doppler mode is lower than that of the actual ultrasound image 30 generated in the B-mode. Therefore, for example, the Doppler mode may be switched to the B-mode after the position 108 is brought close to the position 100 to some extent (for example, the lymph node 104 is included in the actual ultrasound image 30).

This makes it possible for the user to accurately move the position 108 close to the position 100 with reference to the guidance information 244A in the Doppler mode rather than the guidance information 238A in the B-mode. Then, after the user moves the position 108 close to the position 100, the user switches the mode from the Doppler mode to the B-mode. This makes it possible for the user to align the position 108 with the position 100 with reference to the guidance information 238A in the B-mode in which the processing load applied to the processor 164 is less than that in the Doppler mode and the frame rate of the actual ultrasound image 30 is higher than that in the Doppler mode.

In the second modification example, the second presentation process performed by the fifth control unit 148I is an example of a "second presentation process" according to the technology of the present disclosure. The actual ultrasound image 242 is an example of a "first ultrasound image" according to the technology of the present disclosure. The actual ultrasound image 30 is an example of a "second ultrasound image" according to the technology of the present disclosure. The guidance information 244A is an example of "first guidance information" according to the technology of the present disclosure. The guidance information 238A is an example of "second guidance information" according to the technology of the present disclosure.

In the second modification example, the aspect in which the positional relationship between the position 108 and the position 100 is specified on the basis of the result of the comparison between the metadata 216C and the metadata 216D has been described. However, the technology of the present disclosure is not limited to this aspect. For example, pattern matching between the actual ultrasound image 242 and the virtual ultrasound image 246A may be performed to specify the positional relationship between the position 108 and the position 100. The pattern matching in this case includes, for example, a process of comparing a region of blood flow included in the actual ultrasound image 242 with a region of blood flow included in the virtual ultrasound image 246A. Then, the support information 244 including the guidance information 244A is generated on the basis of the positional relationship information 234 indicating the positional relationship specified by performing the pattern matching in this way.

Other Modification Examples

In the above-described embodiment, the aspect in which the lymph node 104 is punctured has been described. However, the technology of the present disclosure is not limited to this aspect. For example, the technology of the present disclosure is established even in a case in which ultrasonography is performed on the observation target region 106 including the lymph node 104 without puncturing the lymph node 104.

In the above-described embodiment, the lymph node 104 is given as a target (that is, an example of the "specific part" according to the technology of the present disclosure) observed through the ultrasound image. However, this is only an example, and the target observed through the ultrasound image may be a part (for example, a lymphatic vessel or a blood vessel) other than the lymph node 104.

In the above-described embodiment, the ultrasound probe 48 of the bronchoscope 18 is given as an example. However, the technology of the present disclosure is established even in a medical module that emits ultrasonic waves, such as an extracorporeal ultrasound probe. In this case, the positional relationship between the position where the medical module is present (for example, the position of the part irradiated with the ultrasonic waves) and the position where the target observed through the ultrasound image is present may be specified in the same manner as in the above-described embodiment.

In the above-described embodiment, the aspect in which the display control device 66 performs the display-control-device-side processes has been described. However, the technology of the present disclosure is not limited to this aspect. For example, the device that performs at least some of the processes included in the display-control-device-side processes may be provided outside the display control device 66. An example of the device provided outside the display control device 66 is the server 70. For example, the server 70 is implemented by cloud computing. Here, cloud computing is given as an example, but this is only an example. For example, the server 70 may be implemented by network computing such as fog computing, edge computing, or grid computing.

Here, the server 70 is given as an example of the device provided outside the display control device 66. However, this is only an example, and the device may be, for example, at least one PC and/or at least one main frame instead of the server 70. In addition, at least some of the processes included in the display-control-device-side processes may be dispersively performed by a plurality of devices including the display control device 66 and the device provided outside the display control device 66.

Further, at least some of the processes included in the display-control-device-side processes may be performed by, for example, the endoscope processing device 60, the ultrasound processing device 64, and a tablet terminal or a PC connected to the server 70.

In the above-described embodiment, the aspect in which the server 70 performs the server-side processes has been described. However, the technology of the present disclosure is not limited to this aspect. For example, at least some of the processes included in the server-side processes may be performed by a device other than the server 70 or may be dispersively performed by a plurality of devices including the server 70 and the device other than the server 70. A first example of the device other than the server 70 is the display control device 66. In addition, a second example of the device other than the server 70 is at least one PC and/or at least one main frame.

In the above-described embodiment, the aspect in which the support information 238 is displayed in a message format has been described. However, the technology of the present disclosure is not limited to this aspect. The support information 238 may be presented by voice.

In the above-described embodiment, the aspect in which the display-control-device-side programs 172 are stored in the NVM 152 and the server-side programs 174 are stored in the NVM 168 has been described. However, the technology of the present disclosure is not limited to this aspect. For example, the display-control-device-side programs 172 and the server-side programs 174 (hereinafter, referred to as "programs") may be stored in a portable storage medium such as an SSD or a USB memory. The storage medium is a non-transitory computer-readable storage medium. The programs stored in the storage medium are installed in the computer 72 and/or the computer 144. The processor 148 and/or the processor 164 performs the display-control-device-side processes and the server-side processes (hereinafter, referred to as "various processes") according to the programs.

In the above-described embodiment, the computer 72 and/or the computer 144 is given as an example. However, the technology of the present disclosure is not limited thereto, and a device including an ASIC, an FPGA, and/or a PLD may be applied instead of the computer 72 and/or the computer 144. In addition, a combination of a hardware configuration and a software configuration may be used instead of the computer 72 and/or the computer 144.

The following various processors can be used as hardware resources for performing various processes described in the above-described embodiment. An example of the processor is a processor which is a general-purpose processor that executes software, that is, a program, to function as the hardware resources performing various processes. In addition, an example of the processor is a dedicated electronic circuit which is a processor having a dedicated circuit configuration designed to perform a specific process, such as an FPGA, a PLD, or an ASIC. Any processor has a memory built in or connected to it, and any processor uses the memory to perform various processes.

The hardware resource for performing various processes may be configured by one of the various processors or by a combination of two or more processors of the same type or different types (for example, a combination of a plurality of FPGAs or a combination of a processor and an FPGA). Further, the hardware resource for performing various processes may be one processor.

A first example of the configuration in which the hardware resource is configured by one processor is an aspect in which one processor is configured by a combination of one or more processors and software and functions as the hardware resource for performing various processes. A second example of the configuration is an aspect in which a processor that implements the functions of the entire system including a plurality of hardware resources for performing various processes using one IC chip is used. A representative example of this aspect is an SoC. As described above, various processes are achieved using one or more of the various processors as the hardware resource.

In addition, specifically, an electronic circuit obtained by combining circuit elements, such as semiconductor elements, can be used as the hardware structure of the various processors. Further, the various processes are only an example. Therefore, it goes without saying that unnecessary steps may be deleted, new steps may be added, or the processing order may be changed, without departing from the gist.

The content described and illustrated above is a detailed description of portions related to the technology of the present disclosure and is only an example of the technology of the present disclosure. For example, the description of the configurations, functions, operations, and effects is the description of examples of the configurations, functions, operations, and effects of the portions related to the technology of the present disclosure. Therefore, it goes without saying that unnecessary portions may be deleted or new elements may be added or replaced in the content described and illustrated above, without departing from the gist of the technology of the present disclosure. In addition, the description of, for example, common technical knowledge that does not need to be particularly described to enable the implementation of the technology of the present disclosure is omitted in the content described and illustrated above in order to avoid confusion and to facilitate the understanding of the portions related to the technology of the present disclosure.

In the specification, "A and/or B" is synonymous with "at least one of A or B". That is, "A and/or B" means only A, only B, or a combination of A and B. Further, in the specification, the same concept as "A and/or B" is applied to a case in which the connection of three or more matters is expressed by "and/or".

All of the documents, the patent applications, and the technical standards described in the specification are incorporated by reference herein to the same extent as each individual document, each patent application, and each technical standard are specifically and individually stated to be incorporated by reference.

What is claimed is:

1. An endoscope system comprising:

an ultrasound endoscope, and an information processing apparatus comprising a processor, wherein the processor is configured to:

acquire an actual ultrasound image generated as an image showing an aspect of an observation target region including a specific part on the basis of reflected waves obtained by emitting ultrasonic waves from the ultrasound endoscope to the observation target region, acquire a virtual ultrasound image group including a plurality of virtual ultrasound images, each virtual ultrasound image virtually showing the aspect of the observation target region on the basis of volume data indicating the observation target region, the volume data being obtained by imaging a subject by a modality, wherein metadata is given to each virtual ultrasound image in the virtual ultrasound image group, and the metadata includes three-dimensional coordinates and an angle around a luminal-organ pathway, specify a positional relationship between a first position where the ultrasound endoscope is present and a second position where the specific part is present, for enhancing accuracy of movement of the ultrasound endoscope, by:

selecting, from the virtual ultrasound image group, a first virtual ultrasound image whose rate of match with the actual ultrasound image is equal to or greater than a predetermined value, acquiring, as metadata of the first position, metadata given to the selected first virtual ultrasound image, identifying, from the virtual ultrasound image group, a second virtual ultrasound image corresponding to a target position of the specific part, acquiring, as metadata of the second position, metadata given to the identified second virtual ultrasound image, and comparing the metadata of the first position and the metadata of the second position, perform a first presentation process of presenting, on a display, the first position toward the second position in a direction that shortens a distance between the first position and the second position, on the basis of the positional relationship, and guide the ultrasound endoscope from the first position toward the second position on the basis of the positional relationship.

2. The endoscope system according to claim 1, wherein, the first position and the second position are matched with each other and the processor performs a notification process of notifying that the first position and the second position are matched with each other.

3. The endoscope system according to claim 1, wherein the processor performs a first presentation process of presenting guidance information for guiding the first position to the second position on the basis of the positional relationship.

4. The information processing apparatus according to claim 1, wherein the actual ultrasound image is an ultrasound image generated in a Doppler mode.

5. The information processing apparatus according to claim 1, wherein the actual ultrasound image is an image that is based on an ultrasound image including a blood flow and on an ultrasound image in which intensity of the reflected waves is represented by brightness.

6. The information processing apparatus according to claim 1, wherein the processor acquires a first ultrasound image, which is an ultrasound image generated in a Doppler mode, and a second ultrasound image, which is an ultrasound image generated in a B-mode, as the actual ultrasound image, and after presenting first guidance information for guiding the first position to another position on the basis of the first ultrasound image and the virtual ultrasound image, performs a second presentation process of presenting second guidance information for guiding the first position to the second position according to the positional relationship specified on the basis of the second ultrasound image and the virtual ultrasound image.

7. The endoscope system according to claim 1, wherein the processor displays the actual ultrasound image on a display device.

8. The endoscope system according to claim 7, wherein the processor performs an image recognition process on the actual ultrasound image, at least one of the plurality of virtual ultrasound images, or both, and displays a result of the image recognition process on the display device.

9. The information processing apparatus according to claim 7, wherein the processor displays the virtual ultrasound image and the actual ultrasound image on the display device to be comparable with each other.

10. The information processing apparatus according to claim 9, wherein the processor selects the virtual ultrasound image whose rate of match with the actual ultrasound image is equal to or greater than a predetermined value from a plurality of the virtual ultrasound images for different positions in the observation target region, and displays the selected virtual ultrasound image and the actual ultrasound image on the display device to be comparable with each other.

11. The endoscope system according to claim 7, wherein the observation target region includes a luminal organ, and the processor displays a surface image, which is generated on the basis of the volume data and includes an inner surface of the luminal organ, and the actual ultrasound image on the display device to be comparable with each other.

12. The information processing apparatus according to claim 11, wherein the surface image is a video image that guides movement of the medical module.

13. The information processing apparatus according to claim 11, wherein the processor displays, on the display device, position specification information capable of specifying a position which corresponds to a position where the ultrasonic waves are emitted from the medical module in the surface image.

14. The information processing apparatus according to claim 13, wherein the virtual ultrasound image is a virtual ultrasound image showing an aspect of the observation target region for the position specified from the position specification information.

15. The endoscope system according to claim 1, wherein the medical module is a distal end part of an ultrasound endoscope having a treatment tool, and the specific part is a treatment target part that is treated by the treatment tool.

16. The endoscope system according to claim 15, wherein the treatment tool is a puncture needle, and the treatment target part is a part that is punctured by the puncture needle.

17. An ultrasound endoscope apparatus comprising:

the information processing apparatus according to claim 1; and an ultrasound endoscope having the medical module provided in a distal end part thereof.

* * * * *